(12) United States Patent
Duan et al.

(10) Patent No.: US 10,364,261 B2
(45) Date of Patent: Jul. 30, 2019

(54) DNA ALKYLATING AGENTS

(71) Applicant: OBI PHARMA, INC., Taipei (TW)

(72) Inventors: Jian-Xin Duan, South San Francisco, CA (US); Yeyu Cao, South San Francisco, CA (US); Xiaohong Cai, South San Francisco, CA (US); Hailong Jiao, South San Francisco, CA (US); Jing Yuan Ma, South San Francisco, CA (US); Mark Matteucci, South San Francisco, CA (US)

(73) Assignee: OBI PHARMA, INC., Taipei (TW)

( * ) Notice: Subject to any disclaimer, the term of this patent is extended or adjusted under 35 U.S.C. 154(b) by 0 days.

(21) Appl. No.: 15/557,053

(22) PCT Filed: Mar. 9, 2016

(86) PCT No.: PCT/US2016/021581
§ 371 (c)(1),
(2) Date: Sep. 8, 2017

(87) PCT Pub. No.: WO2016/145092
PCT Pub. Date: Sep. 15, 2016

(65) Prior Publication Data
US 2018/0044360 A1 Feb. 15, 2018

Related U.S. Application Data

(60) Provisional application No. 62/255,916, filed on Nov. 16, 2015, provisional application No. 62/131,163, filed on Mar. 10, 2015.

(51) Int. Cl.
*A61K 31/396* (2006.01)
*C07F 9/24* (2006.01)
*G01N 33/574* (2006.01)

(52) U.S. Cl.
CPC .......... *C07F 9/2466* (2013.01); *A61K 31/396* (2013.01); *G01N 33/57484* (2013.01); *G01N 33/57496* (2013.01); *G01N 2333/904* (2013.01); *G01N 2800/52* (2013.01)

(58) Field of Classification Search
CPC .. A61K 31/396; A61K 31/435; C07D 403/02; C07D 407/14
USPC ..................... 514/119; 546/268.1; 548/956
See application file for complete search history.

(56) References Cited

U.S. PATENT DOCUMENTS

| 5,472,956 | A | 12/1995 | Borch et al. |
| 6,482,953 | B1 | 11/2002 | Kim et al. |
| 8,507,464 | B2 | 8/2013 | Matteucci et al. |
| 2004/0214798 | A1 | 10/2004 | Hu |
| 2008/0269268 | A1 | 10/2008 | Schirok et al. |
| 2010/0256139 | A1 | 10/2010 | Rockway et al. |
| 2011/0251159 | A1 | 10/2011 | Matteucci et al. |
| 2014/0010805 | A1 | 1/2014 | Hart et al. |
| 2014/0170240 | A1 | 6/2014 | Matteucci et al. |
| 2018/0044360 | A1 | 2/2018 | Duan et al. |

FOREIGN PATENT DOCUMENTS

| CN | 102924507 A | 2/2013 |
| JP | 2018-513876 A | 5/2018 |
| WO | WO-2004/087075 | 10/2004 |
| WO | WO-2006/057946 A2 | 6/2006 |
| WO | WO-2007/002931 A2 | 1/2007 |
| WO | WO-2007/098089 A2 | 8/2007 |
| WO | WO-2008/083101 A1 | 7/2008 |
| WO | WO-2008/151253 A1 | 12/2008 |
| WO | WO-2009/018163 A1 | 2/2009 |
| WO | WO-2010/044686 | 4/2010 |
| WO | WO-2010/048330 A1 | 4/2010 |
| WO | WO-2011/066416 A1 | 6/2011 |
| WO | WO-2014/131023 | 8/2014 |
| WO | WO-2015/051921 A1 | 4/2015 |
| WO | WO-2016/161342 A2 | 10/2016 |
| WO | WO-2016/210175 A1 | 12/2016 |
| WO | WO-2017/087428 A1 | 5/2017 |

OTHER PUBLICATIONS

Jain, M. et al. (2004) "Sulfonyl-containing aldophosphamide analogues as novel anticancer prodrugs targeted against cyclophosphamide-resistant tumor cell lines," Journal of Medicinal Chemistry 47(15):3843-3852.
Mulcahy, R.T. et al. (1994) "Nitrobenzyl phosphorodiamidates as potential hypoxia-selective alkylating agents", Journal of Medicinal Chemistry 37:1610-1615.
Guise, C.P. et al. (2014) "Bioreductive prodrugs as cancer therapeutics: targeting tumor hypoxia," Chinese Journal of Cancer 33(2):80-86.
International Search Report and Written Opinion (ISA/US) for International Application No. PCT/US2016/021581, dated Jun. 2, 2016.
Chen, Y. et al., "Design of anticancer prodrugs for reductive activation", Medicinal Research Reviews, vol. 29, No. 1, 2009, pp. 29-64.
Communication pursuant to Rules 70(2) and 70a(2) EPC issued in EP 16815334.4 dated Jan. 8, 2019, 1 page.

(Continued)

*Primary Examiner* — Jeffrey H Murray
(74) *Attorney, Agent, or Firm* — Foley & Lardner LLP; Daniel R. Shelton

(57) ABSTRACT

Provided herein are compounds of formula I: wherein the variables are defined herein, processes of making them, and methods of treating cancer comprising administering such compounds.

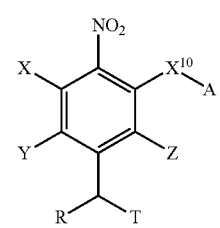

11 Claims, 11 Drawing Sheets

(56) References Cited

OTHER PUBLICATIONS

Duan, J-X. et al. (2008) "Potent and Highly Selective Hypoxia-Activated Achiral Phosphoramidate Mustards as Anticancer Drugs," J. Med Chem 51:2412-2420.
Extended European search report issued in 16762438.6 dated Jul. 3, 2018, 10 pages.
Extended European Search Report issued in 16774352.5 dated Nov. 6, 2018, 11 pages.
Extended European Search Report issued in 16815334.4 dated Dec. 21, 2018, 7 pages.
Golub, T.R. et al. (1999) "Molecular Classification of Cancer: Class Discovery and Class Prediction by Gene Expression Monitoring," Science 286:531-537.
Hay et al. Substituent effects on the kinetics of reductively-initiated fragmentation of nitrobenzyl carbamates designed as triggers for bioreductive prodrugs, J. Chem. Soc., Perkin Trans. 1, 1999, 2759-2770. (Year:1999).
Hu et al., "Synthesis and structure-activity relationships of nitrobenzyl phosphoramide mustards as nitroreductase-activated prodrugs", Bioorganic & Medicinal Chemistry Letters 21 (2011) 3986-3991.
International Preliminary Report on Patentability issued in PCT/US2016/039092 dated Jan. 4, 2018, 9 pages.
K. Misiura et al., "Stereospecific synthesis of chiral metabolites of Ifosfamide and their determination in the Urine", Journal of Medicinal Chemistry., vol. 26, 1983, pp. 674-679, XP002786859, Usamerican Chemical Society. Washington. ISSN: 0022-2623.
Li, Z. et al., "Nitrobenzocyclophosphamides as Potential Prodrugs for Bioreductive Activation: Synthesis, Stability, Enzymatic Reduction, and Antiproliferative Activity in Cell Culture", Bioorganic & Medicinal Chemistry, vol. 11, No. 19, 2003, pp. 4171-4178.
Nih National Cancer Institute (2015) "Targeted Cancer Therapies Fact Sheet," see http://www.cancer.gov/about-cancer/treatment/types/targeted-therapies/targeted-therapies-fact-sheet, accessed Dec. 8, 2015.
Rastelli et al. Discovery of New Inhibitors of Aldose Reductase from Molecular Docking and Database Screening. Bioorganic & Medicinal Chemistry 10 (2002) 1437-1450. (Year: 2002).

DNA ALKYLATING AGENTS

CROSS-REFERENCE TO RELATED APPLICATIONS

This application is a national stage application under 35 U.S.C. § 371 of International Application No. PCT/US2016/021581, filed Mar. 9, 2016, which in turn claims priority under 35 U.S.C. § 119(e) to U.S. Provisional Patent Application No. 62/131,163, filed Mar. 10, 2015, and U.S. Provisional Patent Application No. 62/255,916, filed Nov. 16, 2015, the content of each of which is hereby incorporated by reference in its entirety.

FIELD OF INVENTION

The present invention provides compounds suitable as therapeutic agents and intermediates thereto, pharmaceutical compositions of such compounds and methods of treating cancer in cancer patients, and so relates to the fields of biology, chemistry, and medicine.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment is a cause of adverse side effects in patients and can limit the amount of anti-cancer drug administered to a cancer patient.

Aldo-keto reductase family 1 member C3 is an enzyme that in humans is encoded by the AKR1C3 gene. This gene encodes a member of the aldo/keto reductase superfamily, which consists of more than 40 known enzymes and proteins. These enzymes catalyze the conversion of aldehydes and ketones to their corresponding alcohols by utilizing NADH and/or NADPH as cofactors.

Many cancer cells overexpress AKR1C3 reductase relative to normal cells (See, Cancer Res 2010; 70:1573-1584, Cancer Res 2010; 66: 2815-2825).

PR 104:

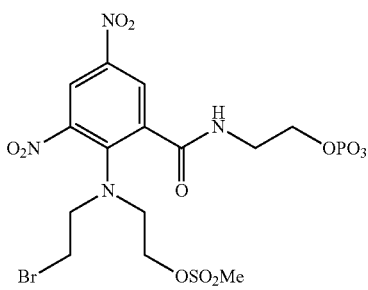

PR 104 has been shown to be a weak substrate for AKR1C3 and was tested in the clinical trials. This compound is not a selective AKR1C3 activated prodrug as it can also be activated under hypoxic conditions. PR104 was ineffective in clinical trials.

There remains a need for compounds suitable for treating cancer patients, including for selective AKR1C3 reductase activated prodrugs for treating cancer patients. The present invention meets this need.

SUMMARY OF THE INVENTION

In one aspect, provided herein are compounds of formula I:

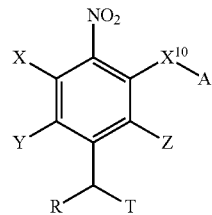

I and pharmaceutically acceptable salts, and solvates of each thereof, wherein $X^{10}$ is O, S, SO, or $SO_2$;

A is $C_6$-$C_{10}$ aryl, 5-15 membered heteroaryl, or —N=$CR^1R^2$;

each $R^1$ and $R^2$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each X, Y, and Z independently is hydrogen, CN, halo, $C_1$-$C_6$ alkyl, $C_2$-$C_6$ alkenyl, $C_2$-$C_6$ alkynyl, $C_3$-$C_8$ cycloalkyl $C_6$-$C_{10}$ aryl, 4-15 membered heterocycle, 5-15 membered heteroaryl, ether, —$CONR^{13}R^{14}$, or —$NR^{13}COR^{14}$;

R is hydrogen, $C_1$-$C_6$ alkyl, $C_2$-$C_6$ alkenyl, $C_2$-$C_6$ alkynyl, $C_3$-$C_8$ cycloalkyl, $C_6$-$C_{19}$ aryl, 4-15 membered heterocycle, 5-15 membered heteroaryl, ether, —$CONR^{13}R^{14}$, or —$NR^{13}COR^{14}$; each $R^{13}$ and $R^{14}$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, or ether;

T comprises a phosphoramidate alkylating agent; and wherein the alkyl, alkenyl, alkynyl, cycloalkyl, aryl, heterocycle, heteroaryl, ether groups are optionally substituted.

In another embodiment, provided herein is a compound of formula I-A

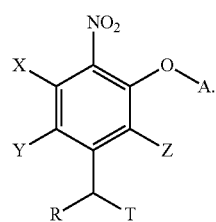

I-A

In another embodiment, $X^{10}$ is S.

In one embodiment, T is is $OP(Z^1)(NR^{30}CH_2CH_2X^1)_2$, $OP(Z^1)(NR^{30}_2)(N(CH_2CH_2X^1)_2)$ $OP(Z^1)(N(CH_2CH_2))_2$, $OP(Z^1)(N(CH_2CH_2X^1)_2)_2$, wherein each $R^{30}$ independently is hydrogen or $C_1$-$C_6$ alkyl or 2 $R^{30}$s together with the nitrogen atom they are bound to form 5-7 membered heterocyclyl group, $Z^1$ is O or S, and $X^1$ is Cl, Br, or OMs or another leaving group. In one embodiment, T is is $OP(Z^1)(NHCH_2CH_2Cl)_2$, $OP(Z^1)(NHCH_2CH_2Br)2$, $OP(Z^1)(NH_2)(N(CH_2CH_2X^1)_2)$ $OP(Z^1)N(CH_2)_2)_2$, $OP(Z^1)(N(CH_2CH_2Cl)_2)_2$, wherein $Z^1$ is O or S, and $X^1$ is Cl, Br, or OMs. In one embodiment, $Z^1$ is O. In another embodiment, $Z^1$ is S. In another embodiment, T is $OP(O)(N(CH_2CH_2))_2$.

The compounds provided herein include individual diastereomers and other geometric isomers, and enantiomers, and mixtures of enantiomers, diastereomers, and geometric isomers other than diastereomers.

In another aspect, provided herein is a pharmaceutical composition comprising a compound provided herein and at least one pharmaceutically acceptable excipient. In another aspect, provided herein is a unit dose of the pharmaceutical composition provided herein.

In another aspect, provided herein is a method for treating cancer in a patient, comprising administering to the patient a therapeutically effective amount of a compound or a pharmaceutically acceptable composition as provided herein. In one embodiment, the cancer is one wherein AKR1C3 reductase levels are high or are higher than usual in such a cancer. In one embodiment, the cancer is liver cancer. In one embodiment, the cancer is non-small cell lung cancer or melanoma. In a further aspect, the method comprises determining the AKR1C3 reductase level of the cancer by methods using an AKR1C3 antibody, and administering a therapeutically effective amount of a compound or a pharmaceutically acceptable composition provided herein to said patient if said level is equal to or greater than a predetermined value. In one aspect, the method comprises prior to administration, determining an intratumoral AKR1C3 reductase level in a sample isolated from the patient and selecting the patient for the therapy if the level is equal to or greater than a predetermined level. In some embodiments, a therapeutically effective amount of a cancer treatment other than a treatment comprising administration of a compound or a pharmaceutically acceptable composition provided herein is administered if the level does not exceed or is less than said predetermined value. In some embodiments, provided herein is a kit comprising a means for isolating a sample from a patient and determining an intratumoral AKR1C3 reductase level of the cancer in the sample using an AKR1C3 antibody; and a means for determining whether a compound or composition provided herein should be administered. Methods of determining the therapeutically effective amount, appropriate mode of administration of the compounds and compositions provided herein will be apparent to the skilled artisan upon reading this disclosure and based on other methods known to them. AKR1C3 levels are measured following routine methods well known to the skilled artisan.

DETAILED DESCRIPTION

Definitions

Figure 1:
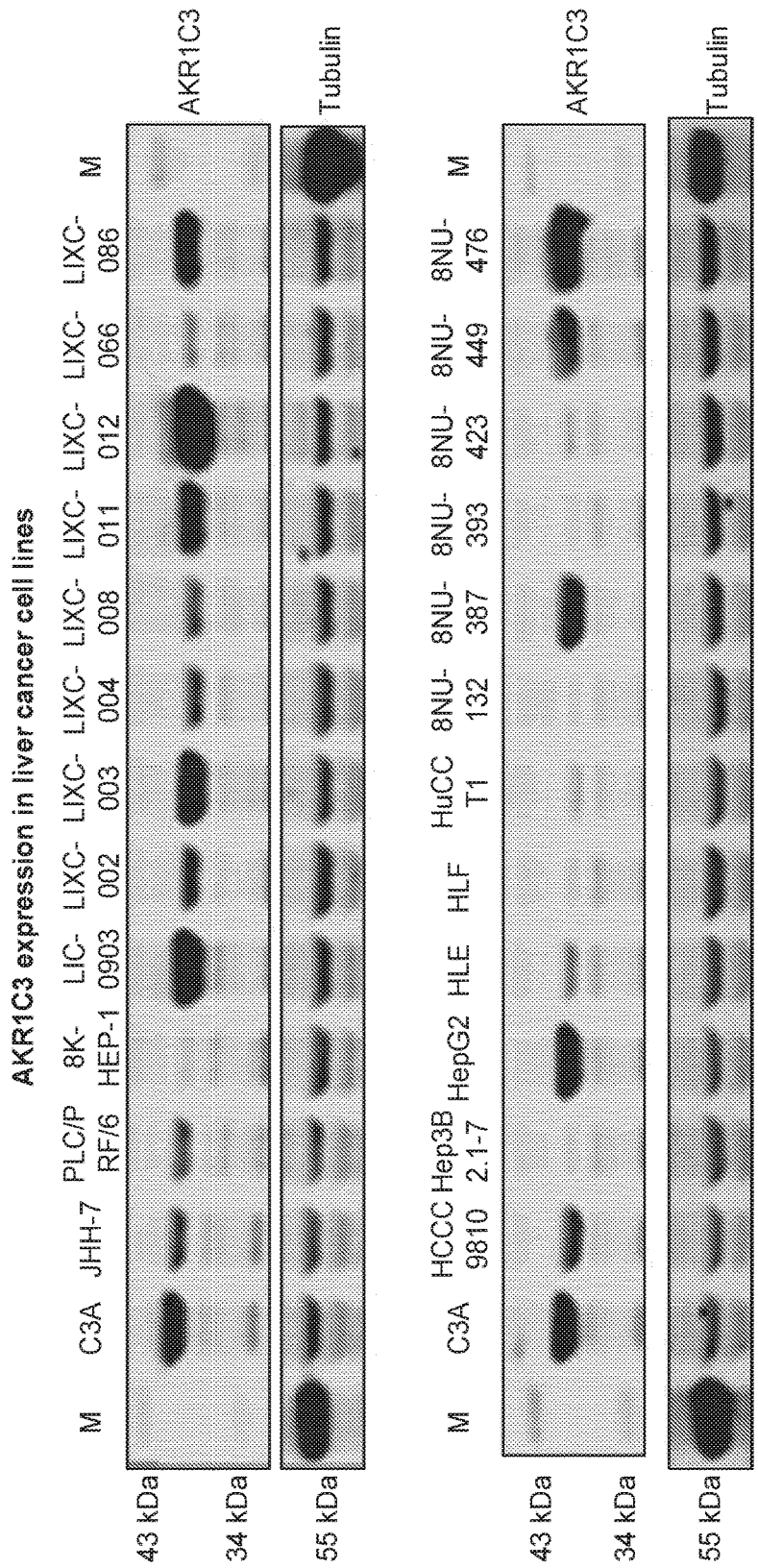
FIG. 1 illustrates AKR1C3 expression in liver cancer cell lines.

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., temperature, time, concentration, and weight, including ranges of each thereof, are approximations that typically may be varied (±) or (−) by increments of 0.1, 1.0, or 10.0, as appropriate. All numerical designations may be understood as preceded by the term "about". Reagents described herein are exemplary and equivalents of such may be known in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"$C_x$-$C_y$" or "$C_{x-y}$" before a group refers to a range of the number of carbon atoms that are present in that group. For example, $C_1$-$C_6$ alkyl refers to an alkyl group having at least 1 and up to 6 carbon atoms.

"Alkoxy" refers to —O-Alkyl.

"Amino" refers to $NR^pR^q$ wherein $R^p$ and $R^q$ independently are hydrogen or $C_1$-$C_6$ alklyl, or $R^p$ and $R^q$ together with the nitrogen atom they are bonded to form a 4-15 membered heterocycle.

"Alkyl" refers to monovalent saturated aliphatic hydrocarbyl groups having from 1 to 10 carbon atoms and, in some embodiments, from 1 to 6 carbon atoms. "$C_{x-y}$ alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" refers to divalent saturated aliphatic hydrocarbyl groups having from 1 to 10 carbon atoms and, in some embodiments, from 1 to 6 carbon atoms. "$C_{u-v}$alkylene" refers to alkylene groups having from u to v carbon atoms. The alkylidene and alkylene groups include branched and straight chain hydrocarbyl groups. For example, "$C_{1-6}$ alkylene" includes methylene, ethylene, propylene, 2-methypropylene, pentylene, and the like. "Heteroalkylene" refers to an alkylene wherein a chain carbon atom is replaced with a heteroatom such as O, S, N, or P, or a heteroatom containing substituent.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $C_{x-y}$ alkenyl refers to alkenyl groups having from x to y carbon atoms and is meant to include, for example, ethenyl, propenyl, 1,3-butadienyl, and the like. "Alkenylene" refers to a divalent alkenyl radical having the appropriate hydrogen content. "Heteroalkenylene" refers to an alkenylene wherein a chain carbon atom is replaced with a heteroatom such as O, S, N, or P, or a heteroatom containing substituent.

"Phosphoramidate alkylating agent" refers to an alkylating agent comprising one or more $Z^5$—$X^5$—$Y^5$ moieties bonded to an —O—P($Z^1$) moiety, where $Z^5$ is a heteroatom such as nitrogen, sulfur or oxygen, $X^5$ is optionally substituted ethylene, $Y^5$ is halo or another leaving group, or $Z^5$—$X^5$—$Y^5$ together form an aziridinyl ($NCH_2CH_2$) moiety, and $Z^1$ is defined as above. Such an alkylating agent can react with a DNA or another nucleic acid, or a protein. In some instances an alkylating agent can cross link a DNA.

"Alkynyl" refers to a linear monovalent hydrocarbon radical or a branched monovalent hydrocarbon radical 2 to 10 carbon atoms and in some embodiments from 2 to 6 carbon atoms or 2 to 4 carbon atoms and containing at least one triple bond. The term "alkynyl" is also meant to include those hydrocarbyl groups having one triple bond and one double bond. For example, $C_{2-6}$ alkynyl includes ethynyl, propynyl, and the like. "Alkynylene" refers to a divalent alkynyl radical having the appropriate hydrogen content. "Heteroalkynylene" refers to an alkynylene wherein a chain carbon atom is replaced with a heteroatom such as O, S, N, or P, or a heteroatom containing substituent.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5, 7, 8 tetrahydronaphthalene-2-yl is an aryl group as its point of attachment is at the 2-position of the aromatic phenyl ring). "Arylene" refers to a divalent aryl radical having the appropriate hydrogen content.

"Cycloalkyl" refers to a saturated or partially saturated cyclic group of from 3 to 14 carbon atoms and no ring heteroatoms and having a single ring or multiple rings including fused, bridged, and Spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl. "Cycloalkylene" refers to a divalent cycloalyl radical having the appropriate hydrogen content.

"Ether" refers to a $C_1$-$C_6$ alkyl group substituted with $C_1$-$C_6$ alkoxy groups, wherein alkoxy refers to —O-alkyl.

"Halo" refers to one or more of fluoro, chloro, bromo, and iodo.

"Heteroaryl" refers to an aromatic group of from 1 to 14 carbon atoms and 1 to 6 heteroatoms selected from the group consisting of oxygen, nitrogen, and sulfur and includes single ring (e.g. imidazolyl-2-yl and imidazol5-yl) and multiple ring systems (e.g. imidazopyridyl, benzotriazolyl, benzimidazol-2-yl and benzimidazol-6-yl). For multiple ring systems, including fused, bridged, and spiro ring systems having aromatic and non-aromatic rings, the term "heteroaryl" applies if there is at least one ring heteroatom, and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atoms) of the heteroaryl group are optionally oxidized to provide for the N-oxide (N→O), sulfinyl, or sulfonyl moieties. The term heteroaryl includes, but is not limited to, acridinyl, azocinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzothienyl, benzimidazolinyl, carbazolyl, NH-carbazolyl, carbolinyl, chromanyl, chromenyl, cinnolinyl, dithiazinyl, furanyl, furazanyl, imidazolidinyl, imidazolinyl, imidazopyridyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isoquinolyl, isothiazolyl, isoxazolyl, naphthyridinyl, octahydroisoquinolinyl, oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazole, pyridinyl, pyridyl, pyrimidinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl. "Heteroarylene" refers to a divalent heteroaryl radical having the appropriate hydrogen content.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings; the terms "heterocyclic", "heterocycle", "heterocycloalkyl", or "heterocyclyl" apply when there is at least one ring heteroatom, and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In some embodiment, the heterocyclic groups herein are 3-15 membered, 4-14 membered, 5-13 membered, 7-12, or 5-7 membered heterocycles. In some other embodiment, the heterocycles contain 4 heteroatoms. In some other embodiment, the heterocycles contain 3 heteroatoms. In another embodiment, the heterocycles contain up to 2 heteroatoms. In some embodiments, the nitrogen and/or sulfur atom(s) of the heterocyclic group are optionally oxidized to provide for the N-oxide, sulfinyl, sulfonyl moieties. Heterocyclyl includes, but is not limited to, tetrahydropyranyl, piperidinyl N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_{3-10}$) refers to the total number of carbon atoms in the portion of the heterocyclyl group exclusive of the number of heteroatoms. A divalent heterocyclic radical will have the appropriately adjusted hydrogen content.

"Leaving group" refers to a moiety that can be displaced under nucleophilic displacement conditions well known to the skilled artisan. Leaving groups include, without limitation halo and —$OSO_2$—$R^{20}$, (where $R^{20}$ is optionally substituted alkyl, aryl, cycloalkyl, heterocyclyl, or heteroaryl.

The term "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, $NO_2$, —$N_2$+, —$CO_2R^{100}$, —$OR^{100}$, —$SR^{100}$, —$SOR^{100}$, —$SO_2R^{100}$, —$NR^{100}SO_2R^{100}$, —$NR^{101}R^{102}$, —$CONR^{101}R^{102}$, —$SO_2NR^{101}R^{102}$, $C_1$-$C_6$ alkyl, $C_1$-$C_6$ alkoxy, —$CR^{100}$=$CCR^{100}$, $C_3$-$C_{10}$ cycloalkyl, $C_3$-$C_{10}$ heterocyclyl, $C_6$-$C_{12}$ aryl and $C_2$-$C_{12}$ heteroaryl, or a divalent substituent such as —O—($CH_2$)—O—, —O—($CH_2$)$_2$—O—, and, 1-4 methyl substituted version thereof, wherein each $R^{100}$, $R^{101}$, and $R^{102}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; or $R^{101}$ and $R^{102}$ together with the nitrogen atom they are attached to form a 5-7 membered heterocycle; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. Preferably, the substituents are selected from the group consisting of chloro, fluoro, —$OCH_3$, methyl, ethyl, isopropyl, cyclopropyl, —$CO_2H$ and salts and $C_1$-$C_6$ alkyl esters thereof, $CONMe_2$, $CONHMe$, $CONH_2$, —$SO_2Me$, —$SO_2NH_2$, —$SO_2NMe_2$, —$SO_2NHMe$, —$NHSO_2Me$, —$NHSO_2CF_3$, —$NHSO_2CH_2Cl$, —$NH_2$, —$OCF_3$, —$CF_3$ and —$OCHF_2$.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Cancer" refers to leukemias, lymphomas, carcinomas, and other malignant tumors, including solid tumors, of potentially unlimited growth that can expand locally by invasion and systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Patient" and "subject" are used interchangeably to refer to a mammal in need of treatment for cancer. Generally, the patient is a human. Generally, the patient is a human diagnosed with cancer. In certain embodiments a "patient" or "subject" may refer to a non-human mammal used in screening, characterizing, and evaluating drugs and therapies, such as, a non-human primate, a dog, cat, rabbit, pig, mouse or a rat.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Solid tumor" refers to solid tumors including, but not limited to, metastatic tumors in bone, brain, liver, lungs, lymph node, pancreas, prostate, skin and soft tissue (sarcoma).

"Therapeutically effective amount" of a drug refers to an amount of a drug that, when administered to a patient with cancer, will have the intended therapeutic effect, e.g., alleviation, amelioration, palliation or elimination of one or more manifestations of cancer in the patient. A therapeutic effect does not necessarily occur by administration of one dose, and may occur only after administration of a series of doses. Thus, a therapeutically effective amount may be administered in one or more administrations.

"Treating," "treatment of," or "therapy of" a condition or patient refers to taking steps to obtain beneficial or desired results, including clinical results. For purposes of this invention, beneficial or desired clinical results include, but are not limited to, alleviation or amelioration of one or more symptoms of cancer; diminishment of extent of disease; delay or slowing of disease progression; amelioration, palliation, or stabilization of the disease state; or other beneficial results. Treatment of cancer may, in some cases, result in partial response or stable disease.

"Tumor cells" refers to tumor cells of any appropriate species, e.g., mammalian such as murine, canine, feline, equine or human.

Descriptive Embodiments

Provided herein are compound of formulas I as disclosed herein above.

In one aspect, provided herein are compounds of formula I-A:

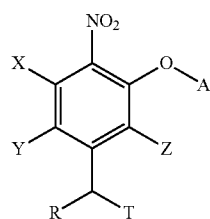

I-A and pharmaceutically acceptable salts and solvates thereof, wherein

A is $C_6$-$C_{10}$ aryl, 5-15 membered heteroaryl, or —N=$CR^1R^2$;

each $R^1$ and $R^2$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each X, Y, and Z independently is hydrogen, CN, halo, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

R is hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$; each $R^{13}$ and $R^{14}$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, or ether;

wherein the alkyl, alkenyl, alkynyl, cycloalkyl, aryl, heterocycle, heteroaryl, ether groups are optionally substituted; and T is a phosphoramidate alkylating agent.

In one embodiment, Z is hydrogen. In another embodiment, X is hydrogen. In another embodiment, Y is hydrogen. In another embodiment, Y is halo.

In another embodiment, A is optionally substituted $C_6$-$C_{10}$ aryl. In another embodiment, A is optionally substituted phenyl. In another embodiment, the phenyl is optionally substituted with 1-3, 1-2, or a substituent selected from halo, —CN, $NO_2$, —$CO_2R^{100}$, —$OR^{100}$), —$SR^{100}$, —$SOR^{100}$, —$SO_2R^{100}$, —$NR^{100}SO_2R^{100}$, —$NR^{101}R^{102}R^{102}$, —$CONR^{101}R^{102}$, —$SO_2NR^{101}R^{102}$, $C_1$-$C_6$ alkyl, $C_1$-$C_6$ alkoxy, $C_2$-$C_{10}$ cycloalkyl, $C_3$-$C_{10}$ heterocyclyl, $C_6$-$C_{12}$ aryl and $C_2$-$C_{12}$ heteroaryl, or a divalent substituent such as —O—($CH_2$)—O—, —O—($CH_2$)$_2$—O—, wherein each $R^{100}$, $R^{101}$, and $R^{102}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; or $R^{101}$ and $R^{102}$ together with the nitrogen atom they are attached to form a 5-7 membered heterocycle; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups.

In another embodiment, A is optionally substituted 5-15 membered heteroaryl. In another embodiment, A is optionally substituted pyridyl. In another embodiment, A is optionally substituted benzothiazolyl.

In another embodiment, A is —N=$CR^1R^2$ where $R^1$ and $R^2$ are defined as herein.

In some embodiments, R is hydrogen. In some embodiments, R is $C_1$-$C_6$ alkyl. In some embodiments, R is methyl.

In certain embodiments, suitable substituents for A is disclosed as part of the specific compounds tabulated herein below.

In one embodiment, T is OP(Z)(NHCH$_2$CH$_2$Cl)$_2$, OP(Z)(NHCH$_2$CH$_2$Br)$_2$, OP(Z)(NH$_2$)(N(CH$_2$CH$_2$X)$_2$) OP(Z)(N(CH$_2$)$_2$)$_2$, OP(Z)(N(CH$_2$CH$_2$Cl)$_2$)$_2$; Z=O or S; and X=Cl, Br, and OMs (—OSO$_2$Me).

In another embodiment, T is OP(O)(NHCH$_2$CH$_2$Cl)$_2$. In another embodiment, T is OP(O)(NHCH$_2$CH$_2$Br)$_2$. In another embodiment, T is OP(O)(NH$_2$)(N(CH$_2$CH$_2$Cl)$_2$), In another embodiment, provided herein is a compound tabulated below or a pharmaceutically acceptable salt or a solvate of each thereof; its anti-proliferation efficacy on H460 lung cancer cells is also tabulated.

| Compound number | Structure | IC 50 in proliferation assay in H460 cells (uM) |
|---|---|---|
| 2768 | 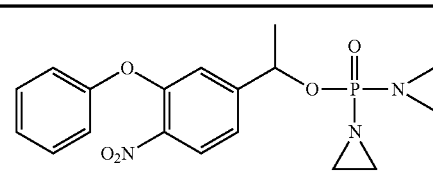 | 0.04 |

| Compound number | Structure | IC 50 in proliferation assay in H460 cells (uM) |
|---|---|---|
| 2846 | 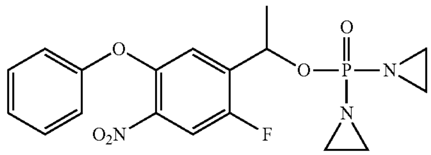 [SMILES: CC(OP(=O)(N1CC1)N1CC1)c1cc(Oc2ccccc2)c([N+](=O)[O-])cc1F] | 0.06 |
| 2850 | 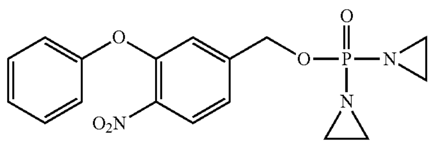 [SMILES: O=[N+]([O-])c1ccc(COP(=O)(N2CC2)N2CC2)cc1Oc1ccccc1] | 0.02 |
| 2852 | 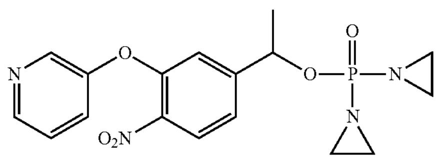 [SMILES: CC(OP(=O)(N1CC1)N1CC1)c1ccc([N+](=O)[O-])c(Oc2cccnc2)c1] | 0.02 |
| 2853 | 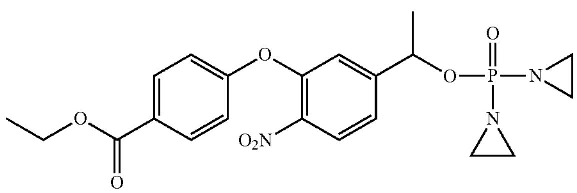 [SMILES: CCOC(=O)c1ccc(Oc2cc(C(C)OP(=O)(N3CC3)N3CC3)ccc2[N+](=O)[O-])cc1] | <0.005 |
| 2854 | 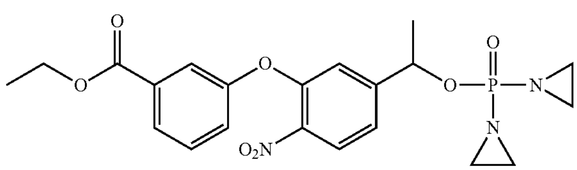 [SMILES: CCOC(=O)c1cccc(Oc2cc(C(C)OP(=O)(N3CC3)N3CC3)ccc2[N+](=O)[O-])c1] | <0.005 |
| 2855 | 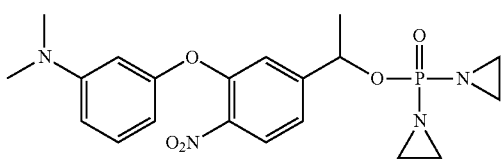 [SMILES: CC(OP(=O)(N1CC1)N1CC1)c1ccc([N+](=O)[O-])c(Oc2cccc(N(C)C)c2)c1] | 0.03 |
| 2860 | 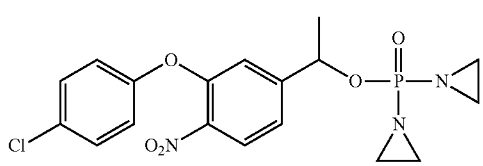 [SMILES: CC(OP(=O)(N1CC1)N1CC1)c1ccc([N+](=O)[O-])c(Oc2ccc(Cl)cc2)c1] | 0.01 |
| 2861 | 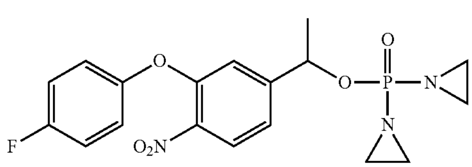 [SMILES: CC(OP(=O)(N1CC1)N1CC1)c1ccc([N+](=O)[O-])c(Oc2ccc(F)cc2)c1] | 0.02 |
| 2862 | 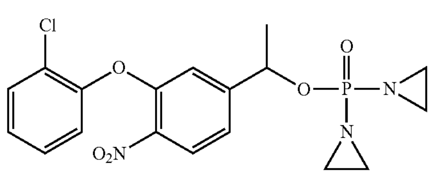 | 0.04 |

-continued

| Compound number | Structure | IC 50 in proliferation assay in H460 cells (uM) |
| --- | --- | --- |
| 2863 | 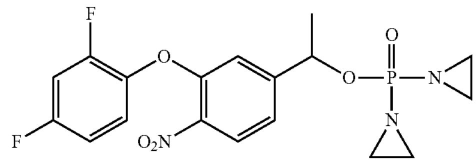 [SMILES: CC(OP(=O)(N1CC1)N1CC1)c1ccc([N+](=O)[O-])c(Oc2ccc(F)cc2F)c1] | 0.02 |
| 2864 | 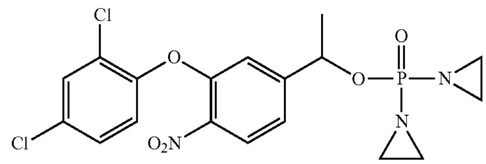 [SMILES: CC(OP(=O)(N1CC1)N1CC1)c1ccc([N+](=O)[O-])c(Oc2ccc(Cl)cc2Cl)c1] | 0.02 |
| 2865 | 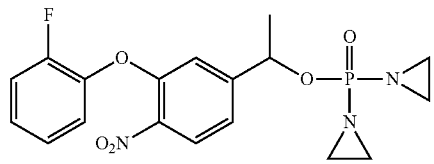 | 0.03 |
| 2866 | 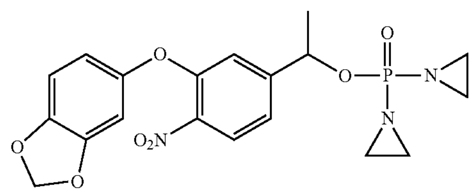 [SMILES: CC(OP(=O)(N1CC1)N1CC1)c1ccc([N+](=O)[O-])c(Oc2ccc3c(c2)OCO3)c1] | 0.02 |
| 2870 | 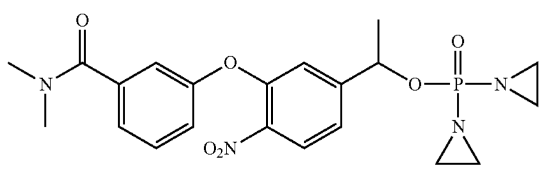 [SMILES: CC(OP(=O)(N1CC1)N1CC1)c1ccc([N+](=O)[O-])c(Oc2cccc(C(=O)N(C)C)c2)c1] | 0.0004 |
| 2871 | 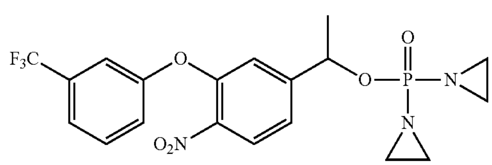 [SMILES: CC(OP(=O)(N1CC1)N1CC1)c1ccc([N+](=O)[O-])c(Oc2cccc(C(F)(F)F)c2)c1] | 0.03 |
| 2872 | 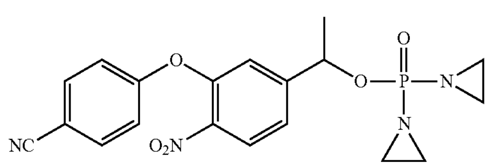 [SMILES: CC(OP(=O)(N1CC1)N1CC1)c1ccc([N+](=O)[O-])c(Oc2ccc(C#N)cc2)c1] | 0.03 |
| 2873 | 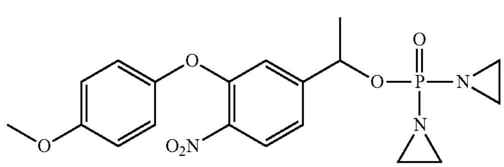 [SMILES: COc1ccc(Oc2cc(C(C)OP(=O)(N3CC3)N3CC3)ccc2[N+](=O)[O-])cc1] | 0.005 |
| 2874 | 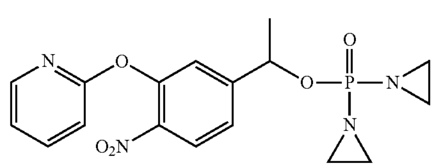 [SMILES: CC(OP(=O)(N1CC1)N1CC1)c1ccc([N+](=O)[O-])c(Oc2ccccn2)c1] | 0.5 |

-continued

| Compound number | Structure | IC 50 in proliferation assay in H460 cells (uM) |
|---|---|---|
| 2875 | 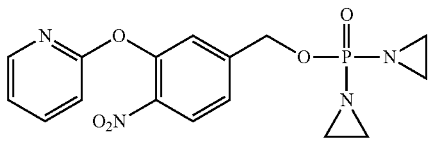 [SMILES: O=[N+]([O-])c1ccc(COP(=O)(N2CC2)N2CC2)cc1Oc1ccccn1] | 3.2 |
| 2876 | 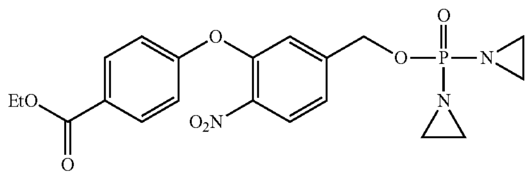 [SMILES: CCOC(=O)c1ccc(Oc2cc(COP(=O)(N3CC3)N3CC3)ccc2[N+](=O)[O-])cc1] | 0.003 |
| 2877 | 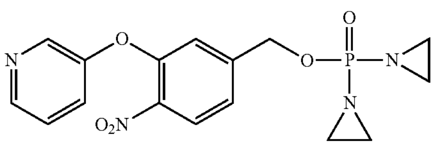 [SMILES: O=[N+]([O-])c1ccc(COP(=O)(N2CC2)N2CC2)cc1Oc1cccnc1] | 0.02 |
| 2878 | 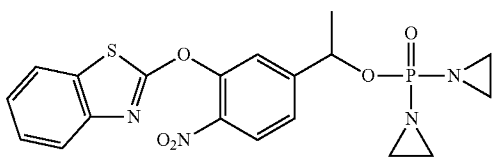 [SMILES: CC(OP(=O)(N1CC1)N1CC1)c1ccc([N+](=O)[O-])c(Oc2nc3ccccc3s2)c1] | 4.4 |
| 2880 | 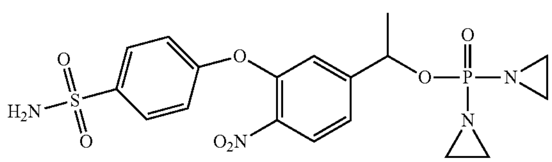 [SMILES: CC(OP(=O)(N1CC1)N1CC1)c1ccc([N+](=O)[O-])c(Oc2ccc(S(N)(=O)=O)cc2)c1] | 0.1 |
| 2881 | 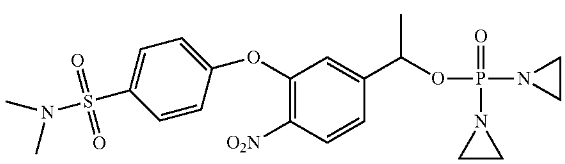 [SMILES: CC(OP(=O)(N1CC1)N1CC1)c1ccc([N+](=O)[O-])c(Oc2ccc(S(=O)(=O)N(C)C)cc2)c1] | 0.03 |
| 2882 | 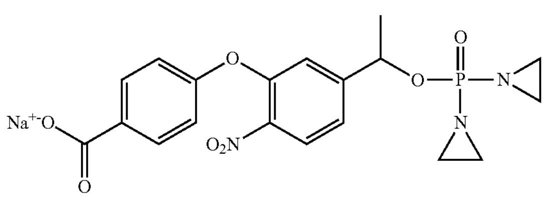 | 3.4 |
| 2883 | 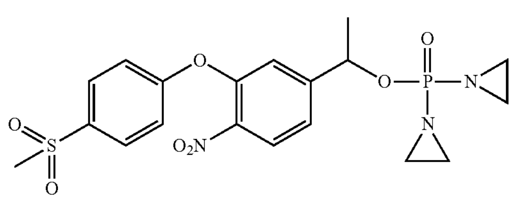 [SMILES: CC(OP(=O)(N1CC1)N1CC1)c1ccc([N+](=O)[O-])c(Oc2ccc(S(C)(=O)=O)cc2)c1] | 0.03 |

-continued

| Compound number | Structure | IC 50 in proliferation assay in H460 cells (uM) |
|---|---|---|
| 2884 | 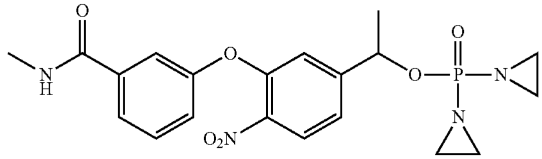 [SMILES: CNC(=O)c1cccc(Oc2cc(C(C)OP(=O)(N3CC3)N3CC3)ccc2[N+](=O)[O-])c1] | 0.01 |
| 2885 | 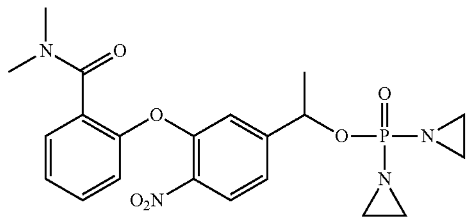 [SMILES: CC(OP(=O)(N1CC1)N1CC1)c1ccc([N+](=O)[O-])c(Oc2ccccc2C(=O)N(C)C)c1] | 3.7 |
| 2887 | 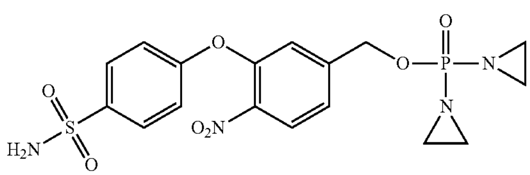 [SMILES: NS(=O)(=O)c1ccc(Oc2cc(COP(=O)(N3CC3)N3CC3)ccc2[N+](=O)[O-])cc1] | 0.2 |
| 2888 | 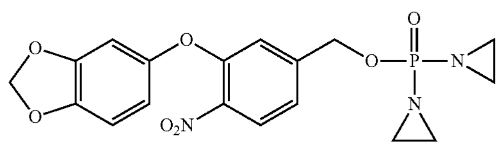 [SMILES: O=[N+]([O-])c1ccc(COP(=O)(N2CC2)N2CC2)cc1Oc1ccc2c(c1)OCO2] | 0.003 |
| 2889 | 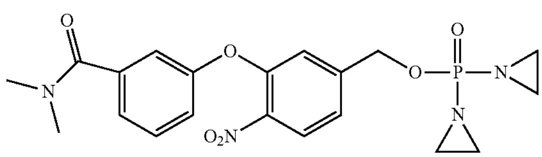 [SMILES: CN(C)C(=O)c1cccc(Oc2cc(COP(=O)(N3CC3)N3CC3)ccc2[N+](=O)[O-])c1] | 0.003 |
| 2890 | 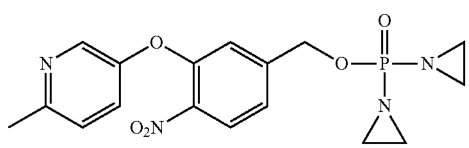 [SMILES: Cc1ccc(Oc2cc(COP(=O)(N3CC3)N3CC3)ccc2[N+](=O)[O-])cn1] | 0.006 |
| 2891 | 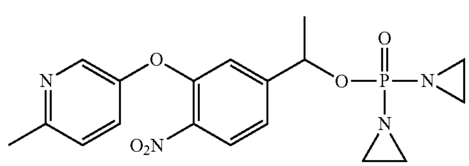 [SMILES: Cc1ccc(Oc2cc(C(C)OP(=O)(N3CC3)N3CC3)ccc2[N+](=O)[O-])cn1] | 0.03 |
| 2892 | 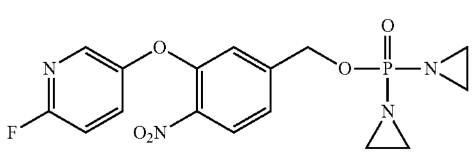 [SMILES: O=[N+]([O-])c1ccc(COP(=O)(N2CC2)N2CC2)cc1Oc1ccc(F)nc1] | 0.002 |
| 2893 | 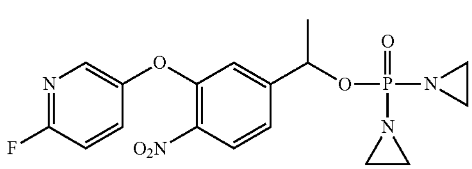 [SMILES: CC(OP(=O)(N1CC1)N1CC1)c1ccc([N+](=O)[O-])c(Oc2ccc(F)nc2)c1] | 0.02 |

-continued
| Compound number | Structure | IC 50 in proliferation assay in H460 cells (uM) |
|---|---|---|
| 2895 | 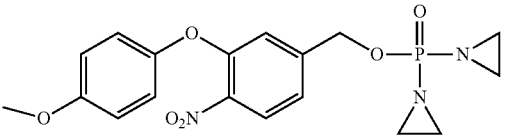 [SMILES: COc1ccc(Oc2cc(COP(=O)(N3CC3)N3CC3)ccc2[N+](=O)[O-])cc1] | 0.004 |
| 2896 | 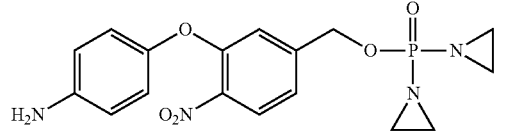 | 0.1 |
| 2898 | 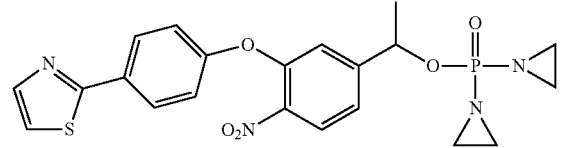 [SMILES: CC(OP(=O)(N1CC1)N1CC1)c1ccc([N+](=O)[O-])c(Oc2ccc(-c3nccs3)cc2)c1] | 0.01 |
| 2899 | 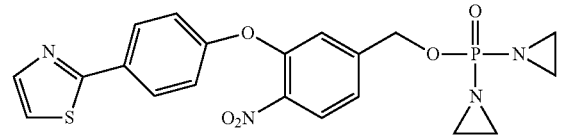 [SMILES: O=[N+]([O-])c1ccc(COP(=O)(N2CC2)N2CC2)cc1Oc1ccc(-c2nccs2)cc1] | 0.004 |
| 2900 | 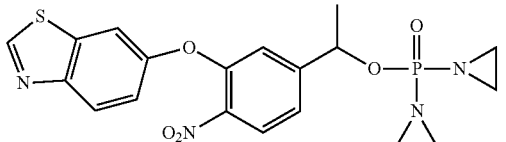 | 0.04 |
| 2901 | 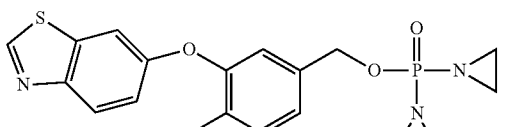 | 0.003 |
| 2902 | 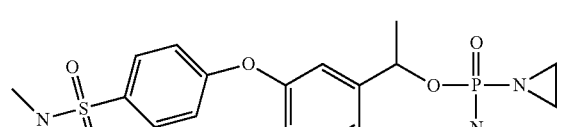 | 0.09 |
| 2903 | 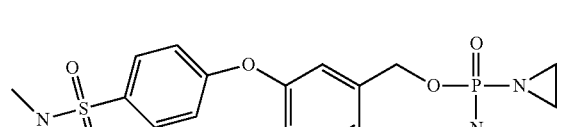 | 0.03 |
| 2904 | 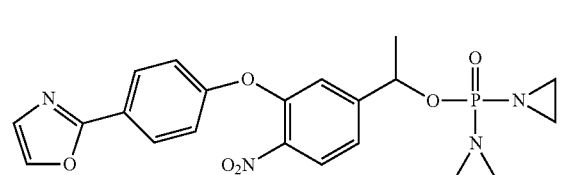 | 0.01 |

-continued

| Compound number | Structure | IC 50 in proliferation assay in H460 cells (uM) |
|---|---|---|
| 2906 | 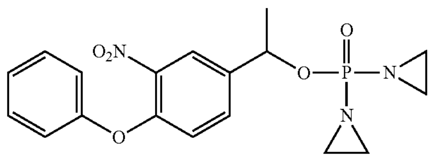 [SMILES: CC(OP(=O)(N1CC1)N1CC1)c1ccc(Oc2ccccc2)c([N+](=O)[O-])c1] | 4 |
| 2908 | 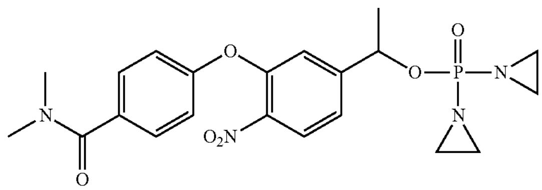 [SMILES: CC(OP(=O)(N1CC1)N1CC1)c1ccc([N+](=O)[O-])c(Oc2ccc(C(=O)N(C)C)cc2)c1] | 0.007 |
| 2909 | 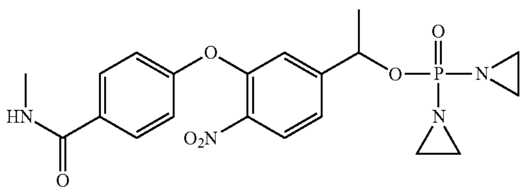 [SMILES: CNC(=O)c1ccc(Oc2cc(C(C)OP(=O)(N3CC3)N3CC3)ccc2[N+](=O)[O-])cc1] | 0.01 |
| 2910 | 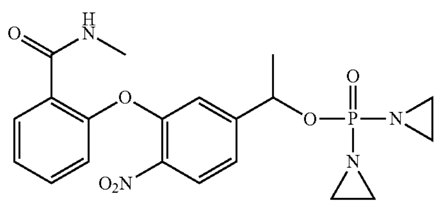 [SMILES: CNC(=O)c1ccccc1Oc1cc(C(C)OP(=O)(N2CC2)N2CC2)ccc1[N+](=O)[O-]] | 3.5 |
| 2911 | 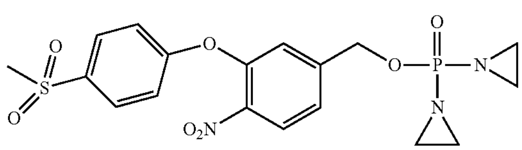 [SMILES: CS(=O)(=O)c1ccc(Oc2cc(COP(=O)(N3CC3)N3CC3)ccc2[N+](=O)[O-])cc1] | 0.008 |
| 2912 | 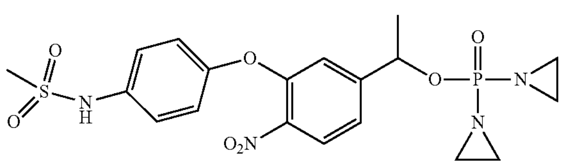 [SMILES: CC(OP(=O)(N1CC1)N1CC1)c1ccc([N+](=O)[O-])c(Oc2ccc(NS(C)(=O)=O)cc2)c1] | 0.04 |
| 2913 | 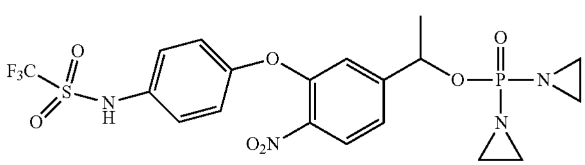 [SMILES: CC(OP(=O)(N1CC1)N1CC1)c1ccc([N+](=O)[O-])c(Oc2ccc(NS(=O)(=O)C(F)(F)F)cc2)c1] | 0.07 |
| 2914 | 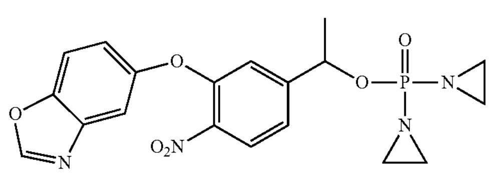 [SMILES: CC(OP(=O)(N1CC1)N1CC1)c1ccc([N+](=O)[O-])c(Oc2ccc3ocnc3c2)c1] | 0.03 |

-continued

| Compound number | Structure | IC 50 in proliferation assay in H460 cells (uM) |
|---|---|---|
| 2915 | 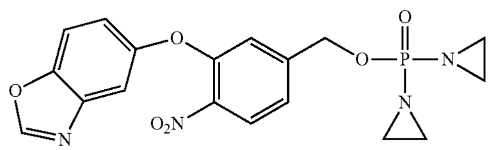 [SMILES: O=[N+]([O-])c1ccc(COP(=O)(N2CC2)N2CC2)cc1Oc1ccc2ocnc2c1] | 0.09 |
| 2916 | 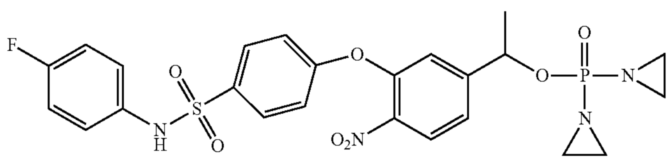 [SMILES: CC(OP(=O)(N1CC1)N1CC1)c1ccc([N+](=O)[O-])c(Oc2ccc(S(=O)(=O)Nc3ccc(F)cc3)cc2)c1] | 0.12 |
| 2917 | 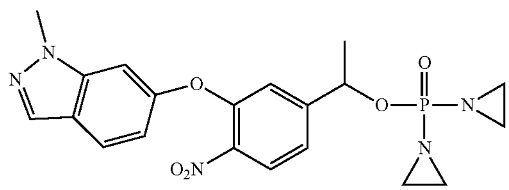 [SMILES: CC(OP(=O)(N1CC1)N1CC1)c1ccc([N+](=O)[O-])c(Oc2ccc3cnn(C)c3c2)c1] | 0.02 |
| 2918 | 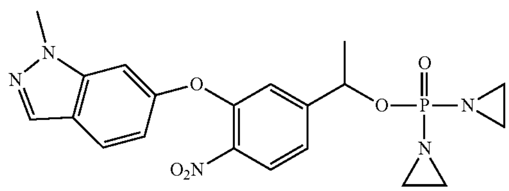 [SMILES: CC(OP(=O)(N1CC1)N1CC1)c1ccc([N+](=O)[O-])c(Oc2ccc3cnn(C)c3c2)c1] | 0.003 |
| 2919 | 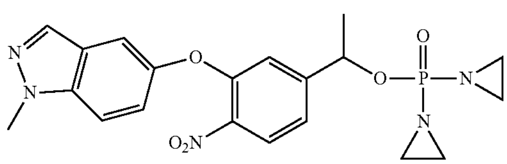 [SMILES: CC(OP(=O)(N1CC1)N1CC1)c1ccc([N+](=O)[O-])c(Oc2ccc3c(cnn3C)c2)c1] | 0.004 |
| 2920 | 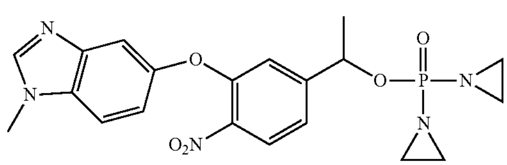 [SMILES: CC(OP(=O)(N1CC1)N1CC1)c1ccc([N+](=O)[O-])c(Oc2ccc3c(c2)ncn3C)c1] | 0.02 |
| 2921 | 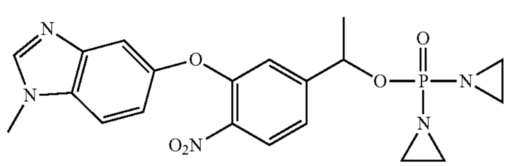 [SMILES: CC(OP(=O)(N1CC1)N1CC1)c1ccc([N+](=O)[O-])c(Oc2ccc3c(c2)ncn3C)c1] | 0.007 |
| 2922 | 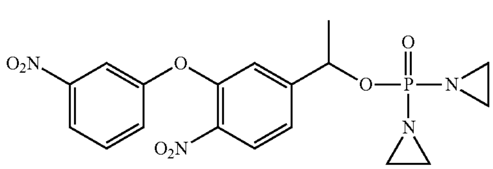 [SMILES: CC(OP(=O)(N1CC1)N1CC1)c1ccc([N+](=O)[O-])c(Oc2cccc([N+](=O)[O-])c2)c1] | 0.003 |

| Compound number | Structure | IC 50 in proliferation assay in H460 cells (uM) |
|---|---|---|
| 2923 | 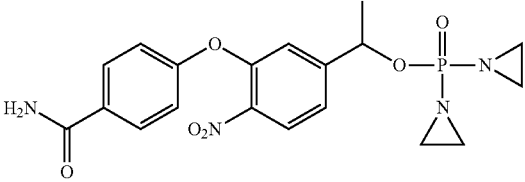 [SMILES: CC(OP(=O)(N1CC1)N1CC1)c1ccc([N+](=O)[O-])c(Oc2ccc(C(N)=O)cc2)c1] | 0.02 |
| 2924 | 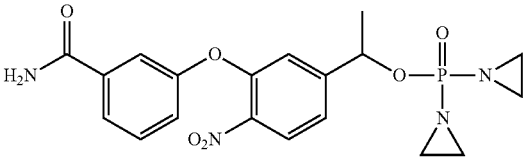 [SMILES: CC(OP(=O)(N1CC1)N1CC1)c1ccc([N+](=O)[O-])c(Oc2cccc(C(N)=O)c2)c1] | 0.1 |
| 2925 | 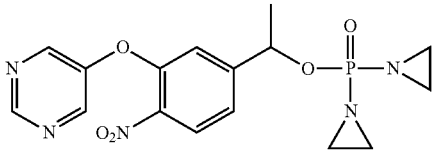 [SMILES: CC(OP(=O)(N1CC1)N1CC1)c1ccc([N+](=O)[O-])c(Oc2cncnc2)c1] | 0.04 |
| 2926 | 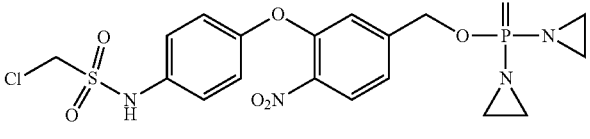 | 0.02 |
| 2927 | 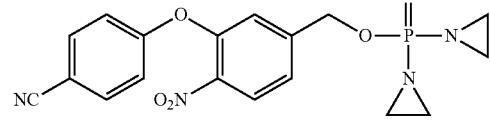 | 0.003 |
| 2928 | 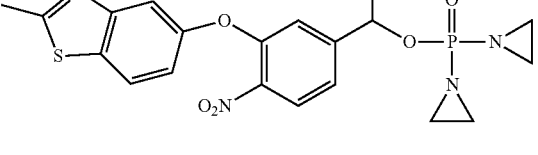 | 0.03 |
| 2929 | 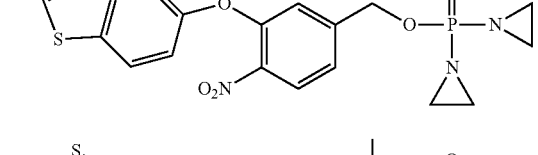 | 0.03 |
| 2930 | 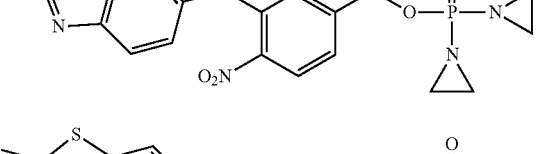 | 0.002 |
| 2931 | 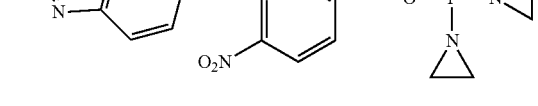 | 0.001 |

-continued

| Compound number | Structure | IC 50 in proliferation assay in H460 cells (uM) |
|---|---|---|
| 2932 | 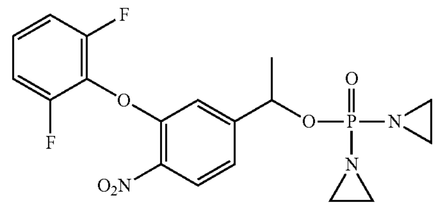 [SMILES: CC(OP(=O)(N1CC1)N1CC1)c1ccc([N+](=O)[O-])c(Oc2c(F)cccc2F)c1] | 0.02 |
| 2933 | 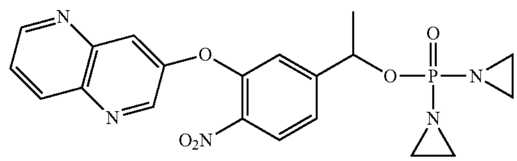 [SMILES: CC(OP(=O)(N1CC1)N1CC1)c1ccc([N+](=O)[O-])c(Oc2cnc3cccnc3c2)c1] | 0.1 |
| 2934 | 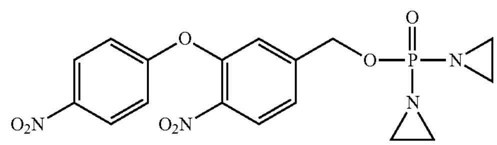 [SMILES: O=[N+]([O-])c1ccc(Oc2cc(COP(=O)(N3CC3)N3CC3)ccc2[N+](=O)[O-])cc1] | 0.003 |
| 2935 | 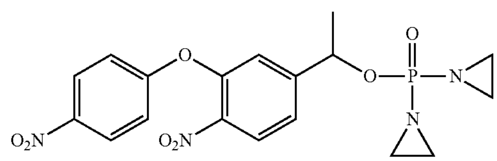 [SMILES: CC(OP(=O)(N1CC1)N1CC1)c1ccc([N+](=O)[O-])c(Oc2ccc([N+](=O)[O-])cc2)c1] | 0.02 |
| 2937 | 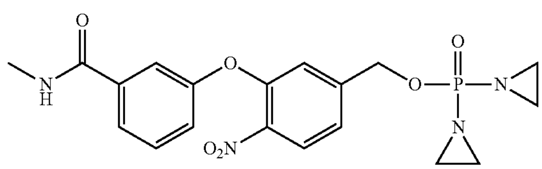 | 0.002 |
| 2938 | 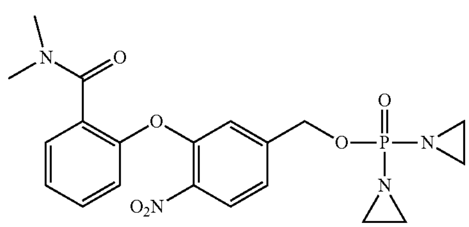 [SMILES: CN(C)C(=O)c1ccccc1Oc1cc(COP(=O)(N2CC2)N2CC2)ccc1[N+](=O)[O-]] | 2.5 |
| 2939 | 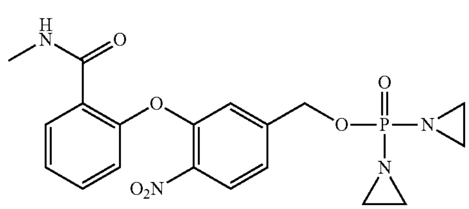 [SMILES: CNC(=O)c1ccccc1Oc1cc(COP(=O)(N2CC2)N2CC2)ccc1[N+](=O)[O-]] | 2.7 |
| 2940 | 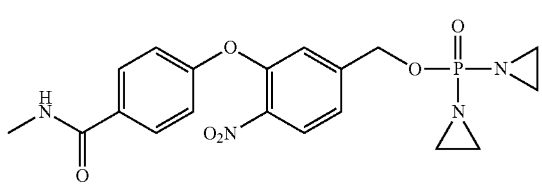 [SMILES: CNC(=O)c1ccc(Oc2cc(COP(=O)(N3CC3)N3CC3)ccc2[N+](=O)[O-])cc1] | 0.005 |

| Compound number | Structure | IC 50 in proliferation assay in H460 cells (uM) |
|---|---|---|
| 2941 | 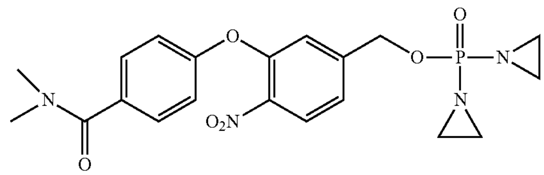 [SMILES: CN(C)C(=O)c1ccc(Oc2cc(COP(=O)(N3CC3)N3CC3)ccc2[N+](=O)[O-])cc1] | 0.004 |
| 2942 | 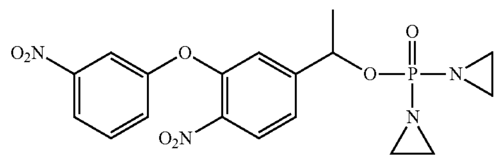 [SMILES: CC(OP(=O)(N1CC1)N1CC1)c1ccc([N+](=O)[O-])c(Oc2cccc([N+](=O)[O-])c2)c1] | 0.02 |
| 2944 | 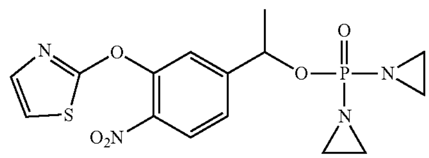 [SMILES: CC(OP(=O)(N1CC1)N1CC1)c1ccc([N+](=O)[O-])c(Oc2nccs2)c1] | >5 |
| 2945 | 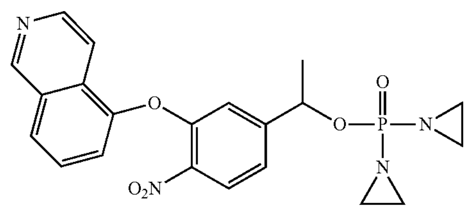 [SMILES: CC(OP(=O)(N1CC1)N1CC1)c1ccc([N+](=O)[O-])c(Oc2cccc3cnccc23)c1] | 0.05 |
| 2946 | 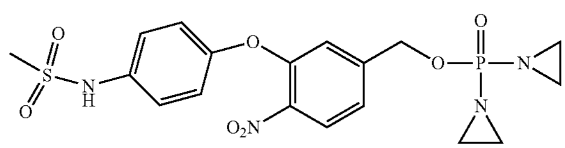 [SMILES: CS(=O)(=O)Nc1ccc(Oc2cc(COP(=O)(N3CC3)N3CC3)ccc2[N+](=O)[O-])cc1] | 0.03 |
| 2947 | 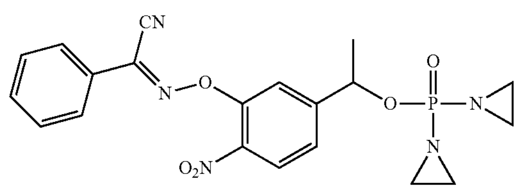 [SMILES: CC(OP(=O)(N1CC1)N1CC1)c1ccc([N+](=O)[O-])c(O/N=C(\C#N)c2ccccc2)c1] | 0.2 |
| 2948 | 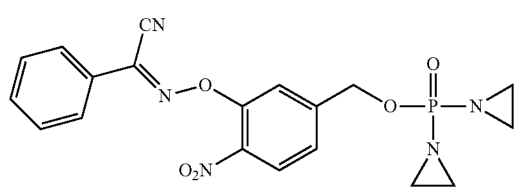 [SMILES: N#C/C(=N\Oc1cc(COP(=O)(N2CC2)N2CC2)ccc1[N+](=O)[O-])c1ccccc1] | 0.04 |
| 2949 | 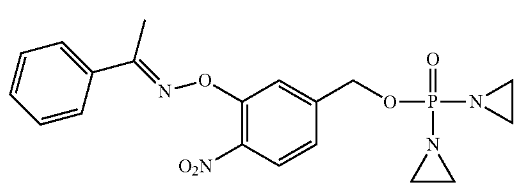 [SMILES: C/C(=N\Oc1cc(COP(=O)(N2CC2)N2CC2)ccc1[N+](=O)[O-])c1ccccc1] | 0.4 |

-continued

| Compound number | Structure | IC 50 in proliferation assay in H460 cells (uM) |
|---|---|---|
| 2950 | 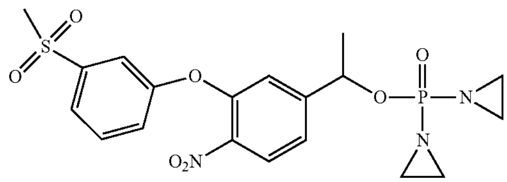 [SMILES: CC(OP(=O)(N1CC1)N1CC1)c1ccc([N+](=O)[O-])c(Oc2cccc(S(C)(=O)=O)c2)c1] | 0.04 |
| 2951 | 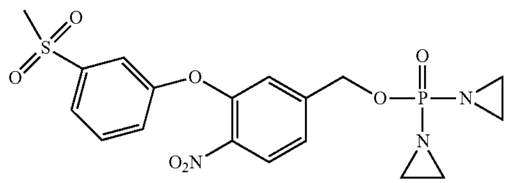 [SMILES: CS(=O)(=O)c1cccc(Oc2cc(COP(=O)(N3CC3)N3CC3)ccc2[N+](=O)[O-])c1] | 0.02 |
| 2952 | 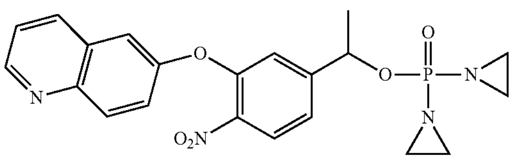 [SMILES: CC(OP(=O)(N1CC1)N1CC1)c1ccc([N+](=O)[O-])c(Oc2ccc3ncccc3c2)c1] | 0.003 |
| 2953 | 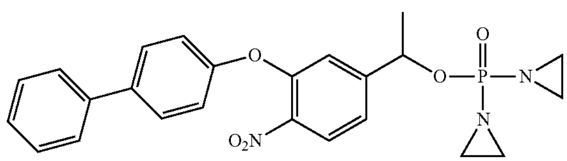 [SMILES: CC(OP(=O)(N1CC1)N1CC1)c1ccc([N+](=O)[O-])c(Oc2ccc(-c3ccccc3)cc2)c1] | 0.005 |
| 2954 | 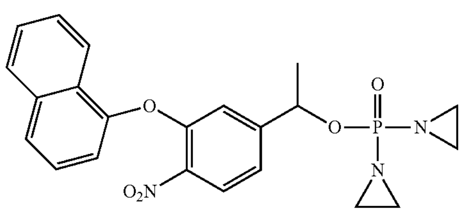 [SMILES: CC(OP(=O)(N1CC1)N1CC1)c1ccc([N+](=O)[O-])c(Oc2cccc3ccccc23)c1] | 0.1 |
| 2955 | 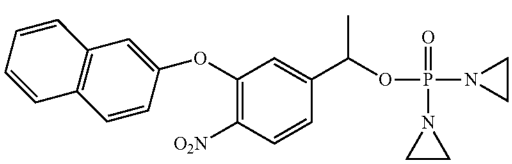 [SMILES: CC(OP(=O)(N1CC1)N1CC1)c1ccc([N+](=O)[O-])c(Oc2ccc3ccccc3c2)c1] | 0.006 |
| 2956 | 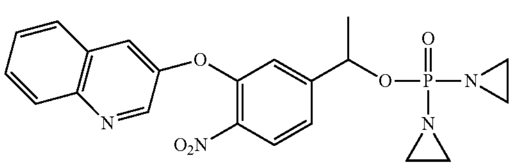 [SMILES: CC(OP(=O)(N1CC1)N1CC1)c1ccc([N+](=O)[O-])c(Oc2cnc3ccccc3c2)c1] | 0.004 |
| 2957 | 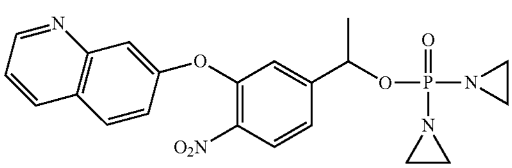 | 0.04 |
| 2958 | 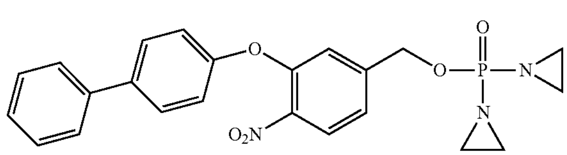 [SMILES: O=[N+]([O-])c1ccc(COP(=O)(N2CC2)N2CC2)cc1Oc1ccc(-c2ccccc2)cc1] | 0.002 |

| Compound number | Structure | IC 50 in proliferation assay in H460 cells (uM) |
|---|---|---|
| 2960 | 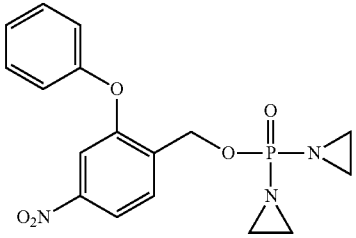 [SMILES: O=[N+]([O-])c1ccc(COP(=O)(N2CC2)N2CC2)c(Oc2ccccc2)c1] | 1.6 |
| 2961 | 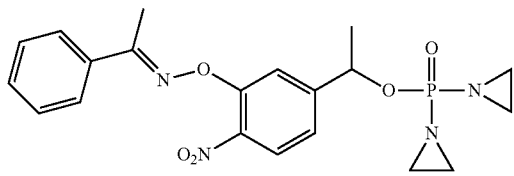 [SMILES: C/C(=N\Oc1cc(C(C)OP(=O)(N2CC2)N2CC2)ccc1[N+](=O)[O-])c1ccccc1] | 2.7 |
| 2966 | 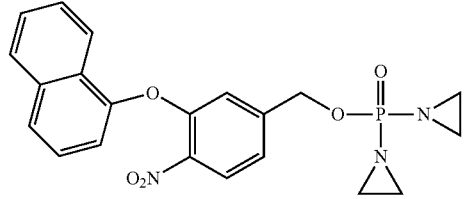 [SMILES: O=[N+]([O-])c1ccc(COP(=O)(N2CC2)N2CC2)cc1Oc1cccc2ccccc12] | 0.2 |
| 2967 | 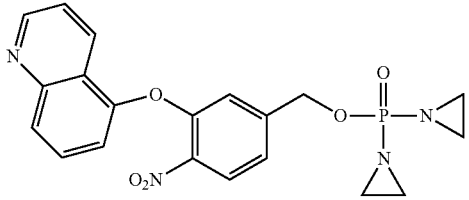 [SMILES: O=[N+]([O-])c1ccc(COP(=O)(N2CC2)N2CC2)cc1Oc1cccc2ncccc12] | 0.1 |
| 2968 | 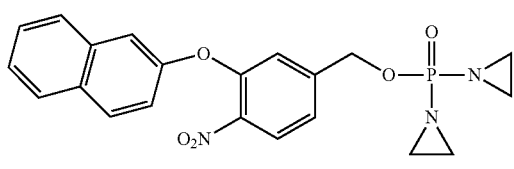 [SMILES: O=[N+]([O-])c1ccc(COP(=O)(N2CC2)N2CC2)cc1Oc1ccc2ccccc2c1] | 0.004 |
| 2969 | 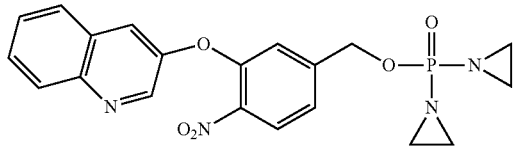 [SMILES: O=[N+]([O-])c1ccc(COP(=O)(N2CC2)N2CC2)cc1Oc1cnc2ccccc2c1] | 0.002 |
| 2970 | 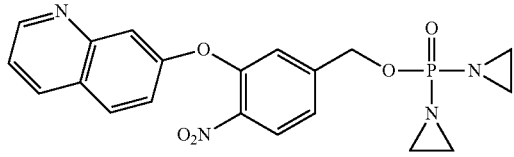 [SMILES: O=[N+]([O-])c1ccc(COP(=O)(N2CC2)N2CC2)cc1Oc1ccc2cccnc2c1] | 0.04 |
| 2971 | 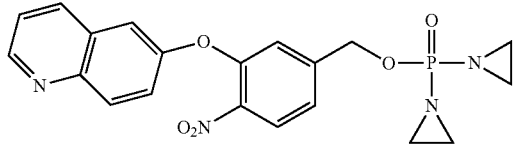 [SMILES: O=[N+]([O-])c1ccc(COP(=O)(N2CC2)N2CC2)cc1Oc1ccc2ncccc2c1] | 0.003 |

-continued

| Compound number | Structure | IC 50 in proliferation assay in H460 cells (uM) |
| --- | --- | --- |
| 2972 | 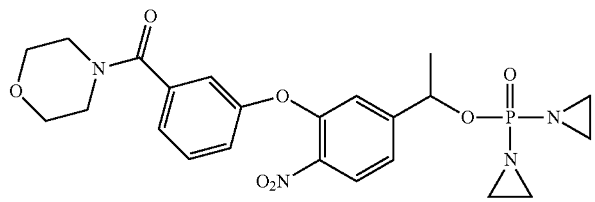 [SMILES: CC(OP(=O)(N1CC1)N1CC1)c1ccc([N+](=O)[O-])c(Oc2cccc(C(=O)N3CCOCC3)c2)c1] | 0.01 |
| 2973 | 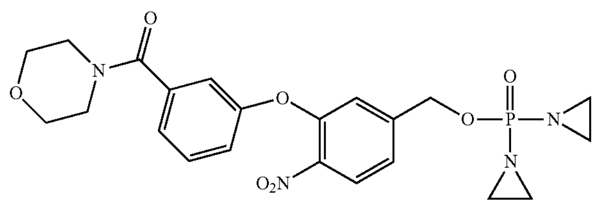 [SMILES: O=C(c1cccc(Oc2cc(COP(=O)(N3CC3)N3CC3)ccc2[N+](=O)[O-])c1)N1CCOCC1] | 0.02 |
| 2974 | 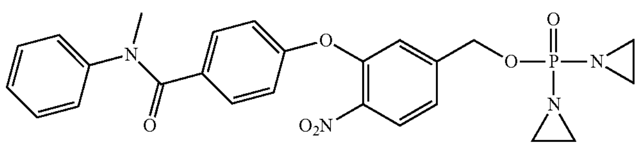 [SMILES: CN(C(=O)c1ccc(Oc2cc(COP(=O)(N3CC3)N3CC3)ccc2[N+](=O)[O-])cc1)c1ccccc1] | 0.001 |
| 2978 | 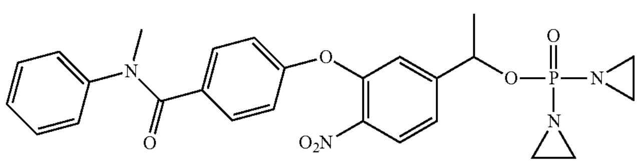 [SMILES: CC(OP(=O)(N1CC1)N1CC1)c1ccc([N+](=O)[O-])c(Oc2ccc(C(=O)N(C)c3ccccc3)cc2)c1] | 0.002 |
| 2980 | 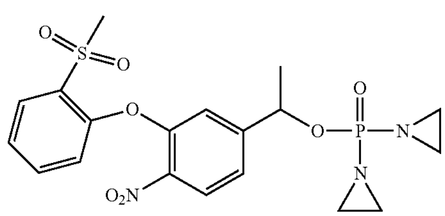 [SMILES: CC(OP(=O)(N1CC1)N1CC1)c1ccc([N+](=O)[O-])c(Oc2ccccc2S(C)(=O)=O)c1] | 3 |
| 2981 | 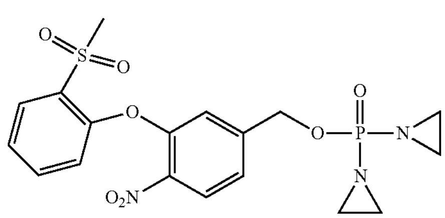 [SMILES: CS(=O)(=O)c1ccccc1Oc1cc(COP(=O)(N2CC2)N2CC2)ccc1[N+](=O)[O-]] | 3.7 |
| 2982 | 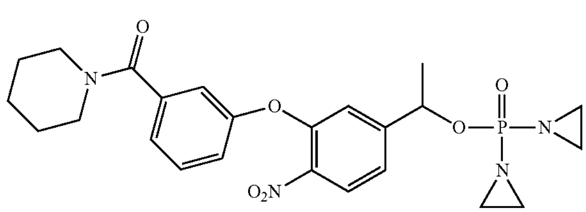 [SMILES: CC(OP(=O)(N1CC1)N1CC1)c1ccc([N+](=O)[O-])c(Oc2cccc(C(=O)N3CCCCC3)c2)c1] | 0.004 |

-continued

| Compound number | Structure | IC 50 in proliferation assay in H460 cells (uM) |
|---|---|---|
| 2983 | 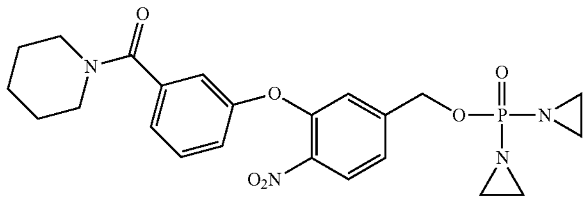 [SMILES: O=C(c1cccc(Oc2cc(COP(=O)(N3CC3)N3CC3)ccc2[N+](=O)[O-])c1)N1CCCCC1] | 0.004 |
| 2984 | 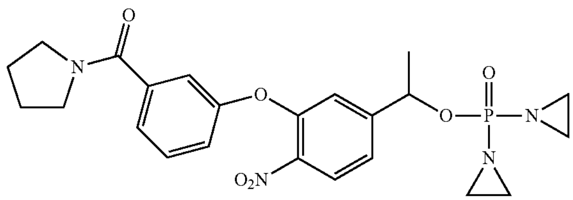 [SMILES: CC(OP(=O)(N1CC1)N1CC1)c1ccc([N+](=O)[O-])c(Oc2cccc(C(=O)N3CCCC3)c2)c1] | 0.005 |
| 2985 | 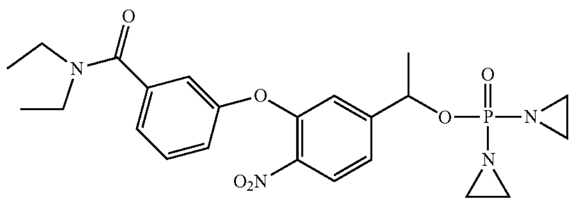 [SMILES: CCN(CC)C(=O)c1cccc(Oc2cc(C(C)OP(=O)(N3CC3)N3CC3)ccc2[N+](=O)[O-])c1] | 0.004 |
| 2991 | 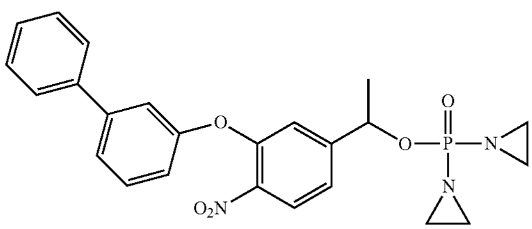 [SMILES: CC(OP(=O)(N1CC1)N1CC1)c1ccc([N+](=O)[O-])c(Oc2cccc(-c3ccccc3)c2)c1] | 0.006 |
| 2992 | 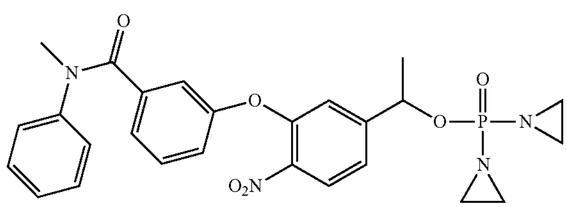 [SMILES: CC(OP(=O)(N1CC1)N1CC1)c1ccc([N+](=O)[O-])c(Oc2cccc(C(=O)N(C)c3ccccc3)c2)c1] | 0.004 |
| 2993 | 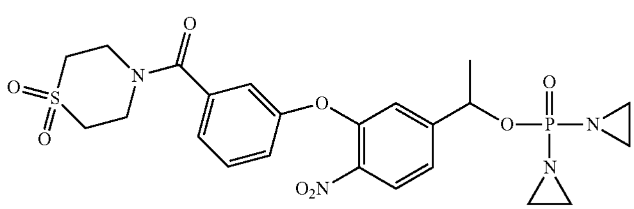 [SMILES: CC(OP(=O)(N1CC1)N1CC1)c1ccc([N+](=O)[O-])c(Oc2cccc(C(=O)N3CCS(=O)(=O)CC3)c2)c1] | 0.02 |
| 3028 | 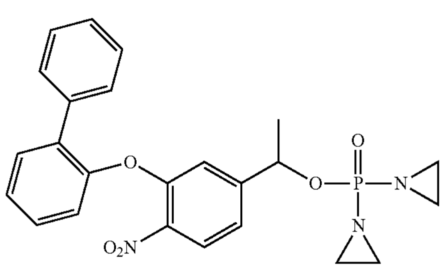 [SMILES: CC(OP(=O)(N1CC1)N1CC1)c1ccc([N+](=O)[O-])c(Oc2ccccc2-c2ccccc2)c1] | 0.7 |

-continued
| Compound number | Structure | IC 50 in proliferation assay in H460 cells (uM) |
|---|---|---|
| 3029 | 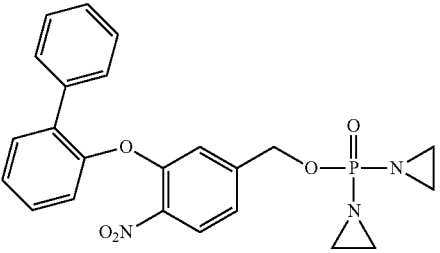 [SMILES: O=[N+]([O-])c1ccc(COP(=O)(N2CC2)N2CC2)cc1Oc1ccccc1-c1ccccc1] | 0.6 |
| 3030 | 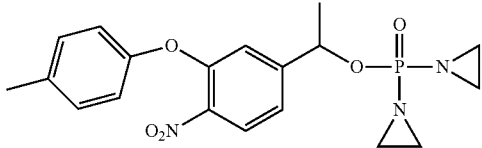 [SMILES: Cc1ccc(Oc2cc(C(C)OP(=O)(N3CC3)N3CC3)ccc2[N+](=O)[O-])cc1] | 0.02 |
| 3031 | 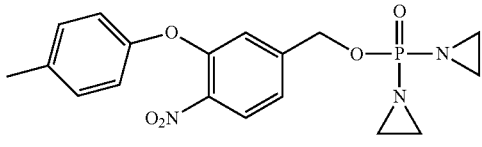 [SMILES: Cc1ccc(Oc2cc(COP(=O)(N3CC3)N3CC3)ccc2[N+](=O)[O-])cc1] | 0.01 |
| 3032 | 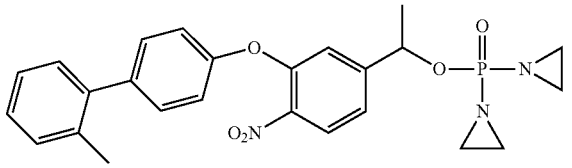 [SMILES: Cc1ccccc1-c1ccc(Oc2cc(C(C)OP(=O)(N3CC3)N3CC3)ccc2[N+](=O)[O-])cc1] | 0.003 |
| 3033 | 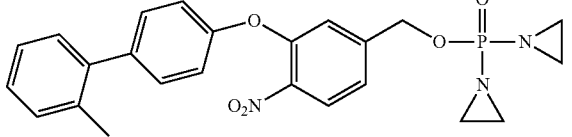 | 0.001 |
| 3034 | 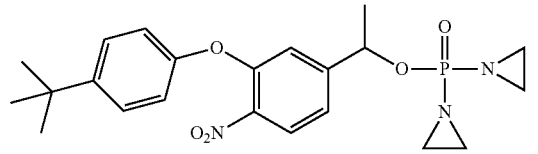 [SMILES: CC(OP(=O)(N1CC1)N1CC1)c1ccc([N+](=O)[O-])c(Oc2ccc(C(C)(C)C)cc2)c1] | 0.008 |
| 3035 | 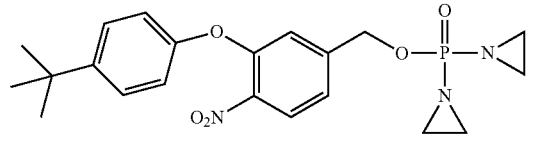 [SMILES: CC(C)(C)c1ccc(Oc2cc(COP(=O)(N3CC3)N3CC3)ccc2[N+](=O)[O-])cc1] | 0.001 |
| 3036 | 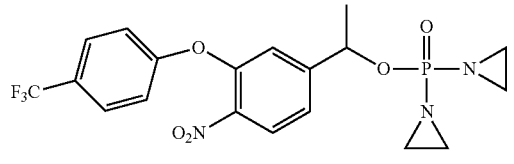 [SMILES: CC(OP(=O)(N1CC1)N1CC1)c1ccc([N+](=O)[O-])c(Oc2ccc(C(F)(F)F)cc2)c1] | 0.004 |
| 3037 | 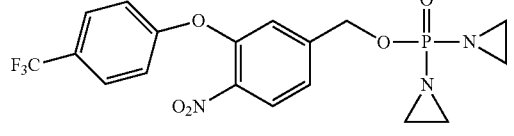 | 0.001 |

-continued
| Compound number | Structure | IC 50 in proliferation assay in H460 cells (uM) |
|---|---|---|
| 3040 | 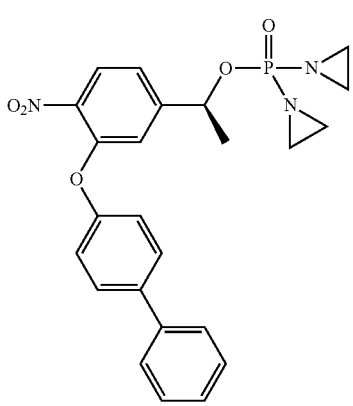 [SMILES: C[C@H](OP(=O)(N1CC1)N1CC1)c1ccc([N+](=O)[O-])c(Oc2ccc(-c3ccccc3)cc2)c1] | 0.004 |
| 3041 | 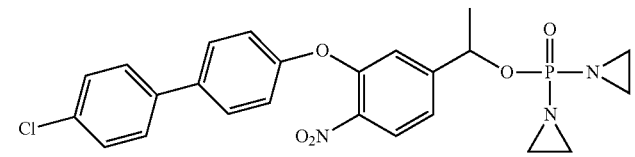 [SMILES: CC(OP(=O)(N1CC1)N1CC1)c1ccc([N+](=O)[O-])c(Oc2ccc(-c3ccc(Cl)cc3)cc2)c1] | 0.05 |
| 3042 | 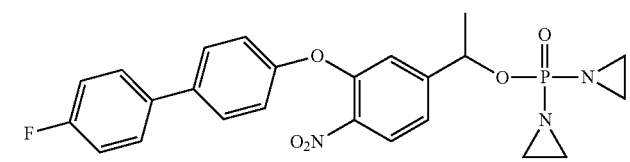 [SMILES: CC(OP(=O)(N1CC1)N1CC1)c1ccc([N+](=O)[O-])c(Oc2ccc(-c3ccc(F)cc3)cc2)c1] | 0.005 |
| 3045 | 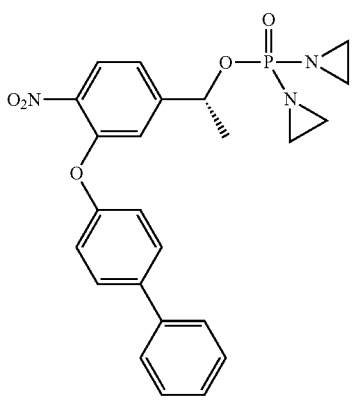 [SMILES: C[C@@H](OP(=O)(N1CC1)N1CC1)c1ccc([N+](=O)[O-])c(Oc2ccc(-c3ccccc3)cc2)c1] | 0.004 |
| 3050 | 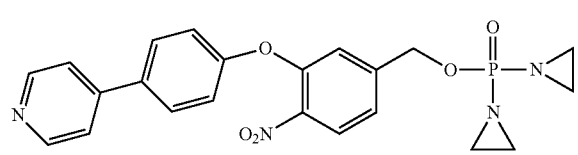 [SMILES: O=[N+]([O-])c1ccc(COP(=O)(N2CC2)N2CC2)cc1Oc1ccc(-c2ccncc2)cc1] | 0.01 |

In another aspect, provided herein is a process of preparing a compound of formula I comprising contacting a compound of formula II:

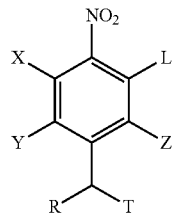

wherein L is a leaving group, with a compound of formula III:

and optionally a base to provide a compound of formula I, wherein the remaining variables are defined in any aspect or embodiment, as above.

In one embodiment, L is halo. In another embodiment, L is F. In another embodiment, $X^{10}$ is O. In another embodiment, Z is hydrogen. In another embodiment, X is hydrogen. In another embodiment, Y is hydrogen. In another embodiment, Y is halo. In one embodiment, the base is a string, non-nucleophilic base, as is well known to the skilled artisan. In one embodiment, the base is a hydride base.

Certain methods for synthesizing compounds provided herein are provided herein. Other methods for synthesizing these and other compounds provided herein will be apparent to the skilled artisan based on the adaptation of, and the replacement of reagents and reactants in, synthetic methods well known to them. See, e.g., Hay et al., *J. Med. Chem.* 2003, 46, 2456-2466 and Hu et al., Bioorganic & Medicinal Chemistry Letters 21 (2011) 3986-3991. Starting materials useful for preparing the compounds provided herein are commercially available or can be prepared following routine methods. The reactions are commonly carried out in an inert solvent and heated if necessary. The skilled artisan will readily appreciate that certain reactions may require the use of a protecting group. Protecting groups are well known to the skilled artisan and described, e.g., in Greene's Protective Groups in Organic Synthesis. Peter G. M. Wuts and Theodora. W. Greene, 4th Edition or a later edition, John Wiley & Sons, Inc., 2007. The reaction products may be separated following routine methods such as crystallization, precipitation, distillation, and/or chromatography. The purity of a compound or an intermediate can be ascertained using well known methods such as $^1$H NMR, HPLC, TLC, and the likes.

EXAMPLES

Example 1-A. Preparation of Compound 7H2768 a. Synthesis of Compound 3

Compound 1 (3 g, 16.2 mmol) was refluxed in $SOCl_2$ (10 mL) with DMF(3 drops) for 3 h and then $SOCl_2$ was removed under vacuum. The residue was diluted with toluene (5 mL) and was used in the following step without further purification.

A mixture of $MgCl_2$ (930 mg, 9.8 mmol), TEA (4.7 mL, 33.4 mmol) and dimethyl malonate (1.9 mL, 16.6 mmol) was stirred at for 1.5 h before the above mentioned toluene solution of Compound 2 was added. The resulting mixture was stirred at RT for another 1.5 h before conc. HCl (4 mL) was added and stirred for 5 minutes. The mixture was extracted with EtOAc (30 mL×3), dried ($Na_2SO_4$), filtered and concentrated under reduced pressure.

To the residue was added 6N HCl (30 mL and the mixture was refluxed overnight.

The mixture was extracted with EtOAc (30 mL×3), dried ($Na_2SO_4$), filtered and concentrated under reduced pressure. The residue was purified via FCC (silica gel, EtOAc/Hexane) to afford Compound 3 as a light yellow solid (1.9 g, 63% yield).

1H NMR (CDCl3, 400 MHz) δ: 8.16 (d, J=8.0 Hz, 1H), 7.86 (t, d=9.2 Hz, 2H), 2.68 (s, 3H).

b. Synthesis of Compound 4

To a mixture of Compound 3 (1.9 g, 10.4 mmol) in MeOH (20 mL) at −10 C. was added $NaBH_4$ (418 mg, 11 mmol) in portions. The mixture was stirred between −10 C. to 0 C. for 20 minutes, diluted with EtOAc (300 mL), washed with sat. NH4Cl aqueous solution, brine, dried ($Na_2SO_4$). Filtered and concentrated under reduced pressure. The residue was purified via FCC (silica gel, EtOAc/Hexane) to afford Compound 4 as a light yellow oil (1.44 g, 75% yield).

1H NMR (CDCl3, 400 MHz) δ: 8.06 (t, J=8.4 Hz, 1H), 7.35 (d, J=11.6 Hz, 1H) 7.30 (d, J=11.6 Hz, 1H), 5.01-4.99 (m, 1H), 1.52 (d, J=6.4 Hz, 3H).

c. Synthesis of Compound 5

To a mixture of Compound 4 (1.44 g, 7.78 mmol), Br-IPM (2.88 g, 9.34 mmol), $PP_3$ (3.06 g, 11.67 mmol) in THF (60 mL) at 0 C. was added DIAD (2.34 g, 11.67 mmol). The mixture was stirred at 0 C. for 1.5 h, concentrated under reduced pressure and purified via FCC (silica gel, EtOAc/Hexane) to afford Compound 5 as a light yellow oil (1.0 g, 27% yield).

1H NMR (CDCl3, 400 MHz) δ: 8.09 (t, J=8.0 Hz, 1H), 8.31 (dd, J=2.4, 13.6 Hz, 2H), 5.52-5.60 (m, 1H), 3.54-3.19 (m, 8H), 1.63 (d, J=6.4 Hz, 3H).

d. Synthesis of Compound 6

A mixture of Compound 5 (1 g, 2.1 mmol) and $Ag_2O$ (3 g) in THF (50 mL) was stirred at 65 C. for 3 h. Filtered and concentrated under reduced pressure. The residue was purified via FCC (silica gel, Acetone/Hexane) to afford Compound 6 as a yellow solid (0.6 g, 90% yield).

$^1$H NMR (CDCl3, 400 MHz) δ: 8.08 (t, J=8.0 Hz, 1H), 7.36 (d, J=11.6 Hz, 1H), 7.31 (d, J=8.4 Hz, 1H), 5.70-5.67 (m, 1H), 2.25-2.08 (m, 8H), 1.64 (d, J=6.4 Hz, 3H).

e. Synthesis of TH 2768

To a mixture of phenol (1.8 g, 19.05 mmol) in DMF (80 mL) at 0 C. was added NaH (60%, 0.76 g, 19.05) in portions. The mixture was stirred at 0 C. for 0.5 h before Compound 6 (3 g, 9.53 mmol) was added and then stirred at 0 C. for 2 h. The mixture was diluted with EtOAc (1 L), washed with brine (100 mL×4), dried over $Na_2SO_4$, filtered, concentrated under reduced pressure and purified via FCC (silica gel, Acetone/Hexane) to afford TH 2768 as a light brown oil (2.3 g, 62% yield).

Purification of TH 2768

TH 2768 as mentioned above was purified via semi-prep HPLC (c18 column, acetonitrile/water). The combined collections were concentrated under reduced pressure to afford a light yellow oil (0.9 g, 81.8% yield) as the final product. Acetonitrile was added in the process as an azeotrope agent to remove water.

1H NMR (CDCl3, 400 MHz) δ: 7.96 (d, J=11.6 Hz, 1H), 7.40 (t, J=10.0 Hz, 2H), 7.21 (t, J=10.0 Hz, 2H), 7.07-7.03 (m, 3H), 5.61-5.48 (m, 1H), 2.22-2.18 (m, 8H), 1.58 (d, J=8.4 Hz, 3H).

Example 1-B. Preparation of TH 2953

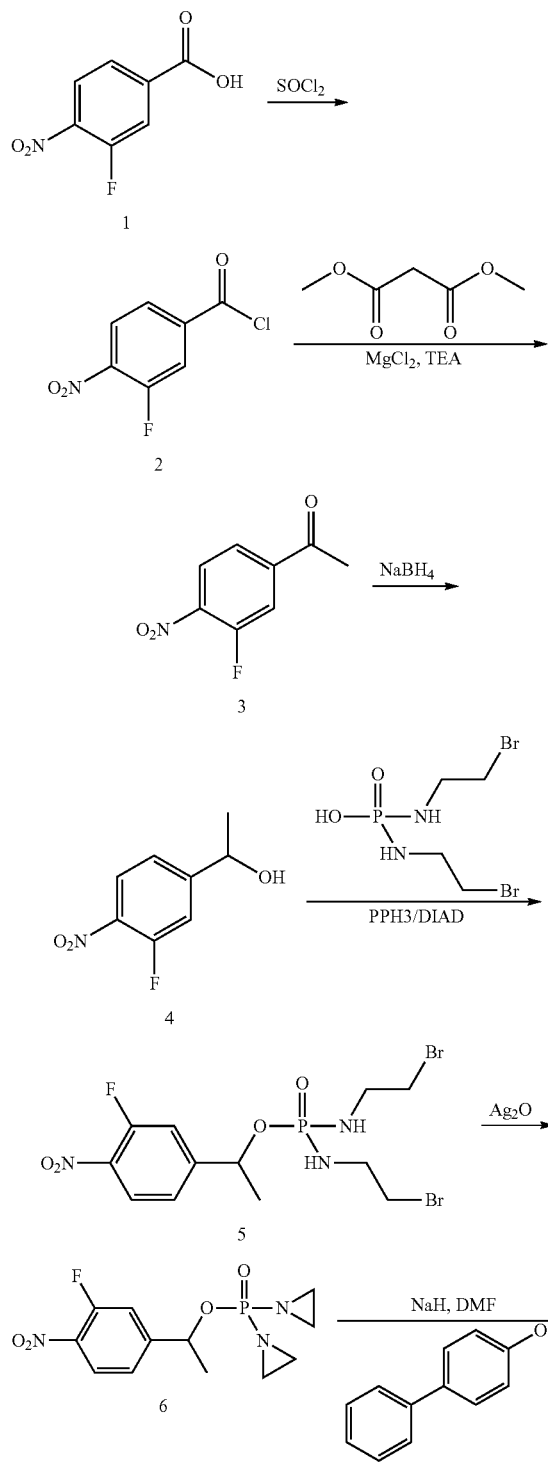

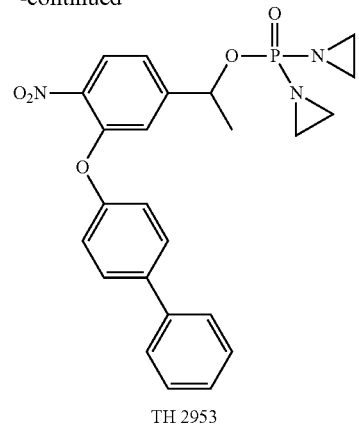

TH 2953

Compounds 3-6 Were Synthesized as Described Above.

a. Synthesis of TH 2953

To a mixture of 4-phenylphenol (2.16 g, 12.7 mmol) in DMF (60 mL) at 0 C. was added NaH (60%, 0.508 g, 12.7 mmol) in portions. The mixture was stirred at 0 C. for 0.5 h before Compound 6 (2 g, 6.35 mmol) was added and then stirred at 0 C. for 2.5 h. The mixture was diluted with EtOAc (500 mL), washed with brine (50 mL×3), dried over Na2SO4, filtered, concentrated under reduced pressure and purified via FCC (silica gel, Acetone/Hexane) to afford TH 2953 as a yellow oil.

Purification of TH 2953

TH 2953 as mentioned above was purified via semi-prep HPLC (C18 column, acetonitrile/water). The combined collections were concentrated under reduced pressure to afford a light yellow oil (1.83 g, 62% yield) as the final product. Acetonitrile was added to the evaporations as an azeotrope agent to remove water.

$^1$HNMR (CDCl3, 400 MHz) δ: 7.99 (d, J=8.4 Hz, 1H), 7.62-7.57 (m, 4H), 7.46 (t, J=7.6 Hz, 2H), 7.37 (t, J=7.2 Hz, 1H), 7.23 (dd, J=8.4, 1.6 Hz, 1H), 7.13-7.11 (m, 3H), 5.61-5.58 (m, 1H), 2.22-1.81 (m, 8H), 1.58 (d, J=6.8 Hz, 3H) ppm.

Example 1-C. Preparation of Compound TH 2870

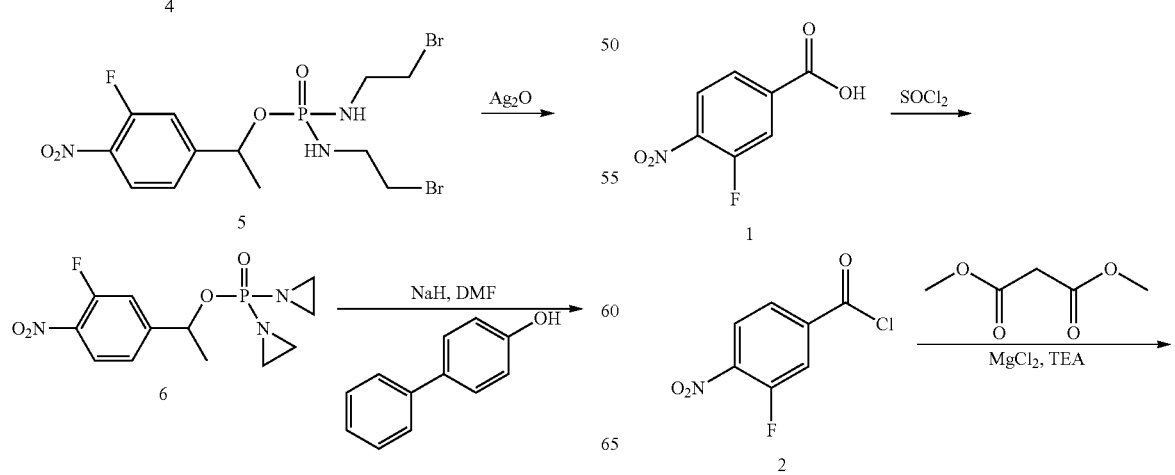

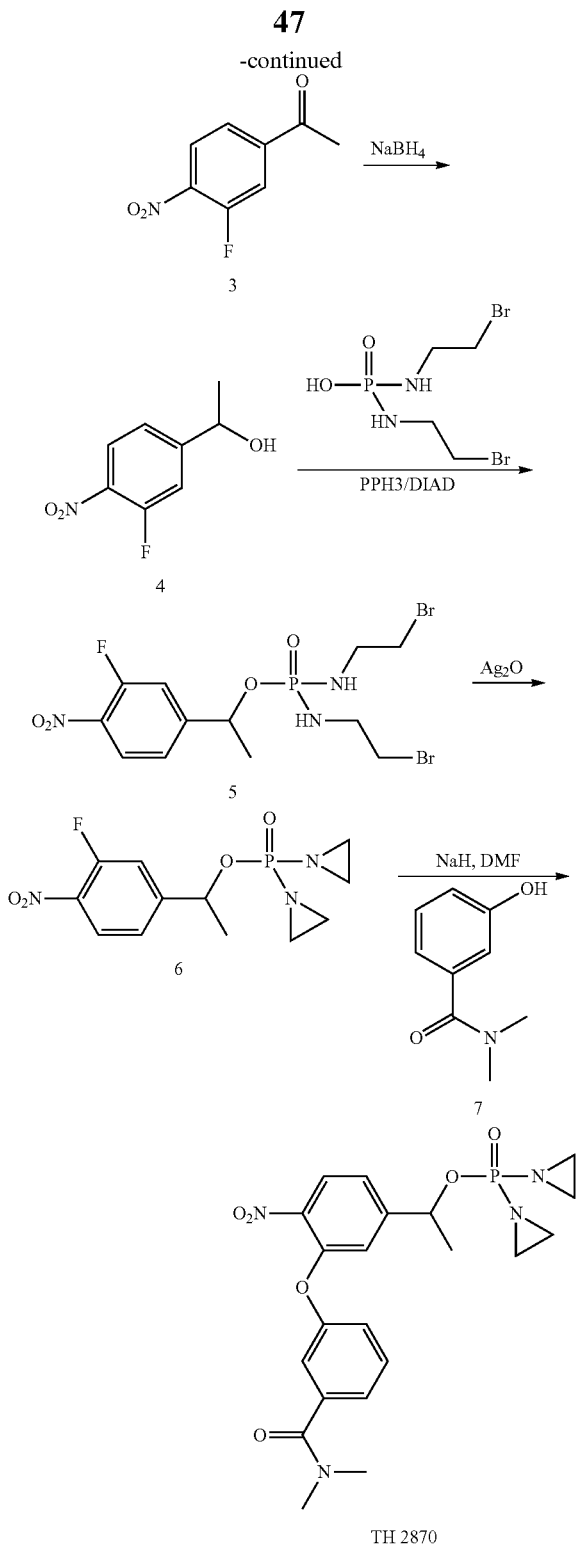

Compounds 2-6 Were Synthesized as Described Below.

a. Synthesis of Compound 3

Compound 1 (3 g, 16.2 mmol) was refluxed in SOCl₂ (10 mL) with DMF (3 drops) for 3 h and then SOCl₂ was removed under vacuum. The residue was diluted with toluene (5 mL) and was used in the following step without further purification.

A mixture of MgCl₂ (930 mg, 9.8 mmol), TEA (4.7 mL, 33.4 mmol) and dimethyl malonate (1.9 mL, 16.6 mmol) was stirred at RT for 1.5 h followed by addition of the above mentioned toluene solution of Compound 2. The resulting mixture was stirred at RT for another 1.5 h then conc. HCl (4 mL) was added and stirred for 5 minutes. The mixture was extracted with EtOAc (30 mL×3), dried (Na₂SO₄), filtered and concentrated under reduced pressure. To the residue was added 6N HCl (30 mL and the mixture was refluxed overnight. The mixture was extracted with EtOAc (30 mL×3), dried (Na₂SO₄), filtered and concentrated under reduced pressure. The residue was purified via FCC (silica gel, EtOAc/Hexane) to afford Compound 3 as a light yellow solid (1.9 g, 63% yield).

¹H NMR (CDCl₃, 400 MHz) δ: 8.16 (d, J=8.0 Hz, 1H), 7.86 (t, d=9.2 Hz, 2H), 2.68 (s, 3H) ppm.

b. Synthesis of Compound 4

To a mixture of Compound 3 (1.9 g, 10.4 mmol) in MeOH (20 mL) at −10 C. was added NaBH₄ (418 mg, 11 mmol) in portions. The mixture was stirred between −10 C. to 0 C. for 20 minutes, diluted with EtOAc (300 mL), washed with sat. NH₄Cl aqueous solution, brine, dried (Na₂SO₄). Filtered and concentrated under reduced pressure. The residue was purified via FCC (silica gel, EtOAc/Hexane) to afford Compound 4 as a light yellow oil (1.44 g, 75% yield).

¹H NMR (CDCl₃, 400 MHz) δ: 8.06 (t, J=8.4 Hz, 1H), 7.35 (d, J=11.6 Hz, 1H), 7.30 (d, J=11.6 Hz, 1H), 5.01-4.99 (m, 1H), 1.52 (d, J=6.4 Hz, 3H) ppm.

c. Synthesis of Compound 5

To a mixture of Compound 4 (1.44 g, 7.78 mmol), Br-IPM (2.88 g, 9.34 mmol), PPh₃ (3.06 g, 11.67 mmol) in THF (60 mL) at 0° C. was added DIAD (2.34 g, 11.67 mmol). The mixture was stirred at 0° C. for 1.5 h, concentrated under reduced pressure and purified via FCC (silica gel, EtOAc/Hexane) to afford Compound 5 as a light yellow oil (1.0 g, 27% yield).

¹H NMR (CDCl₃, 400 MHz) δ: 8.09 (t, J=8.0 Hz, 1H), 8.31 (dd, J=2.4, 13.6 Hz, 2H), 5.52-5.60 (m, 1H), 3.54-3.19 (m, 8H), 1.63 (d, J=6.4 Hz, 3H) ppm.

d. Synthesis of Compound 6

A mixture of Compound 5 (1 g, 2.1 mmol) and Ag₂O (3 g) in THF (50 mL) was stirred at 65° C. for 3 h. Filtered and concentrated under reduced pressure. The residue was purified via FCC (silica gel, Acetone/Hexane) to afford Compound 6 as a yellow solid (0.6 g, 90% yield).

¹HNMR (CDCl₃, 400 MHz) δ: 8.08 (t, J=8.0 Hz, 1H), 7.36 (d, J=11.6 Hz, 1H), 7.31 (d, J=8.4 Hz, 1H), 5.70-5.67 (m, 1H), 2.25-2.08 (m, 8H), 1.64 (d, J=6.4 Hz, 3H) ppm.

e. Preparation of Compound 7

Preparation of Compound 7-2

Ac2O (562 mL, 1.5 eq) was added drop wise to a solution of compound 7-1 (150 g, 1.08 mol) in Pyridine (700 mL) at 0° C., stirred at r.t. for 6 hrs. Evaporated, poured into ice water, filtered, the filter cake was dried to give compound 7-2 as a white solid (150 g, 74% yield).

1H NMR (400 MHz, CDCl3): δ ppm 8.00~7.98 (d, J=7.6 Hz, 1H), 8.03 (s, 1H), 7.83 (s, 1H), 7.51~7.47 (t, J=8.0 Hz, 1H), 7.36~7.34 (dd, J=8.0 Hz 1.2 Hz, 1H), 2.34 (s, 3H).

Preparation of Compound 7-3

To a solution of compound 7-2 (150 g, 833 mmol) in DCM (1500 mL), DMF (15 mL) was added, cooled to 0° C., followed by the addition of oxayl chloride(225 ml 2.50 mol), stirred at r.t. for 4 hrs. Evaporated, the residue was dissolved in DCM (1000 mL) cooled to 0° C. followed by the addition of 2M solution of dimethylamine in THF (900 mL, 1.8 mol), stirred at r.t. for 20 hrs. Quenched with H2O (1500 mL), extracted with DCM (2000 mL×3), evaporated to give crude compound 7-3 as a pale yellow liquid (137 g, 80% yield). ¹H NMR (400 MHz, CDCl3): δ ppm 7.43~7.39 (t, J=8.0 Hz, 1H), 7.29~7.28 (d, J=7.6 Hz, 1H), 7.17~7.13 (m, 2H), 3.00 (s, 6H), 2.32 (s, 3H).

Preparation of Compound 7

To a solution of compound 7-3 (137 g, 661 mmol) in MeOH (1000 mL), K2CO3 (276 g, 2 mol) was added, stirred at r.t. for 5 hrs. Filtered, the filtrate was evaporated. The residue was dissolved in H2O (1000 mL), acidified by 4N HCl to PH6.0, filtered, the filter cake was dried to give compound 7 as a white solid (60 g, 55% yield).

1H NMR (400 MHz, CDCl3): δ ppm 8.25 (s, 1H), 7.19~7.15 (d, J=8.0 Hz, 1H), 6.96~6.95 (t, J=2.0 Hz, 1H), 6.84~6.81 (s, 2H), 3.11 (s, 3H), 2.96 (s, 3H).

f. Synthesis of TH 2870

To a mixture of compound 7 in DMF (60 mL) at 0° C. was added NaH (60%, 0.508 g, 12.7 mmol) in portions. The mixture was stirred at 0 C for 0.5 h before Compound 6 (2 g, 6.35 mmol) was added and then stirred at 0 C. for 2.5 h. The mixture was diluted with EtOAc (500 mL), washed with brine (50 mL×3) dried over Na2SO4, filtered, concentrated under reduced pressure and purified via FCC (silica gel, Acetone/Hexane) to afford TH 2870 as a yellow oil.

Final Purification of TH 2870

TH 2870 as mentioned above was purified via semi-prep HPLC (C18 column, acetonitrile/water). The combined collections were concentrated under reduced pressure to afford a light yellow oil as the final product. Acetonitrile was added to the evaporations as an azeotrope agent to remove water.

¹H NMR (400 MHz, CDCl3): δ ppm 7.98~7.96 (d, J=8.4 Hz, 1H), 7.43~7.39 (m, 1H), 7.27~7.21 (m, 2H), 7.10~7.06 (m, 3H), 5.62~5.55 (m, 1H), 3.09 (s, 3H), 2.97 (s, 3H), 2.19~2.00 (m, 8H), 1.58~1.57 (d, J=6.4 Hz, 3H). MS: m/z 460.8[M+1]+. PLC: 254 nm: 94.8%.

Example 1-D. Alternative Preparation of Compound 2870

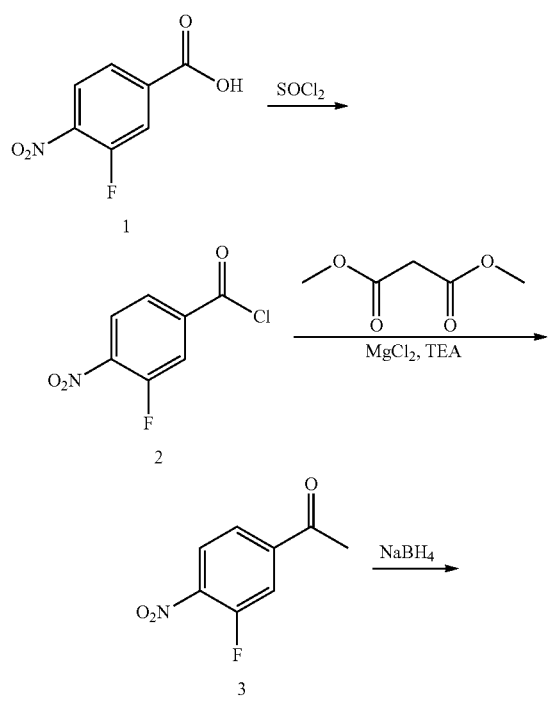

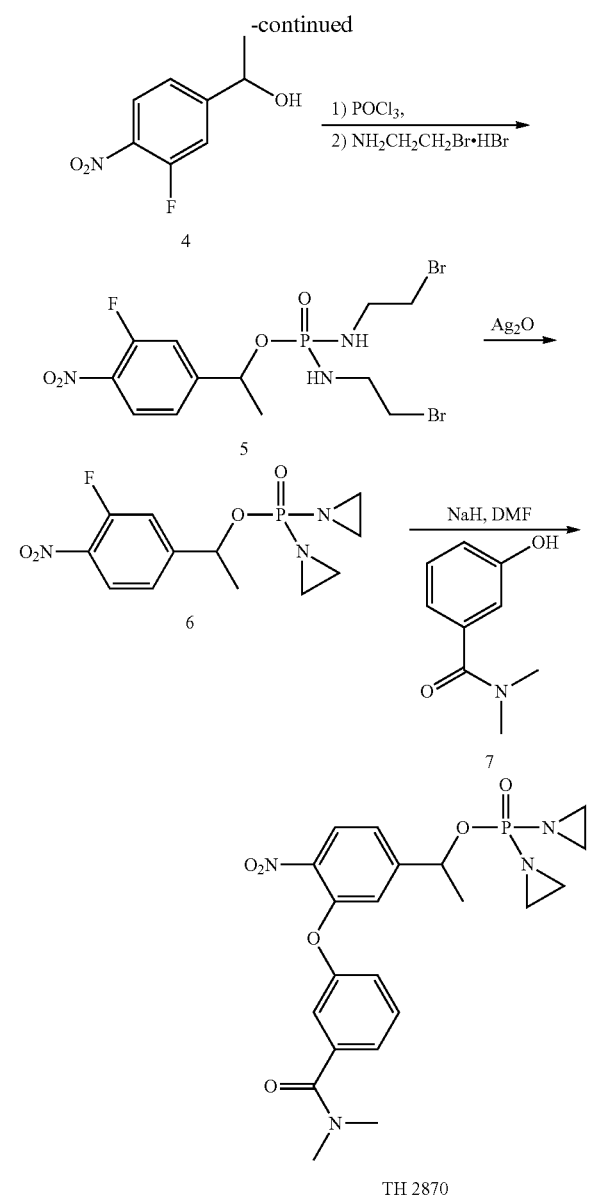

a. Preparation of Compound 3

Compound 1 (200 g, 1.08 mol) was refluxed in SOCl2 (700 mL) with DMF (10 ml) for 3 hrs and then SOCl2 was removed under vacuum. The residue was diluted with toluene (400 mL) and was used in the following step without further purification.

A mixture of MgCl2 (103 g, 1.08 mol), TEA (500 mL, 3.60 mol) and dimethyl malonate (145 g, 1.1 mol) was stirred at RT for 1.5 hrs before the above mentioned toluene solution of compound 2 was added drop wise. The resulting mixture was stirred at RT for another 1.5 hrs. Washed with H2O (2 L), extracted with EtOAc (2 L×5), evaporated, 4N HCl was added until PH6.0 and stirred for 5 minutes. The mixture was extracted with EtOAc (2 L×5), evaporated.

To the residue was added 6N HCl (1500 mL) and the mixture was refluxed overnight.

The mixture was extracted with EtOAc (2 L×5), concentrated, purified by silica gel column (petroleum ether:EtOAc=20:1) to give compound 3 as a yellow solid (80 g, 41% yield).

b. Preparation of Compound 4

To a mixture of compound 3 (150 g, 824 mol) in MeOH (2 L) at −10° C. was added NaBH4 (31.2 g, 824 mmol) in portions. The mixture was stirred between −10° C. to 0° C. for 20 minutes, diluted with EtOAc (5 L), washed with sat. NH4Cl aqueous solution, brine, dried over Na2SO4, concentrated. The residue was purified by silica gel column (petroleum ether:EtOAc=5:1) to give compound 4 as a yellow oil (90 g, 60% yield).

c. Preparation of Compound 5

To a solution of POCl3 (2 ml, 21.6 mmol) in DCM (20 ml) was added compound 4 (2 g, 10.8 mmol), then TEA (3.6 ml, 27 mmol) in DCM (10 ml) was added at −40° C. under N2, stirred at −40° C. for 5 hrs. Then 2-Bromoethylamine (17.6 g, 86.8 mmol) was added, TEA (12 ml, 86.8 mmol) in DCM (40 ml) was added slowly into above solution at −40° C., stirred for 0.5 h. K2CO3 (10%, 10.4 g, 100 ml) was added, stirred at r.t. for 5 mins. Extracted with L) CM (300 ml×3), evaporated, purified by silica gel column (EtOAc) to give compound 5 as a yellow oil(2.3 g, 43% yield).

d. Preparation of Compound 6

A mixture of compound 5 (4 g, 8.42 mmol) and Ag2O (5.85 g, 25.26 mmol) in THF (40 ml) was stirred at 65° C. for 3 hrs, filtered and concentrated. The residue was purified by silica gel column (EtOAc) to give compound 6 as a yellow oil (2.3 g, 87% yield).

e. Preparation of Compound TH 2870

To a solution of Compound 7 (1.81 g, 10.95 mmol) in DMF (10 ml), NaH (60%, 438 mg, 1095 mmol) was added at 0° C., stirred for 10 mins, then compound 6 (2.3, 7.3 mmol) in DMF (10 ml) was added, stirred at 0° C. for 30 mins.

Quenched with H2O, extracted with EtOAc (100 ml×5), washed with H2O (150 ml), brine, evaporated, purified by silica gel column (DCM:MeOH=40:1) to give compound TH 2870 as a yellow oil (2.3 g, 69% yield).

Example 1-E. Preparation of TH 2846, TH 2850, TH 2852, TH 2854, TH 2860-TH 2866, TH 2871-TH 2878, TH 2880, TH 2881, TH 2883, TH 2887-TH 2893, TH 2895, TH 2896, TH 2898-TH 2900, TH 2902, TH 2903, TH 2904, TH 2906, TH 2908, TH 2909, TH 2911-TH 2923, TH 2925-TH 2935, TH 2937-TH 2942, TH 2944, TH 2949, TH 2952-TH 2958, TH 2960, TH 2961, TH 2966-TH 2971, TH 2974, TH 2978, TH 2980, TH 2981, TH 2984, TH 2985, TH 2991-TH 2993, TH 3028-TH 3037, TH 3041, TH 3042 and TH 3050

Compounds TH 2846, TB 2850, TH 2852, TB 2854, TH 2860-TH 2866, TH 2871-TH 2878, TH 2880 TH 2881, TH 2883, TH 2887-TH 2893, TH 2895, TH 2896, TH 2898-TH 2900, TH 2902, TH 2903, TH 2904, TH 2906, TH 2908, TH 2909, TH 2911-TH 2923, TH 2925-TH 2935, TH 2937-TH 2942, TH 2944, TH 2949, TH 2952-TH 2958, TH 2960, TH 2961, TH 2966-TH 2971, TH 2974, TH 2978, TH 2980, TH 2981, TH 2984, TH 2985, TH 2991-TH 2993, TH 3028-TH 3037, TH 3041, TH 3042 and TH 3050 were synthesized using similar synthetic procedures as described above.

TH 2846

Starting with (140 mg). 1H NMR (CDCl3) δ: 1.57 (d, 3H), 1.92-2.20 (M, 8H), 5.85 (m, 1H), 7.0 (d, 7.15-7.26 (dd, 2H), 7.38 (t, 2H), 7.70 (d, 1H). 31.2.

TH 2850

1H NMR (CDCl3, 400 MHz) δ 7.95 (d, 1H), 7.39 (t, 2H), 7.05 (d 2H), 7.99 (s, 1H), 5.10 (d, 2H), 2.18-2.12. (m, 8H).

TH 2852

1H NMR (CDCl3, 400 MHz) δ 8.40 (bs, 1H), 8.0 (bs, 1H), 7.35 bs, 4H), 7.20 (s, 1H), 5.12 (bs, 1H), 2.18-2.12 (bs, 8H), 1.6 (hd, 3H).

1H NMR (CDCl3, 400 MHz) δ: 8.00 (d, J=8.4 Hz, 1H), 7.89 (d, J=8.2 Hz, 1H), 7.67 (s, 1H), J=7.8 Hz, 1H), 7.27-7.25 (m, 2H), 7.06 (d, J=1.2 Hz, 1H), 5.62-5.60 (m, 1H), 4.37 (q, J=6.8 Hz, 2H), 2.18-2.00 (m, 8H), 1.39 (t, J=6.8 Hz, 3H).

TH 2855

1H NMR (CDCl3, 400 MHz) δ: 7.96 (d, J=8.4 Hz, 1H), 7.27-7.05 (m, 3H), 6.60-6.32 (m, 3H), 5.64-5.59 (m, 1H), 2.96 (s, 6H), 2.20-2.00 (m, 8H), 1.58 (d, J=6.4 Hz, 3H).

TH 2860

Starting with 4-Chloro-phenol (60 mg). 1H NMR (CDCl3) δ: 1.58 (d, 3H), 1.97-2.25 (m, 8H), 5.59 (m, 1H), 6.95 (d, 2H), 7.05 (d, 1H), 7.24 (dd, 1H), 7.35 (d, 2H), 7.96 (d, 1H). 31PNMR (CDCl3) δ: 31.3.

TH 2861

Starting with 4-Fluorophenol (50 mg). 1H NMR (CDCl3) δ: 1.55 (d, 3H), 1.92-2.15 (m, 8H), 5.54 (m, 1H), 6.95-7.16 (m, 5H), 7.20 (dd, 1H), 7.94 (d, 1H). 31PNMR (CDCl3) δ: 31.3.

TH 2862

Starting with 2-Chloro-phenol (60 mg). 1H NMR (CDCl3) δ: 1.55 (d, 3H), 1.95-2.20 (m, 8H), 5.56 (m, 1H), 6.81 (d, 1H), 7.10 (d, 1H), 7.13-7.35 (m, 3H), 7.50 (dd, 1H), 8.0 (d, 1H), 31PNMR (CDCl3) δ: 31.3.

TH 2863

Starting with 2,4-difluoro-phenol (60 mg). 1H NMR (CDCl3) δ: 1.54 (d, 3H), 1.91-2.20 (m, 8H), 5.56 (m, 1H), 6.85-7.05 (m, 3H), 7.10-7.22 (m, 2H), 7.98 (d, 31PNMR (CDCl3) δ: 31.4.

TH 2864

Starting with 2,4-dichloro-phenol (73 mg). 1H NMR (CDCl3) δ: 1.55 (d, 3H), 1.95-2.25 (m, 8H), 5.57 (m, 1H), 6.86 (d, 1H), 7.0 (d, 1H), 7.20-7.30 (m, 2H), 7.48 (dd, 1H), 7.99 (d, 1H). 31PNMR (CDCl3) δ: 31.4.

Starting with 2-Fluorophenol (50 mg). 1H NMR (CDCl3) δ: 1.54 (d, 3H), 1.95-2.25 (m, 8H), 5.57 (m, 1H), 6.89 (d, 1H), 7.10-7.30 (m, 5H), 7.99 (d, 1H). 31PNMR (CDCl3) δ: 31.3.

TH 2866

Starting 1,3-benzodioxol-5-ol (62 mg), 1H NMR (CDCl3) δ: 1.55 (d, 3H), 1.95-2.25 (m, 8H), 5.56 (m, 1H), 6.0 (s, 2H), 6.50 (dd, 1H), 6.59 (d, 1H), 6.78 (d, 1H), 6.99 (s, 1H), 7.13 (d, 1H), 7.96 (d, 1H). 31PNMR (CDCl3) δ: 31.3.

TH 2871

Starting with 3-(trifluoromethyl)phenol (73 mg). 1H NMR (CDCl3) δ: 1.58 (d, 3H), 1.95-2.25 (m, 8H), 5.59 (m, 1H), 7.10 (s, 1H), 7.15-7.50 (m, 5H), 7.99 (d, 1H). 31PNMR (CDCl3) δ: 31.5.

TH 2872

Starting with 4-Cyanophenol (54 mg) 1H NMR (CDCl3) δ: 1.58 (d, 3H), 1.97-2.25 (m, 8H), 5.65 (m, 1H), 7.0 (d, 2H), 7.21 (d, 1H), 7.38 (dd, 1H), 7.65 (d, 2H), 8.05 (d, 1H). 31PNMR (CDCl3) δ: 31.5.

TH 2873

Starting material with 4-Methoxyphenol(56 mg). 1H NMR (CDCl3) δ: 1.54 (d, 3H), 1.95-2.19 (m, 8H), 3.83 (s, 3H), 5.53 (m, 1H), 6.90-6.97 (m, 3H), 7.0 (d, 2H), 7.13 (dd, 1H), 7.93 (d, 1H). 31PNMR (CDCl3) δ: 31.2.

TH 2874

1H NMR (CDCl3, 400 MHz) δ 8.13-8.11 (dd, 1H), 7.61 (t, 1H), 7.44 (m, 2H), 7.30 (m, 1H), 6.62-6.59 (dd, 1H), 6.33 (t, 1H), 5.72 (m, 1H), 2.18-2.12 (m, 8H), 1.60 (m, 3H).

TH 2875
1H NMR (CDCl3, 400 MHz) δ 8.08 (d, 1H), 7.65 (d, 1H), 7.49 (s, 1H), 7.3 (m, 2H), 6.63 (d, 1H), 6.30 (t, 1H), 5.12 (d, 2H), 2.18-2.12 (m, 8H).
TH 2876
1H NMR (CDCl3, 400 MHz) δ 8.08 (d, 2H), 7.40-7.00 (m, 5H), 5.12 (d, 2H), 4.40 (q, 2H), 2.18-2.12 (m, 8H), 1.60 (t, 3H).
1H NMR (CDCl3, 400 MHz) δ 8.43-8.38 (m, 2H), 7.98 (d, 2H), 7.35 (d, 1H), 7.33-7.25 (m, 2H), 7.07 (s, 1H), 5.12 (d, 1H), 2.18-2.12 (m, 8H).
TH 2878
1H NMR (CDCl3) δ 8.25 (d, 1H), 7.7 (d, 1H), 7.65 (s, 1H), 7.52-7.46 (m, 1H), 7.3-7.1 (m, 2H), 6.7-6.6 (m, 1H), 5.8-5.7 (m, 1H), 2.25-2 (m, 8H), 1.67 (d, 3H).
TH 2880
1H NMR (CDCl3) δ 8.05-7.8 (m, 3H), 7.4-7.3 (m, 2H), 7.1-6.9 (m, 2H), 5.75 (s, 2H), 5.7-5.5 (m, 1H), 2.2-1.9 (m, 8H), 1.56 (d, 3H).
TH 2881
1H NMR (CDCl3) δ 8.05-7.7 (m, 3H), 7.4-7.3 (m, 1H), 7.2 (s, 1H), 7.2-7.0 (m, 2H), 5.7-5.5 (m, 1H), 2.72 (s, 6H), 2.2-1.9 (n, 8H), 1.61 (d, 3H).
TH 2883
Starting with 4-(methylsulfonyl)phenol (78 mg). 1H NMR (CDCl3) δ: 1.62 (d, 3H), 2.01-2.22 (m, 8H), 3.07 (s, 3H), 5.67 (m, 1H), 7.09 (d, 2H), 7.24 (s, 1H), 7.38 (d, 1H), 7.92 (d, 2H), 8.05 (d, 1H). 31PNMR (CDCl3) δ: 31.5.
TH 2884
1HNMR (CDCl3, 400 MHz) δ: 8.00-7.93 (m, 1H), 7.62-7.60 (m, 1H), 7.48-7.34 (m, 2H), 7.20-7.11 (n, 2H), 5.52-5.48 (m, 1H), 2.94-2.83 (m, 3H), 2.14-1.95 (m, 8H), 1.55 (d, J=6.4 Hz, 3H).
TH 2885
1HNMR (CDCl3, 400 MHz) δ: 7.94-7.91 (n, 1H), 7.41-7.36 (m, 2H), 7.28-7.18 (m, 2H), 7.01-6.94 (m, 2H), 5.56-5.53 (m, 1H), 3.06-2.88 (m, 6H), 2.15-1.96 (m, 8H), 1.54-1.52 (m, 3H).
TH 2887
1H NMR (CDCl3, 400 MHz) δ 8.08 (d, 1H), 7.92 (d, 2H), 7.35 (d, 1H), 7.20 (s, 1H), 7.07 (d, 2H), 5.12 (d, 1H), 2.18-2.12 (m, 8H).
1H NMR (CDCl3, 400 MHz) δ 7.94 (d, 1H) 7.15 (d, 1H), 6.98 (s, 1H), 6.74 (d, 1H), 6.61 (d, 1H), 6.54 (dd, 1H), 6.02 (s, 2H), 5.12 (d, 1H), 2.18-2.12 (m, 8H).
TH 2889
1H NMR (CDCl3, 400 MHz) δ 7.98 (d, 1H), 7.42 (t, 1H), 7.23 (m, 2H), 7.07 (m, 3H), 5.13 (d, 2H), 3.09 (s, 3H), 2.98 (s, 3H), 2.18-2.12 (m, 8H).
TH 2890
1H NMR (CDCl3, 400 MHz) δ 8.31 (d, 1H), 8.00 (d, 1H), 7.35-7.23 (m, 3H), 7.01 (s, 1H), 5.14 (d, 2H), 2.58 (s, 3H), 2.20-2.10 (m, 8H).
TH 2891
1H NMR (CDCl3, 400 MHz) δ 8.27 (d, 1H), 7.97 (d, 1H), 7.35-7.23 (m, 3H), 7.01 (s, 1H), 5.80 (m, 1H), 2.56 (s, 3H), 2.20-2.10 (m, 8H), 1.55 (d, 3H).
TH 2892
1H NMR (CDCl3, 400 MHz) δ 7.97 (d, 1H), 7.94 (bs, 1H), 7.48 (m, 1H), 7.26 (d, 1H), 7.03 (s, 1H), 6.97-6.94 (dd, 1H), 5.14 (d, 2H), 2.20-2.10 (m, 8H).
TH 2893
1H NMR (CDCl3, 400 MHz) δ 7.97 (d, 1H), 7.94 (bs, 1H), 7.51 (m, 1H), 7.29 (d, 1H), 7.08 (s, 1H), 6.97-6.94 9dd, 1H), 5.60 (m, 1H), 2.20-2.10 (m, 8H), 1.66-1.58 (d, 3H).

TH 2895
1H NMR (CDCl3) δ: 1.95-2.18 (m, 8H), 3.83 (s, 3H), 5.09 (d, 2H), 6.84 (d, 2H), 6.89-6.96 (m, 3H), 7.13 (d, 1H), 7.94 (d, 1H). 31PNMR (CDCl3) δ: 32.2.
TH 2896
1H NMR (CDCl3) δ: 2.05-2.22 (m, 8H), 5.08 (d, 6.71 (d, 2H), 6.88-6.93 (m, 3H), 7.10 (d, 1H), 7.93 (d, 1H). 31PNMR (CDCl3) δ: 32.2.
TH 2898
1H NMR (CDCl3) δ 8.05-7.98 (m, 3H), 7.87 (d, 1H), 7.34 (d, 1H), 7.28 (d, 1H), 7.15 (s, 1H), 7.1 (d, 2H), 5.7-5.5 (m, 1H) 2.2-1.98 (m, 8H), 1.61 (d, 3H).
1H NMR (CDCl3) δ 8.1-7.9 (m, 3H), 7.85 (d, 1H), 7.33 (dd, 1H), 7.28 (dd, 1H), 7.15-7.05 (m, 3H), 5.16 (d, 2H), 2.2-2.08 (m, 8H).
TH 2900
1H NMR (CDCl3) δ 8.98 (s, 1H), 8.15 (d, 1H), 8.01 (d, 1H), 7.61 (s, 1H), 7.3-7.2 (m, 2H) 7.09 (s, 1H), 5.65-5.55 (m, 1H), 2.2-1.96 (m, 8H), 1.58 (d, 3H).
TH 2902
1H NMR (CDCl3) δ 8.05 (d, 1H), 7.87 (d, 2H), 7.37 (d, 1H), 7.23 (s, 1H), 7.09 (d, 2H), 5.7-5.5 (m, 1H), 4.5-4.3 (m, 1H), 2.7 (d, 3H), 2.22-2.02 (m, 8H), 1.63 (d, 3H).
TH 2903
1H NMR (CDCl3) δ 8.05 (d, 1H), 7.87 (d, 2H), 7.36 (d, 1H), 7.21 (s, 1H), 7.09 (d, 2H), 5.21 (d, 2H), 4.5-4.4 (m, 1H), 2.7 (d, 3H), 2.25-2.1 (m, 8H).
TH 2904
1H NMR (CDCl3) δ 8.06 (d, 8.01 (d, 1H), 7.71 (s, 1H), 7.3-7.2 (m, 2H), 7.15 (s, 1H), 7.09 (d, 2H), 5.65-5.55 (m, 1H), 2.2-1.96 (m, 8H), 1.59 (d, 3H).
TH 2906
1H NMR (CDCl3, 400 MHz) δ: 8.01 (s, 1H), 7.53 (d, J=8.8 Hz, 1H), 7.40 (t, J=8.0 Hz, 2H), 7.21 (t, J=7.2 Hz, 1H), 7.06 (d, J=8.0 Hz, 2H), 7.01 (d, J=8.4 Hz, 1H) 5.18 (d, J=8.0 Hz, 2H), 2.25-2.17 (m, 8H).
TH 2908
NMR (CDCl3, 400 MHz) δ: 8.00 (d, J=8.4 Hz, 1H), 7.47 (d, J=8.4 Hz, 2H), 7.28 (d, J=8.0 Hz, 1H), 7.11 (s, 1H), 7.05 (d, J=8.4 Hz, 2H), 5.60-5.58 (m, 1H), 3.12 (s, 3H), 3.04 (s, 3H), 2.19-2.02 (m, 8H), 1.58 (d, J=6.4 Hz, 3H).
TH 2909
1H NMR (CDCl3, 400 MHz) δ: 8.00 (d, J=8.4 Hz, 1H), 7.78 (d, J=8.4 Hz, 2H), 7.30-7.28 (m, 1H), 7.14 (s, 1H), 7.04 (d, J=4.8 Hz, 2H), 6.14 (br, 1H), 5.64-5.59 (m, 1H), 3.02 (d, J=5.6 Hz, 3H), 2.20-2.00 (m, 8H), 1.58 (d, J=6.4 Hz, 3H).
Starting with 4-(methylsufonyl)phenol (120 mg). 1H NMR (CDCl3) δ: 2.10-2.28 (m, 8H), 3.08 (s, 3H), 5.23 (d, 2H), 7.11 (d, 2H), 7.24 (s, 1H), 7.39 (d, 2H), 7.93 (d, 2H), 8.07 (d, 1H). 31PNMR (CDCl3) δ: 32.3.
TH 2912
Starting with N-(4-Hydroxy-phenyl)-methanesulfonamide (115 mg). 1H NMR (CDCl3) δ: 1.58 (d, 3H), 2.0-2.22 (m, 8H), 3.0 (s, 3H), 5.58 (m, 1H), 6.97-7.11 (m, 3H), 7.22-7.32 (m, 3H), 7.94 (d, 1H). 31PNMR (CDCl3) δ: 31.5.
TH 2913
Starting with N-(4-Hydroxy-phenyl)-trifluoromethane-sulfonamide (145 mg). 1H NMR (CDCl3) δ: 1.57 (d, 3H), 2.01-2.22 (m, 8H), 2.97 (s, 3H), 5.58 (m, 1H), 6.98 (d, 2H), 7.04 (s, 1H), 7.23 (d, 1H), 7.29 (d, 2H), 7.97 (d, 1H) 31PNMR (CDCl3) δ: 31.5. 19FNMR (CDCl3) δ: −76.0.
TH 2914
1H NMR (CDCl3) δ 8.15 (s, 1H), 8.0 (d, 1H), 7.62 (d, 1H), 7.43 (d, 1H), 7.23 (d, 1H), 7.18 (dd, 1H), 7.03 (s, 1H), 5.62-5.52 (m, 1H), 2.2-1.96 (m, 8H), 1.56 (d, 3H).

TH 2915
1H NMR (CDCl3) δ 8.16 (s, 1H), 8.01 (d, 1H), 7.63 (d, 1H), 7.46 (d, 1H) 7.23 (d, 1H), 7.26-7.16 (m, 2H), 7.02 (s, 1H), 5.14 (d, 1H), 2.2-1.96 (m, 8H).
TH 2916
1H NMR (CDCl3) δ 8.04 (d, 1H), 7.68 (d, 2H), 7.36 (d, 1H), 7.19 (s, 1H), 7.08-7.02 (m, 2H), 7.02-6.94 (m, 4H), 5.7-5.62 (m, 1H), 2.22-2.02 (m, 8H), 1.61 (d, 3H).
TH 2917
1H NMR (CDCl3) δ 8.0 (d, 1H), 7.98 (s, 1H), 7.73 (d, 1H), 7.23 (d, 1H), 7.05 (d, 2H), 6.9 (d, 1H), 5.62-5.52 (m, 1H), 4.03 (3, 3H), 2.2-1.94 (m, 8H), 1.56 (d, 3H).
TH 2918
1H NMR (CDCl3) δ 8.01 (d, 1H), 7.99 (s, 1H), 7.74 (d, 1H), 7.23 (d, 1H), 7.04 (s, 2H), 6.91 (dd, 1H), 5.62-5.13 (d, 2H), 4.03 (3, 3H), 2.2-2.02 (m, 8H).
1H NMR (CDCl3) δ 7.97 (d, 1H), 7.95 (s, 1H), 7.45 (d, 1H), 7.37 (d, 1H), 7.22-7.14 (m, 2H), 6.94 (s, 1H), 5.62-5.5 (m, 1H), 4.12 (3, 3H), 2.16-1.92 (m, 8H), 1.53 (d, 3H).
TH 2920
1H NMR (CDCl3) δ 7.98 (d, 1H), 7.92 (s, 1H), 7.47 (d, 1H), 7.42 (d, 1H), 7.22-7.1 (m, 2H), 6.95 (s, 1H), 5.6-5.4 (m, 1H), 3.9 (3, 3H), 2.16-1.94 (m, 8H), 1.52 (d, 3H).
TH 2921
1H NMR (CDCl3) δ 7.98 (d, 1H), 7.92 (s, 1H), 7.48 (s, 1H), 7.43 (d, 1H), 7.22-7.1 (m, 2H), 6.94 (s, 1H), 5.6-5.07 (d, 2H), 3.9 (3, 3H), 2.16-2.05 (m, 8H), 1.52 (d, 3H).
TH 2922
1H NMR (CDCl3, 400 MHz) δ 8.08 (d, 1H), 8.04 (dd, 1H), 7.77 (t, 1H), 7.57 (t, 1H), 7.40 (dd, 2H), 7.21 (s, 1H), 5.22 (d, 2H), 2.23-2.12 (m, 8H).
TH2923
1H NMR (CDCl3, 400 MHz) δ: 8.01 (d, J=8.4 Hz, 1H), 7.84 (d, J=8.0 Hz, 2H), 7.31 (dd, J=1.2, 8.4 Hz, 1H), 7.14 (d, J=1.2 Hz, 1H), 7.02 (d, J=8.4 Hz, 2H), 5.62-5.60 (m, 1H), 2.18-2.00 (m, 8H), 1.58 (d, J=6.8 Hz, 3H).
TH 2924
1H NMR (CDCl3, 400 MHz) δ: 8.0 (d, J=8.4 Hz, 1H), 7.68 (d, J=8.0 Hz, 1H), 7.50 (t, J=8.4 Hz, 1H), 7.41 (s, 1H), 7.34-7.20 (m, 3H), 5.60-5.50 (m, 1H), 2.20-2.10 (m, 4H), 2.04-1.96 (m, 4H), 1.59 (d, J=6.8 Hz, 3H).
TH 2925
1H NMR (CDCl3, 400 MHz) δ: 9.05 (s, 1H), 8.50 (s, 2H), 8.07 (d, J=8.4 Hz, 1H), 7.40 (d, J=8.8 Hz, 1H), 7.23 (s, 1H), 5.64-5.60 (m, 1H), 2.22-2.05 (m, 8H), 1.60 (d, J=6.4 Hz, 3H).
TH 2926
Starting with N-(4-Hydroxy-phenyl)-chloromethanesulfonamide (133 mg). 1H NMR (CDCl3) δ: 2.08-2.21 (m, 8H), 4.48 (s, 2H), 5.16 (d, 2H), 7.03 (d, 2H), 7.07 (s, 1H), 7.24 (d, 1H), 7.34 (d, 2H), 7.98 (d, 1H). 31PNMR (CDCl3) δ: 32.1.
Starting with 4-Cyanophenol (144 mg). 1H NMR (CDCl3) δ: 2.12-2.28 (m, 8H), 5.23 (d, 2H), 7.05 (d, 2H), 7.23 (s, 1H), 7.39 (d, 1H), 7.67 (d, 2H), 8.07 (d, 1H). 31PNMR (CDCl3) δ: 32.3.
TH 2928
1H NMR (CDCl3) δ 8.01 (d, 1H), 7.82 (d, 1H), 7.55 (d, 1H), 7.25 (dd, 7.15 (dd, 1H), 7.08 (s, 1H), 5.6-5.4 (m, 1H), 2.85 (3, 3H), 2.18-1.94 (m, 8H), 1.56 (d, 3H).
TH 2929
1H NMR (CDCl3) δ 8.01 (d, 1H), 7.83 (d, 1H), 7.57 (d, 1H), 7.24 (dd, 1H), 7.15 (dd, 1H), 7.06 (s, 1H), 5.6-5.12 (d, 2H), 2.85 (3, 3H), 2.2-2.05 (m, 8H).

TH 2930
1H NMR (CDCl3) δ 7.99 (d, 1H), 7.95 (d, 1H), 7.5 (d, 1H), 7.23 (d, 1H), 7.18 (dd, 1H), 7.05 (s, 1H), 5.6-5.5 (m, 1H), 2.85 (3, 3H), 2.18-1.94 (m, 8H), 1.57 (d, 3H).
TH 2931
1H NMR (CDCl3) δ 7.99 (d, 1H), 7.94 (d, 1H), 7.5 (d, 1H), 7.26-7.16 (m, 2H), 7.02 (s, 1H), 5.12 (d, 2H), 2.84 (3, 3H), 2.16-2.02 (m, 8H).
TH 2932
1H NMR (CDCl3) δ 8.02 (d, 1H), 7.28-7.16 (m, 2H), 7.07 (t, 2H), 6.87 (s, 1H), 5.6-5.5 (m, 1H), 2.18-1.96 (m, 8H), 1.55 (d, 3H).
TH 2933
1H NMR (CDCl3) δ 8.94 (d, 1H), 8.92-8.88 (m, 1H), 8.42 (d, 1H), 8.12 (d, 1H), 7.63 (d, 1H), 7.58 (dd, 1H), 7.43 (dd, 1H), 7.34 (d, 1H), 5.7-5.6 (m, 1H), 2.22-2.0 (m, 8H), 1.63 (d, 3H).
TH 2934
1H NMR (CDCl3, 400 MHz) δ 8.25-8.23 (m, 2H), 8.08 (d, 2H), 7.43-7.40 (dm, 1H), 7.27 (m, 1H), 7.20-7.07 (dd, 2H), 5.24 (d, 2H), 2.21-2.15 (m, 8H).
TH 2935
1H NMR (CDCl3, 400 MHz) δ 7.42-7.40 (dd, 2H), 7.42 (d, 2H), 7.27 (s, 1H), 7.20-7.07 (2, 2H), 5.66 (m, 1H), 2.18-2.12 (m, 8H), 1.6 (d, 3H).
1H NMR (CDCl3, 400 MHz) δ 7.98 (d, 1H), 7.61 (d, 1H), 7.43 (t, 1H), 7.34 (m, 1H), 7.21 (d, 2H), 7.14 (s, 1H), 6.95 (bs, 1H), 5.17 (d, 2H), 2.9 (2, 3H), 2.18-2.12 (m, 8H).
TH 2938
1H NMR (CDCl3, 400 MHz) δ 7.93 (d, 1H), 7.40 (m, 2H), 7.23 (m, 1H), 7.19 (d, 1H), 6.98 (d, 1H), 6.98 (s, 1H), 5.08 (d, 2H), 3.02 (s, 3H), 2.94 (s, 3H), 2.18-2.12 (m, 8H).
TH 2939
1H NMR (CDCl3, 400 MHz) δ 7.91 (m, 1H), 7.44 (m, 2H), 7.18 (m, 2H), 6.86 (d, 2H), 6.60 (bs, 1H), 5.18 (d, 2H), 3.47 (s, 3H), 2.18-2.12 (m, 8H).
TH 2940
1H NMR (CDCl3, 400 MHz) δ 8.02 (d, 1H), 7.79 (d, 2H), 7.29 (d, J=7.12 (s, 1H), 7.04 (d, 2H), 6.25 (s, 1H), 5.20 (d, 2H), 3.02 (d, 3H), 2.18-2.12 (m, 8H).
TH 2941
1H NMR (CDCl3, 400 MHz) δ 8.02 (s, 1H), 8.00 (d, 1H), 7.47 (d, 2H), 7.08 (s, 1H), 7.47 (d, 2H), 5.15 (d, 2H), 3.11 (s, 3H), 3.03 (s, 3H), 2.18-2.12 (m, 8H).
TH 2942
1H NMR (CDCl3, 400 MHz) δ 8.08 (d, 1H), 8.03 (d, 1H), 7.75 (t, 1H), 7.38 (dt, 1H), 7.22 (dd, 2H), 7.21 (s, 1H), 5.68 (m, 1H), 2.23-2.12 (m, 8H), 1.54 (d, 3H).
TH 2944
1H NMR (CDCl3, 400 MHz) δ: 8.11 (d, J=10.8 Hz, 1H), 7.61 (dd, J=2.0, 11.2 Hz, 1H), 7.50 (d, J=1.6 Hz, 1H), 6.74 (d, J=7.6 Hz, 1H) 6.38 (d, J=7.2 Hz, 1H), 5.76-5.71 (m, 1H), 2.27-2.07 (m, 8H), 1.66 (d, J=10.4H, 3H).
TH 2945
1H NMR (CDCl3, 400 MHz) δ: 9.00 (s, 1H) 8.05 (d, J=11.21H), 7.98 (d, J=11.2 Hz, 1H), 7.66 (t, J=10.4 Hz, 1H), 7.48 (dd, J=6.0, 11.6 Hz, 1H) 7.30 (d, J=1.6 Hz, 1H), 7.26 (s, 1H), 7.06 (d, J=1.6 Hz, 1H), 7.0 (d, J=10.4 Hz, 1H), 5.62-5.60 (m 1H), 2.18-1.92 (m, 8H), 1.57 (d, J=8.8 Hz, 3H).
Starting with N-(4-Hydroxy-phenyl)-methanesulfonamide (150 mg). 1H NMR (CDCl3) δ: 2.11-2.20 (m, 8H), 3.02 (s, 3H), 5.16 (d, 2H), 7.02-7.07 (m, 3H), 7.23-7.29 (m, 3H), 7.99 (d, 1H). 31PNMR (CDCl3) δ: 32.1.
TH 2947
Starting with 3-Hydroxy-2-phenylacrylonitrile (88 mg), 1H NMR (CDCl3) δ: 1.66 (d, 3H), 2.03-2.26 (m, 8H), 5.65 (m, 1H), 7.29 (dd, 1H), 7.47-7.62 (m, 3H), 7.72 (d, 1H), 7.90 (d, 2H), 8.01 (d, 1H).

TH 2948
Starting with 2-Hydroxyimino-2-phenylacetonitrile (97 mg). 1H NMR (CDCl3) δ: 2.18-2.32 (m, 8H), 5.28 (m, 1H), 7.31 (dd, 1H), 7.51-7.64 (m, 3H), 7.76 (d, 1H), 7.94 (d, 2H), 8.06 (d, 1H).
TH 2949
Starting with 1-Phenyl-1-ethanone oxime (90 mg). 1H NMR (CDCl3) δ: 2.16-2.29 (m, 8H), 2.59 (s, 3H), 5.22 (d, 1H), 7.13 (dd, 1H), 7.44-7.49 (m, 3H), 7.75-7.79 (m, 2H), 7.91 (d, 1H), 8.02 (d. 1H).
TH 2950
Starting with 3-(methylsulfonyl)phenol (78 mg). $^1$HNMR (CDCl$_3$) δ: 1.60 (d, 3H), 2.01-2.20 (m, 8H), 3.06 (s, 3H), 5.63 (m, 1H), 7.18 (S, 1H), 7.30-7.38 (m, 2H), 7.50 (S, 1H), 7.59 (t, 1H), 7.73 (d, 8.02 (d, 1H). $^{31}$PNMR (CDCl$_3$) δ: 31.5.
TH 2951
Starting with 3-(methylsulfonyl)phenol (113 mg) $^1$HNMR (CDCl$_3$) δ: 2.12-2.22 (m, 8H), 3.07 (s, 3H), 5.19 (d, 2H), 7.18 (S, 1H), 7.30-7.38 (m, 2H), 7.52 (s, 1H), 7.60 (t, 1H), 7.73 (d, 1H), 8.04 (d, 1H). $^{31}$PNMR (CDCl$_3$) δ: 32.3.
TH 2952
1H NMR (CDCl3, 400 MHz) δ: 8.98 (s, 1H), 8.15 (d, J=12.0 Hz, 1H), 8.05 (t, J=8.8 Hz, 2H), 7.50 (dd, J=3.6, 12.0 Hz, 1H), 7.42 (dd, J=6.0, 11.6 Hz, 1H), 7.32 (dd, J=3.6, 8.0 Hz, 1H), 7.28-7.27 (m, 2H), 7.15 (d, J=2.0 Hz, 1H), 5.62-5.60 (m, 1H), 2.20-1.94 (m, 8H), 1.59 (d, J=8.8 Hz, 3H).

1H NMR (CDCl3, 400 MHz) δ: 8.11 (d, J=10.0 Hz, 1H0, 9.02 (d, J=11.2 Hz, 1H), 7.91 (d, J=10.0 Hz, 1H), 7.74 (d, J=11.2 Hz, 1H), 7.60-7.50 (m, 1H), 7.45 (t, J=10.0 Hz, 1H), 7.18 (dd, J=2.0, 11.6 Hz, 1H), 7.06 (d, J=10.0 Hz, 1H), 6.90 (d, J=1.2 Hz, 1H), 5.60-5.50 (m, 1H), 2.12-2.00 (m, 4H), 1.96-1.84 (m, 4H), 1.52 (d, J=8.8 Hz, 3H).
TH 2955
1H NMR (CDCl3, 400 MHz) δ: 8.02 (d, J=11.2 Hz, 1H), 7.92-7.85 (m, 2H), 7.74 (d, J=10.0 Hz, 1H), 7.54-7.46 (m, 2H), 7.49 (d, J=3.2 Hz, 1H), 7.30-7.22 (m, 2H), 7.08 (d, J=1.6 Hz, 1H), 5.62-5.46 (m, 1H), 2.18-1.92 (m, 8H), 1.57 (d, J=8.8 Hz, 3H).
TH 2956
1H NMR (CDCl3, 400 MHz) δ: 8.82 (d, J=4.0 Hz, 1H), 8.14 (d, J=11.2 Hz, 1H), 8.07 (d, J=9.6 Hz, 1H), 7.75-7.55 (m, 4H), 7.33 (dd, J=2.0, 11.2 Hz, 1H), 7.15 (d, J=2.0 Hz, 1H), 5.62-5.58 (m, 1H), 2.20-1.96 (m, 8H), 1.60 (d, J=9.2 Hz, 3H).
TH 2957
1H NMR (CDCl3, 400 MHz) δ: 8.82 (s, 1H), 8.17 (dd, J=2.0, 11.2 Hz, 1H), 8.08 (d, J=10.8 Hz, 1H), 7.89-7.86 (m, 1H), 7.43-7.33 (m, 4H), 7.27-7.26 (m, 1H), 5.62-5.58 (m, 1H), 2.22-2.00 (m, 8H), 1.62 (d, J=8.4 Hz, 3H).
TH 2958
1H NMR (CDCl3, 400 MHz) δ: 8.00 (d, J=11.6 Hz, 1H), 7.63-7.56 (m, 4H), 7.46 (t, J=9.6 Hz, 2H), 7.38 (d, J=9.6 Hz, 1H), 7.21 (d, J=10.8 Hz, 1H), 7.13 (d, J=12.0 Hz, 2H), 7.09 (s, 1H), 5.16 (d, J=10.8 Hz, 2H), 2.24-2.08 (m, 8H).
TH 2960
1H NMR (CDCl3, 400 MHz) δ 7.98 (dd, 1H), 7.75 (d, 1H), 7.60 (d, 1H), 7.43 (t, 2H), 7.24 (t, 1H), 7.04 (d, 2H) 5.42 (d, 2H), 2.23-2.12 (m, 8H).
TH 2961
Starting with 1-Phenyl-1-ethanone oxime (81 mg). 1H NMR (CDCl3) δ: 1.64 (d, 3H), 2.16-2.29 (m, 8H), 2.56 (s, 3H), 5.62 (m, 1H), 7.13 (dd, 1H), 7.44-7.49 (m, 3H), 7.75-7.79 (m, 2H), 7.92 (d, 1H), 8.04 (d, 1H).

1H NMR (CDCl3, 400 MHz) δ: 8.09 (d, J=10.4 Hz, 1H), 8.03 (d, J=11.2 Hz, 1H), 7.92 (d, J=10.0 Hz, 1H), 7.75 (d, J=10.0 Hz, 1H), 7.60-7.43 (m, 3H), 7.16 (d, J=11.2 Hz, 1H), 7.09 (d, J=10.0 Hz, 1H), 6.86 (s, 1H), 5.05 (d, J=10.0 Hz, 2H), 2.10-1.90 (m, 8H).
TH 2967
1H NMR (CDCl3, 400 MHz) δ: 9.00 (dd, J=2.0, 6.0 Hz, 1H), 8.52 (d, J=11.2 Hz, 1H), 8.06 (d, J=11.2 Hz, 1H), 7.98 (d, J=7.6 Hz, 1H), 7.67 (t, J=10.4 Hz, 2H), 7.48 (dd, J=5.6, 11.2 Hz, 1H), 7.26 (s, 1H), 7.05 (d, J=10.4 Hz, 1H), 5.12 (d, J=10.8 Hz, 2H), 2.20-2.02 (m, 8H).
TH 2968
1H NMR (CDCl3, 400 MHz) δ: 8.02 (d, J=10.8 Hz, 1H), 7.94-7.82 (m, 2H), 7.78-7.72 (m, 1H), 7.54-7.38 (m 3H), 7.32-7.20 (m, 2H), 7.05 (d, J=2.4 Hz, 1H), 5.13 (d, J=10.4 Hz, 2H), 2.12-2.05 (m, 8H).
TH 2969
1H NMR (CDCl3, 400 MHz) δ: 8.83 (d, J=4.0 Hz, 1H), 8.14 (d, J=11.2 Hz, 1H), 8.07 (d, J=10.8 Hz, 1H), 7.76-7.52 (m, 4H), 7.32 (d, J=10.8 Hz, 1H), 7.13 (s, 1H), 5.18 (d, J=10.4 Hz, 2H), 2.16-2.09 (m, 8H).
TH 2970
1NMR (CDCl3, 400 MHz) δ: 8.84 (d, J=4.0 Hz, 1H), 8.18 (d, J=10.0 Hz, 8.08 (d, J=11.6 Hz, 1H), 7.89 (d, J=7.2 Hz, 1H), 7.40-7.33 (m, 4H), 7.26 (s, 1H), 5.20 (d, J=10.4 Hz, 2H), 2.23-2.10 (m, 8H).
TH 2971
1H NMR (CDCl3, 400 MHz) δ: 8.96 (d, J=4.0 Hz, 1H), 8.15 (d, J=12.0H5.17 (d, J=10.8 Hz, 1H), 8.09-8.03 (m, 2H), 7.51 (dd, J=3.6, 12.0 Hz, 1H), 7.43 (dd, J=5.6, 11.2 Hz, 1H), 7.33 (d, J=3.2 Hz, 1.1H), 7.31-7.27 (m, 1H), 7.13-7.12 (m, 1H), 5.17 (d, J=10.8 Hz, 2H), 2.16-2.08 (m, 8H).
TH 2972
1H NMR (CDCl3, 400 MHz) δ: 7.96-7.93 (m, 1H), 7.41-7.36 (m, 1H), 7.26-7.23 (m, 1H), 7.18-7.15 (m, 1H), 7.10-7.09 (m, 1H), 7.05-7.02 (m, 2H), 5.58-5.54 (m, 1H), 3.80-3.40 (m, 8H), 2.10-1.98 (m, 8H), 1.56 (d, J=6.4 Hz, 3H).

1H NMR (CDCl3, 400 MHz) (δ: 7.98 (d, J=8.4 Hz, 1H), 7.42 (t, J=8.0 Hz, 1H), 7.28-7.26 (m, 1H), 7.22-7.20 (m, 1H), 7.18-7.03 (m, 3H), 5.16-5.14 (m, 1H), 3.80-3.35 (m, 8H), 2.18-2.10 (m, 8H), 1.58 (d, J=6.4 Hz, 3H).
TH 2974
1H NMR (CDCl3, 400 MHz) δ 7.93 (d, 1H), 7.32-7.20 (m, 8H), 7.02 (d, 2H), 6.96 (s, 1H), 5.10 (d, 2H), 3.48 (s, 3H), 2.17-2.00 (m, 8H).
TH 2978
1H NMR (CDCl3, 400 MHz) δ 7.93 (d, 1H), 7.32-7.20 (m, 8H), 7.02 (d, 2H), 6.96 (s, 1H), 5.30 (m, 1H), 3.40 (s, 3H), 2.17-2.00 (m, 8H), 1.56 (d, 3H).
TH 2980
Starting with 2-(methylsulfonyl)phenol (78 mg). 1H NMR (CDCl3) δ: 1.64 (d, 3H), 2.03-2.25 (m, 8H), 3.06 (s, 3H), 5.65 (m, 1H), 6.83 (d, 1H), 7.10 (d, 1H), 7.13-7.35 (m, 3H), 7.50 (dd, 1H), 8.02 (d, 1H).
TH 2981
Starting with 2-(methylsulfonyl)phenol (113 mg). 1H NMR (CDCl3) δ: 2.10-2.28 (m, 8H), 3.08 (s, 3H), 5.23 (d, 2H), 6.87 (d, 1H), 7.10 (d, 1H), 7.13-7.35 (m, 3H), 7.50 (dd, 1H), 8.05 (d, 1H).
TH 2982
Starting with 3-[(Piperidin-1-yl)carbonyl]phenol (123 mg). $^1$HNMR (CDCl$_3$) δ: 1.52 (br, 2H), 1.58 (d, 3H), 1.67 (br, 4H), 2.00-2.2.0 (m, 8H), 3.33 (br, 2H), 3.68 (br, 2H), 5.59 (m, 1H), 7.03-7.07 (m, 2H), 7.10 (s, 7.19 (d, 1H), 7.27 (d, 1H), 7.41 (t, 1H), 7.97 (d, 1H). $^{31}$PNMR (CDCl$_3$) δ: 31.2.
TH 2983
Starting with 3-[(Piperidin-1-yl)carbonyl]phenol (135 mg). (CDCl$_3$) δ: 1.51 (br, 2H), 1.66 (br, 4H), 2.10-2.20 (m, 8H), 3.32 (br, 2H), 3.68 (br, 2H), 5.14 (d, 2H), 7.03 (s, 1H), 7.07-7.09 (m, 2H), 7.20 (d, 1H), 7.25 (d, 1H), 7.42 (t, 1H), 7.98 (d, 1H). $^{31}$PNMR (CDCl$_3$) δ: 32.0.

1H NMR (CDCl3) δ 7.99 (d, 1H), 7.42 (t, 1H), 7.32 (d, 1H), 7.3-7.24 (m, 1H), 7.17 (s, 1H), 7.12-7.06 (m, 2H), 5.65-5.55 (m, 1H), 3.62 (t, 2H), 3.42 (t, 2H), 2.22-1.85 (m, 12H), 1.58 (d, 3H).

TH 2985

1H NMR (CDCl3) δ 7.98 (d, 1H), 7.41 (t, 1H), 7.29-7.24 (m, 1H), 7.2-15 (m, 1H), 7.09 (d, 1H), 7.1-7.0 (m, 2H), 5.65-5.55 (m, 1H), 3.6-3.45 (m, 2H), 3.3-3.2 (m, 2H), 2.22-2 (m, 8H), 1.57 (d, 3H) 1.46-1.4 (m, 6H).

TH 2991

1H NMR (CDCl3) δ 7.99 (d, 1H), 7.57 (d, 2H), 7.5-7.42 (m, 4H), 7.38 (d, 1H), 7.28 (s, 1H), 7.21 (dd, 1H), 7.11 (d, 1H), 7.38 (dt, 1H), 5.65-5.55 (m, 1H), 2.16-1.92 (m, 8H) 1.57 (d, 3H).

TH 2992

1H NMR (CDCl3) δ 7.96 (d, 1H), 7.3-7.22 (m, 3H), 7.2-7.14 m, 2H), 7.07-7.0 (m, 3H), 7.08-6.9 (m, 3H), 5.65-5.55 (m, 1H), 2.22-2.0 (m, 8H), 1.58 (d, 3H).

TH 2993

1H NMR (CDCl3) δ 8.0 (d, 1H), 7.47 (t, 1H), 7.32 (dd, 1H), 7.21 (d, 1H), 7.2 (s, 1H), 7.14 (dd, 3H), 7.06 (d 1H), 5.65-5.55 (m, 1H), 4.3-3.9 (m, 4H), 3.2-2.9 (m, 4H), 2.22-2.02 (m, 8H), 1.62 (d, 3H).

TH 3028

1H NMR (CDCl3, 400 MHz) δ 7.84 (d, 1H), 7.54-7.49 (m, 3H), 7.40-7.22. (n, 6H), 7.11 (dd, 1H), 7.01 (dd, 1H), 6.71 (d, 1H), 5.42 (m, 1H), 2.12-1.90 On, 8H), 1.44 (d,

TH 3029

1H NMR (CDCl3, 400 MHz) δ 7.85 (d, 1H), 7.54-7.49 (m, 3H), 7.40-7.22 (m, 6H), 7.11 (dd, 1H), 7.01 (dd, 1H), 6.75 (s, 1H), 5.00 (d, 2H), 2.14-2.03 (m, 8H).

TH 3030

1H NMR (CDCl3, 400 MHz) δ 7.92 (d, 1H), 7.15 (t, 3H), 6.94 (t, 3H), 5.53 (m, 1H), 2.34 (s, 3H), 2.18-1.96 (m, 8H), 1.53 (d, 3H).

1H NMR (CDCl3, 400 MHz) δ 7.92 (d, 1H), 7.17 (d, 2H), 7.13 (d, 1H), 6.95-6.93 (bm, 3H), 5.08 (d, 2H), 2.34 (s, 3H), 2.18-2.05 (m, 8H).

TH 3032

1H NMR (CDCl3, 400 MHz) δ 7.98 (d 1H), 7.35 (d, 2H), 7.30-7.22 (m, 5H), 7.15 (s, 1H), 7.10 (d, 2H), 5.6 (m, 1H), 2.30 (s, 3H), 2.22-2.00 (m, 8H), 1.60 (d, 3H).

TH 3033

1H NMR (CDCl3, 400 MHz) δ 7.98 (d, 1H), 7.33 (d, 2H), 7.26-7.20 (m, 5H). 7.12 (s, 1H), 7.09 (d, 2H), 5.15 (d, 2H), 2.85 (s, 3H), 2.22-2.00 (m, 8H).

TH 3034

1H NMR (CDCl3, 400 MHz) δ 7.94 (d, 1H), 7.41 (d, 2H), 7.16 (d, 1H), 6.99 (t, 3H), 5.56 (m, 1H), 2.18-1.96 (m, 8H), 1.57 (d, 3H), 1.34 (s, 9H).

TH 3035

1H NMR (CDCl3, 400 MHz) δ 7.95 (d, 1H), 7.40 (d, 2H), 7.15 (d, 1H), 7.00-6.99 (m, 3H), 5.11 (d, 2H), 2.18-2.08 (m, 8H), 1.33 (s, 9H).

TH 3036

1H NMR (CDCl3, 400 MHz) δ 8.01 (d, 1H), 7.62 (d, 2H), 7.31 (dd, 1H), 7.16 (d, 1H), 7.07 (d, 2H), 5.62 (m, 1H), 2.20-2.00 (m, 8H), 1.59 (d, 3H).

TH 3037

1H NMR (CDCl3, 400 MHz) δ 8.01 (d, 1H), 7.62 (d, 2H), 7.31 (dd, 1H), 7.14 (s, 1H), 7.08 (d, 2H), 5.17 (d, 2H), 2.20-2.00 (m, 8H).

TH 3040

1H NMR (CDCl3, 400 MHz) δ: 7.99 (d, J=8.4 Hz, 1H), 7.62-7.57 (m, 4H), 7.46 (t, J=7.6 Hz, 2H), 7.37 (t, J=7.2 Hz, 1H), 7.23 (dd, J=8.4, 1.6 Hz, 1H), 7.13-7.11 (m, 3H), 5.61-5.58 (m, 1H), 2.22-1.81 (m, 8H), 1.58 (d, J=6.8 Hz, 3H) ppm.

TH 3041

1H NMR (CDCl3) δ 7.99 (d, 1H), 7.57 (d, 2H), 7.5 (d, 2H), 7.42 (d, 2H), 7.25 (dd, 1H), 7.14-7.09 (m, 3H), 5.65-5.55 (m, 1H), 2.2-1.98 (m, 8H), 1.59 (d, 3H).

1H NMR (CDCl3) δ 7.99 (d, 1H), 7.58-7.5 (m, 4H), 7.24 (dd, 1H), 7.18-7.09 (m, 5H), 5.65-5.55 (m, 1H), 2.2-1.98 (m, 8H), 1.59 (d, 3H).

TH 3045

1H NMR (CDCl3, 400 MHz) δ: 7.99 (d, J=8.4 Hz, 1H), 7.62-7.57 (m, 4H), 7.46 (t, J=7.6 Hz, 2H), 7.37 (t, J=7.2 Hz, 1H), 7.23 (dd, J=8.4, 1.6 Hz, 1H), 7.13-7.11 (m, 3H), 5.61-5.58 (m, 1H), 2.22-1.81 (m, 8H), 1.58 (d, J=6.8 Hz, 3H) ppm.

TH 3050

1H NMR (CDCl3, 400 MHz) δ: 8.66 (d, J=6.4 Hz, 2H), 8.01 (d, J=8.4 Hz, 1H), 7.67 (d, J=8.4 Hz, 2H), 7.49-7.47 (m, 2H), 7.28-7.27 (m, 1H), 7.15-7.13 (m, 3H).

Example 2. In Vitro Human Tumor Cell Line Cytotoxicity Assays

In vitro proliferation data on the H460 non cell lung cancer human tumor cell line is reported above in the compound table. IC50 values are reported in micromolar and result from exposure of compound at various concentrations for 2 hrs followed by a wash step and addition of fresh media followed by growth and cell viability staining and comparison to a media only treated control.

Specifically, exponentially growing cells were seeded at a density of 4×10$^3$ cells per well in a 96 well plate and incubated at 37° C. in 5% CO$_2$, 95% air and 100% relative humidity for 24 hours prior to addition of test compounds. Compounds were solubilized in 100% DMSO at 200 times the desired final test concentration. At the time of drug addition, compounds were further diluted to 4 times the desired final concentration with complete medium. Aliquots of 50 µl of compound at specified concentrations were added to microtiter wells already containing 150 µl of medium, resulting in the final drug concentration reported. After drug addition, the plates were incubated for an additional 2 hours at 37° C., 5% CO$_2$, 95% air, and 100% relative humidity, then the drug was washed off and fresh medium was added and the plates were incubated for addition 70 hrs at 37° C., 5% CO$_2$, 95% air and 100% relative humidity. At the end of this incubation, the viable cells were quantified using the AlamarBlue assay. The drug concentration resulting in growth inhibition of 50% (IC$_{50}$) was calculated using Prism software (Irvine, Calif.), and the results were listed in the table.

The H460 data above demonstrates a substantial antitumor effect with inhibition at down to low nanomolar levels for various compounds for only a 2. hr. exposure.

TH 2870 was also tested in different cancer cell lines using the materials and procedures as follows. 10*cell lysate buffer (cell signaling technology, Cat. No. 9803); Protease Inhibitor Cocktail for Mammalian Tissues (Sigma, Cat. No. P8340); Phosphatase Inhibitor Cocktails for Serine/Threonine Phosphatases and L-Isozymes of Alkaline Phosphatases (Sigma, Cat. No. P0044); Phosphatase Inhibitor Cocktails for Tyrosine Protein Phosphatases, Acid and Alkaline Phosphatases (Sigma, Cat. No. P5726); BCA kit (Thermo, Cat. No. 23225); Primary antibody, mouse monoclonal AKR1C3 antibody (clone NP6.G6.A6; Sigma-Aldrich); Primary antibody, α-tubulin (clone B-5-1-2; Sigma-Aldrich); Secondary antibody, Goat-anti-Mouse IgG HRP conjugated (A4416; Sigma-Aldrich) were used. Cells were passaged two generations in good condition and digested. The appropriate number of cells were inoculated in 6-cm cell culture dishes, and incubated at 37° C., 5% CO2 overnight. When the cells were grown to 80% density, the dish was removed from incubator. The medium was aspirated, washed twice with ice-cold PBS, and residual PBS was removed. An appropriate volume of ice-cold 1*cell lysate was added and incubated on ice for 10 minutes. Cell lysate was transferred to microfuge tubes chilled in ice, 4° C., 12,000 rpm and centrifuged for 15 minutes. Supernatant was transferred into another microcentrifuge tube. Cell lysates were diluted by a 10*cell lysates, and add Protease Inhibitor Cocktail for Mammalian Tissues (Sigma, #P8340), Phosphatase Inhibitor Cocktails for Serine/Threonine Phosphatases and L-Isozymes of Alkaline Phosphatases, Phosphatase Inhibitor Cocktails for Tyrosine Protein Phosphatases, Acid and Alkaline Phosphatases. The BCA protein quantification kit for protein quantification was used with 1*cell lysate to dilute the cell lysate to the same concentration. Corresponding samples were added on 5* SDS-loading buffer, heated to 85° C. for 10 minutes, and centrifuged briefly. The samples were saved at −20° C. or used directly for protein electrophoresis. The samples were saved at −20° C. or used directly for protein electrophoresis. Those samples were electrophoresed according to standard practice, transferred to a membrane, the primary antibodies and then secondary antibody were applied according to the manufacturer's instructions. Odyssey infrared laser imaging system was used to scan signals.

Figure 2:
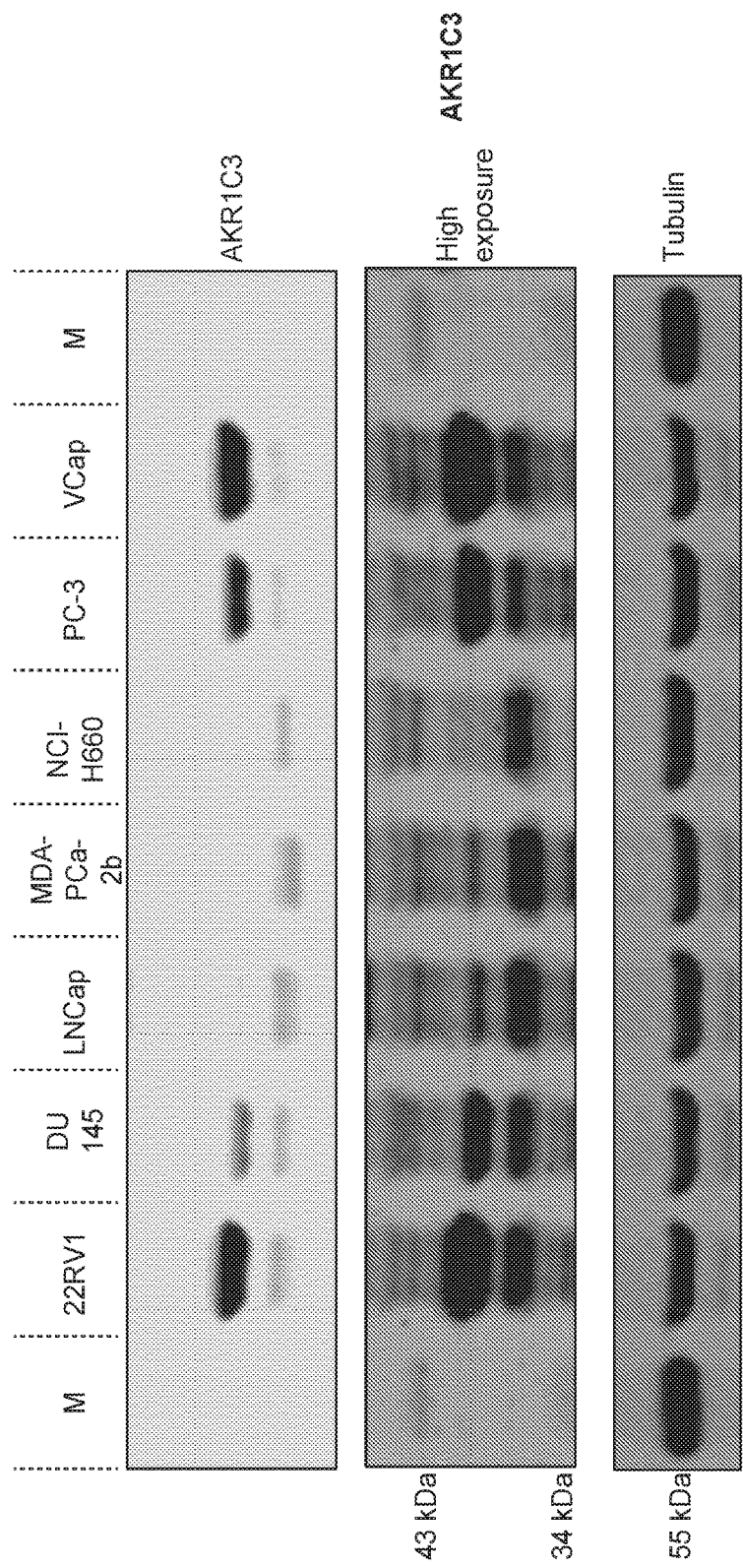
FIG. 2 illustrates AKR1C3 expression in prostate cancer cell lines.
Figure 3:
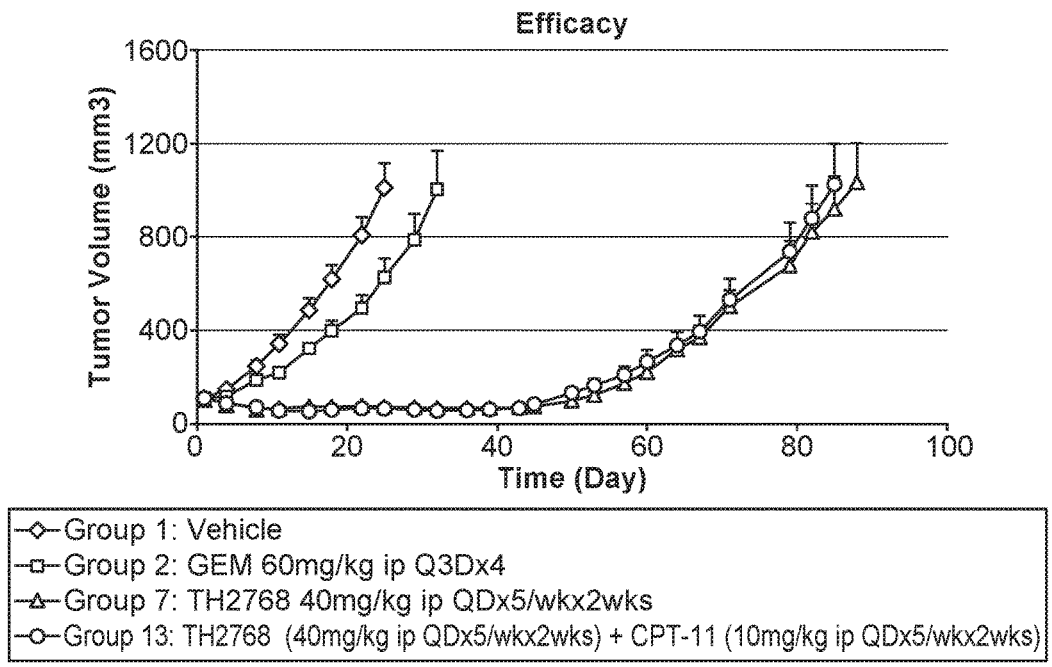
FIG. 3 illustrates Antitumor efficacy of TH-2768 alone and in combination with irinotecan (CPT-11) in comparison with gemcitabine in the ectopic H460, NSCLC xenograft model described in Example 4-A.
Figure 4:
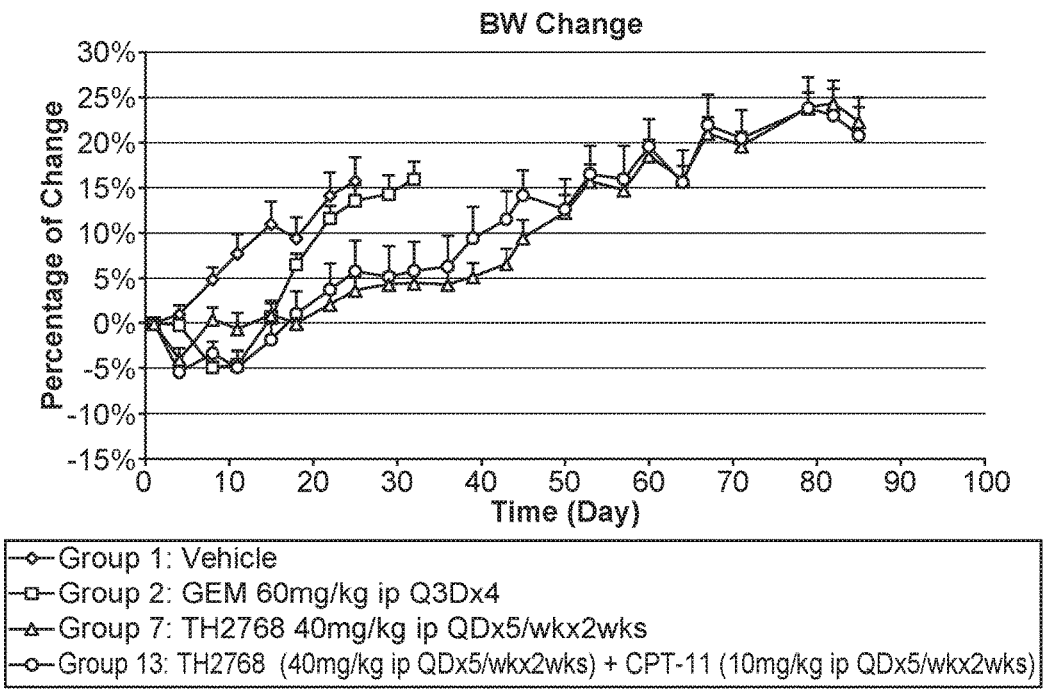
FIG. 4 illustrates body weight change induced by TH-2768 treatment alone and in combination with irinotecan (CPT-11) in comparison with gemcitabine in the ectopic H460, NSCLC xenograft model Example 4-A.
Figure 5:
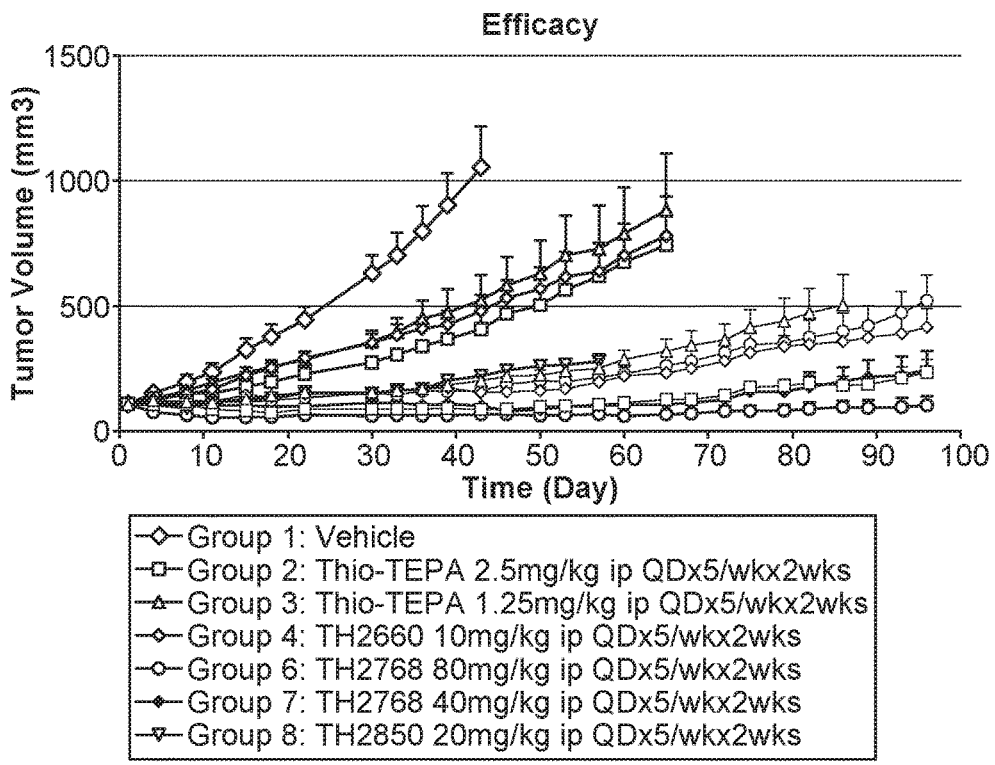
FIG. 5 illustrates antitumor efficacy of TH-2768, TH-2850, TH-2852, TH-870, or TH-2889 in comparison with Thio-TEPA in the ectopic A549, NSCLC xenograft model described in Example 4-B.
Figure 6:
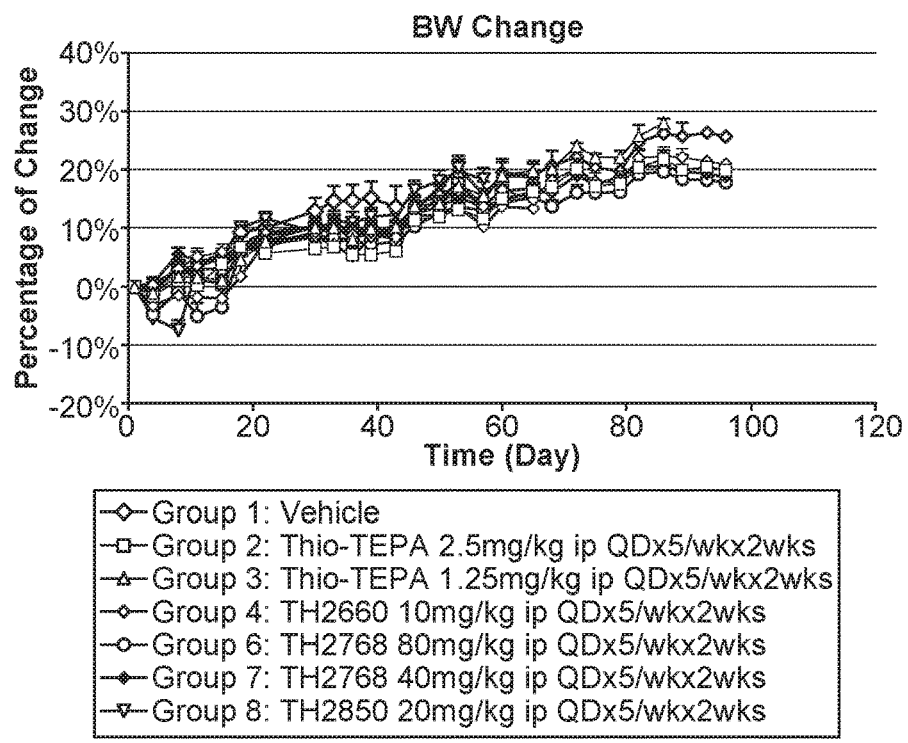
FIG. 6 illustrates body weight change induced by TH-2768, TH-2850, TH-2852, TH-2870, or TH-2889 in comparison with Thio-TEPA in the ectopic A549, NSCLC xenograft model described in Example 4-B.
Figure 7:
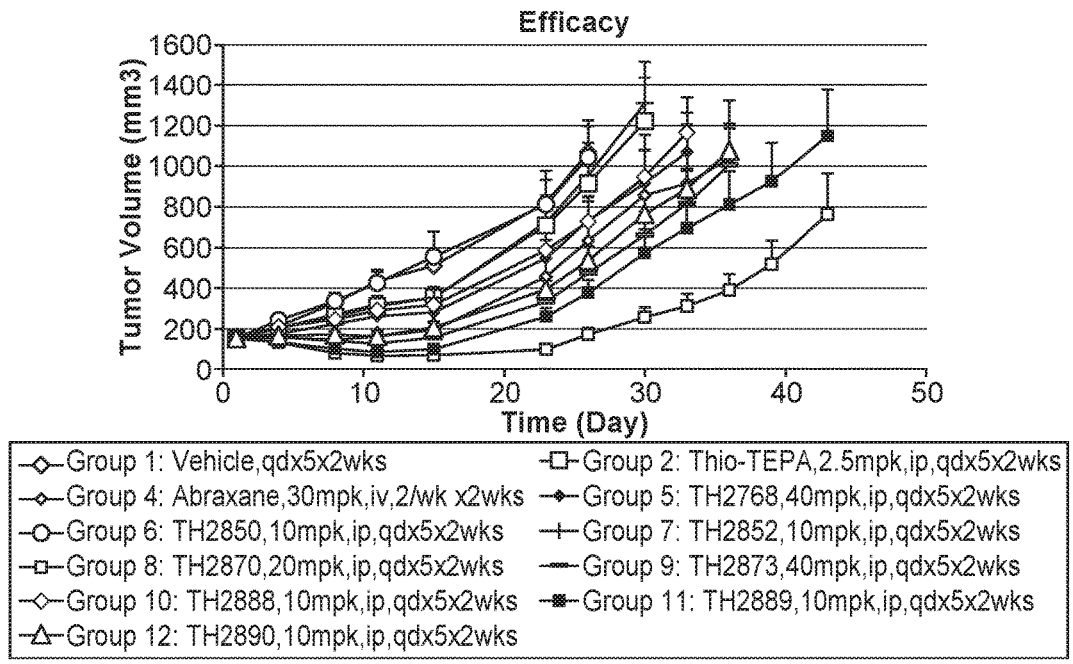
FIG. 7 illustrates antitumor efficacy of TH-2768, TH-2850, TH-2870, TH-2873, TH-2888, TH-2889 or TH-2890 in comparison with Thio-TEPA or nab-Paclitaxel in the ectopic A375, melanoma xenograft model described in Example 4-C.
Figure 8:
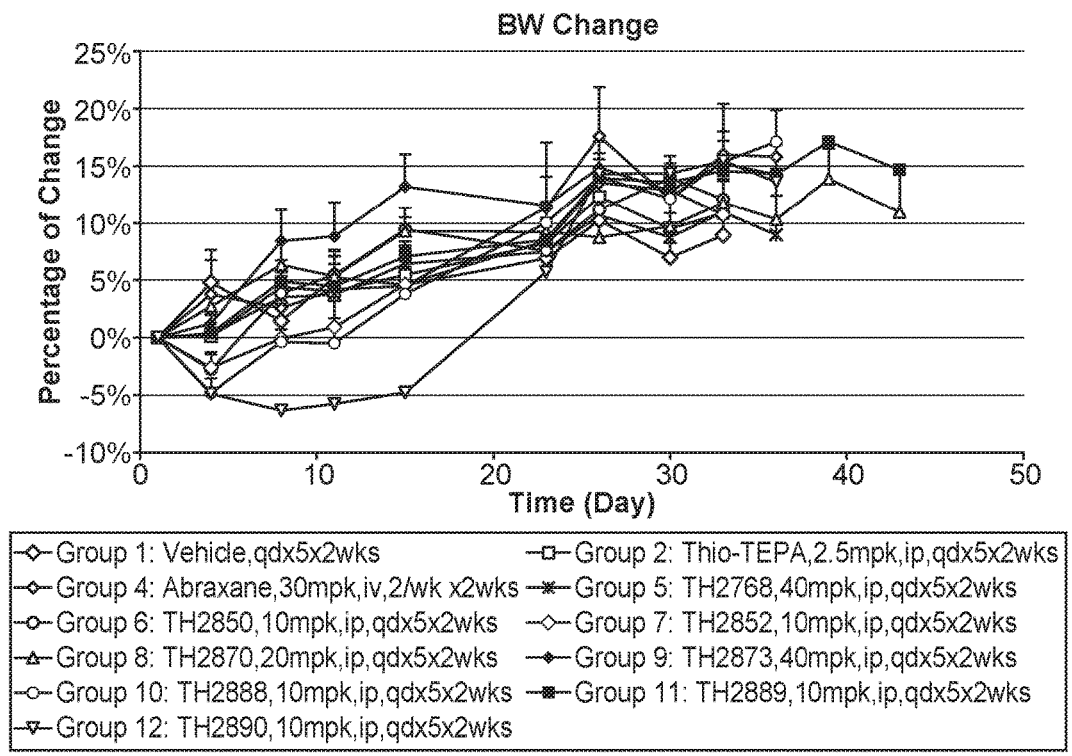
FIG. 8 illustrates body weight change induced by TH-2768, TH-2850, TH-2870, TH-2873, TH-2888, TH-2889 or TH-2890 in comparison with Thio-TEPA or nab-Paclitaxel in the ectopic A375, melanoma xenograft model described in Example 4-C.
Figure 9:
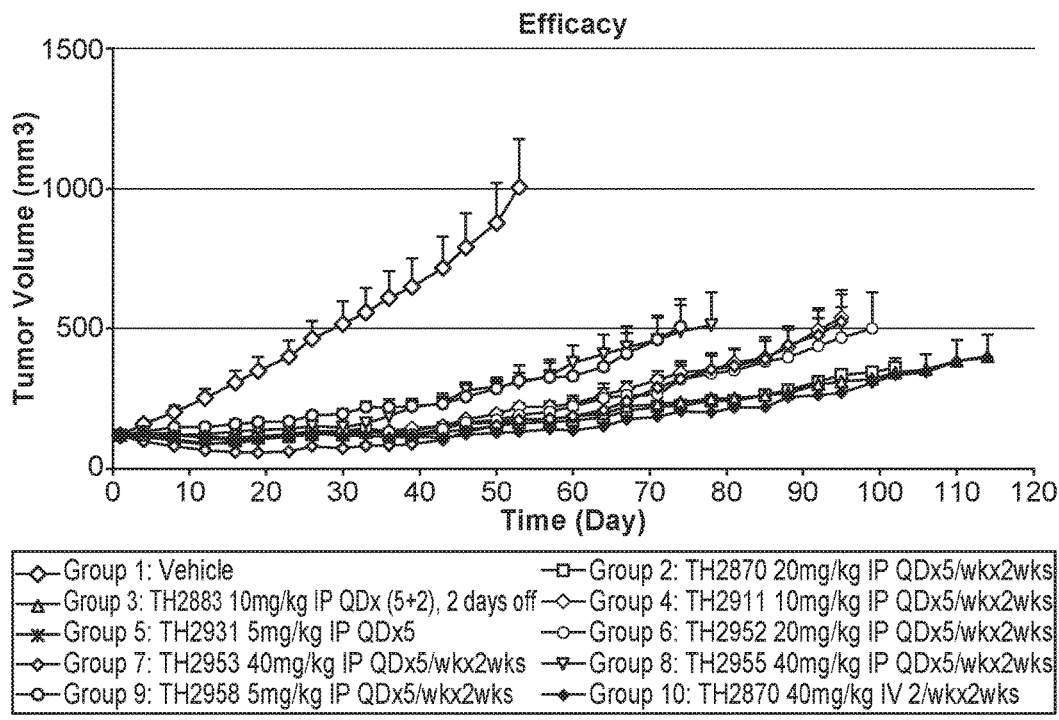
FIG. 9 illustrates antitumor efficacy of TH-2870, TH-2883, TH-2911, TH-2952, TH-2953, TH-2955, or TH-2958 in the ectopic A549. NSCLC xenograft model described in Example 4-D.
Figure 10:
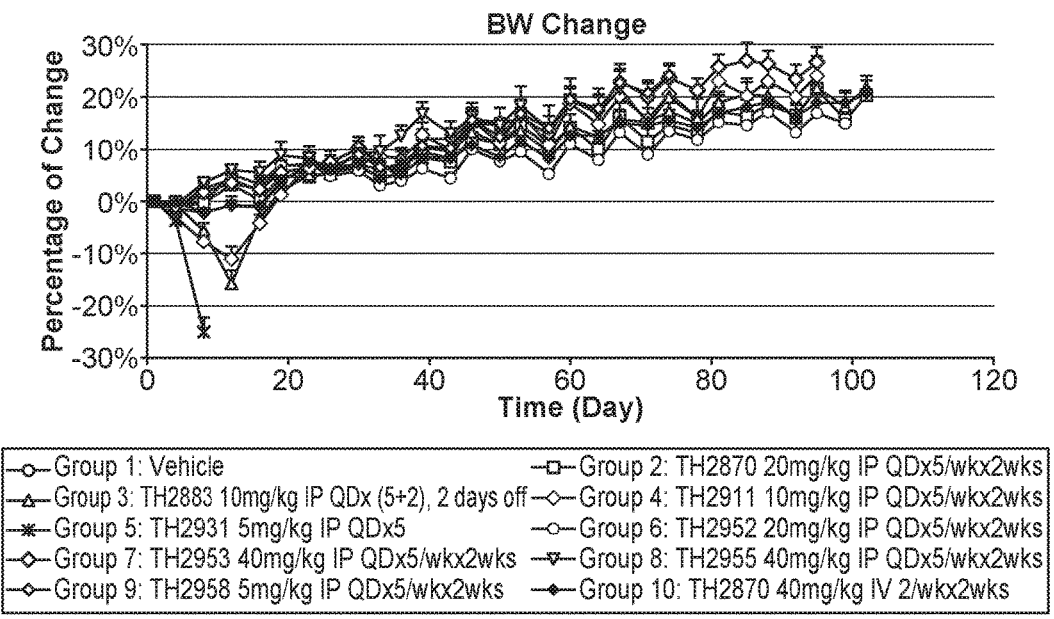
FIG. 10 illustrates body weight change induced by TH-2870, TH-2883, TH-2911, TH-2952, TH-2953, TH-2955, or TH-958 in the ectopic A549, NSCLC xenograft model described in Example 4-D.
Figure 11:
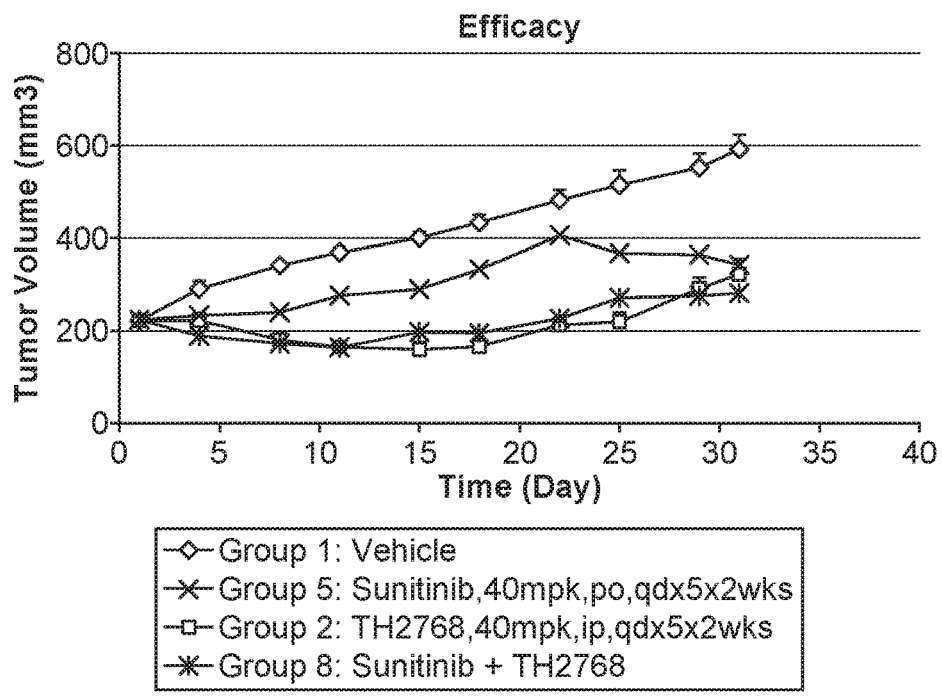
FIG. 11 illustrates antitumor efficacy of TH-870 alone or in combination with sunitinib in the ectopic 786-O, RCC xenograft model described in Example 4-E.
Figure 12:
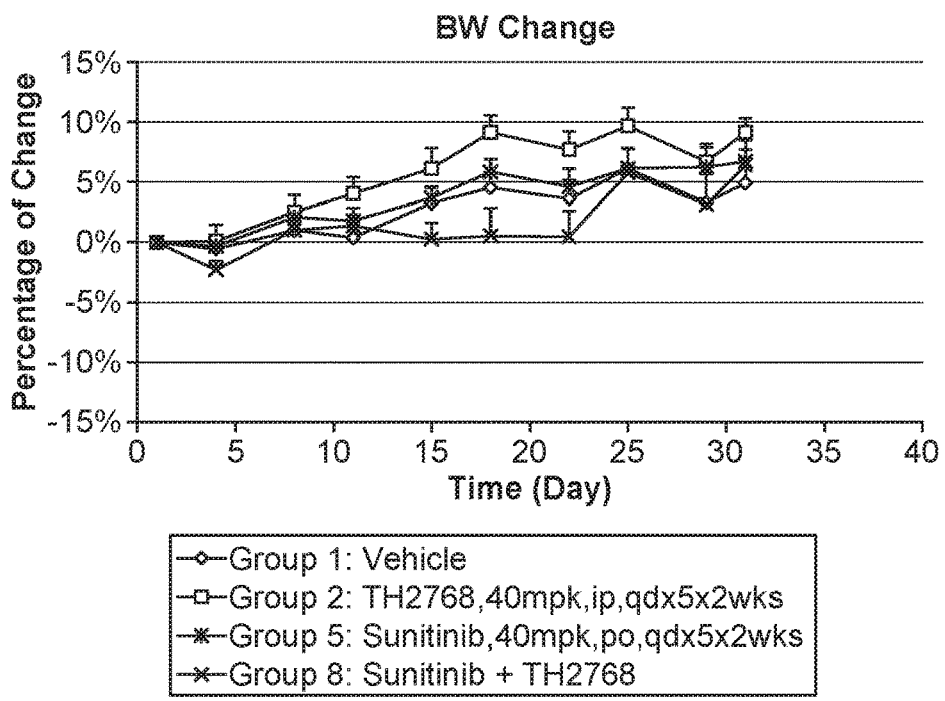
FIG. 12 illustrates body weight change induced by TH-2870 alone or in combination with sunitinib in the ectopic 786-O, RCC xenograft model described in Example 4-E.
Figure 13:
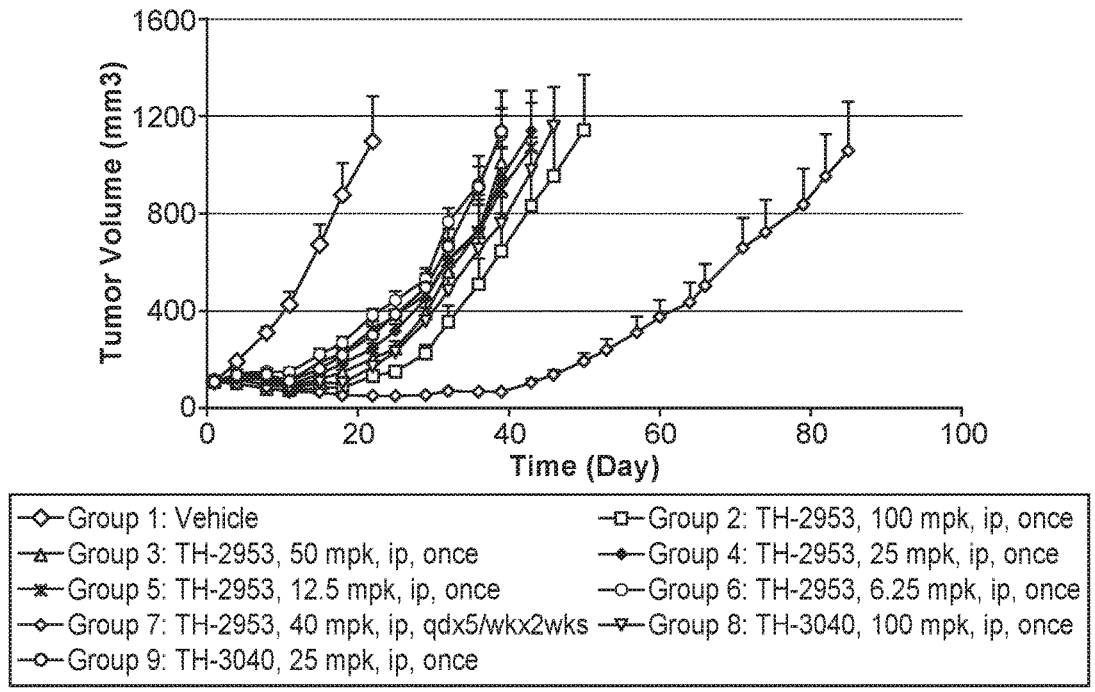
FIG. 13 illustrates antitumor efficacy of TH-2953 or TH-3040 in the ectopic H460 NSCLC xenograft model described in Example 4-F.
Figure 14:
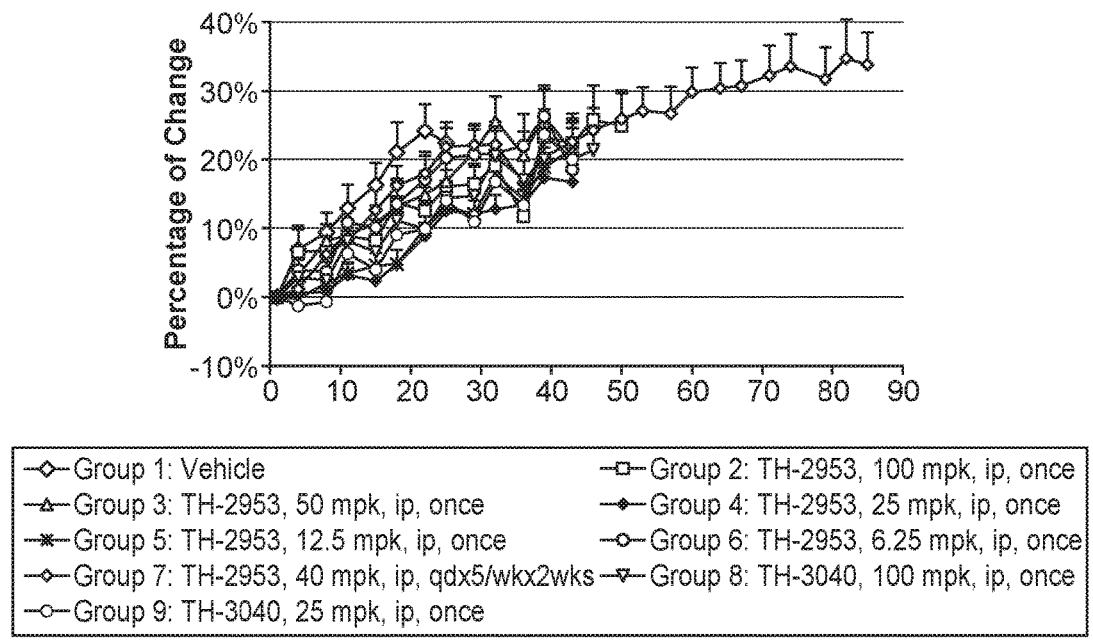
FIG. 14 illustrates body weight change induced by TH-2953 or TH-3040 in the ectopic H460 NSCLC xenograft model described in Example 4-F.
Figure 15:
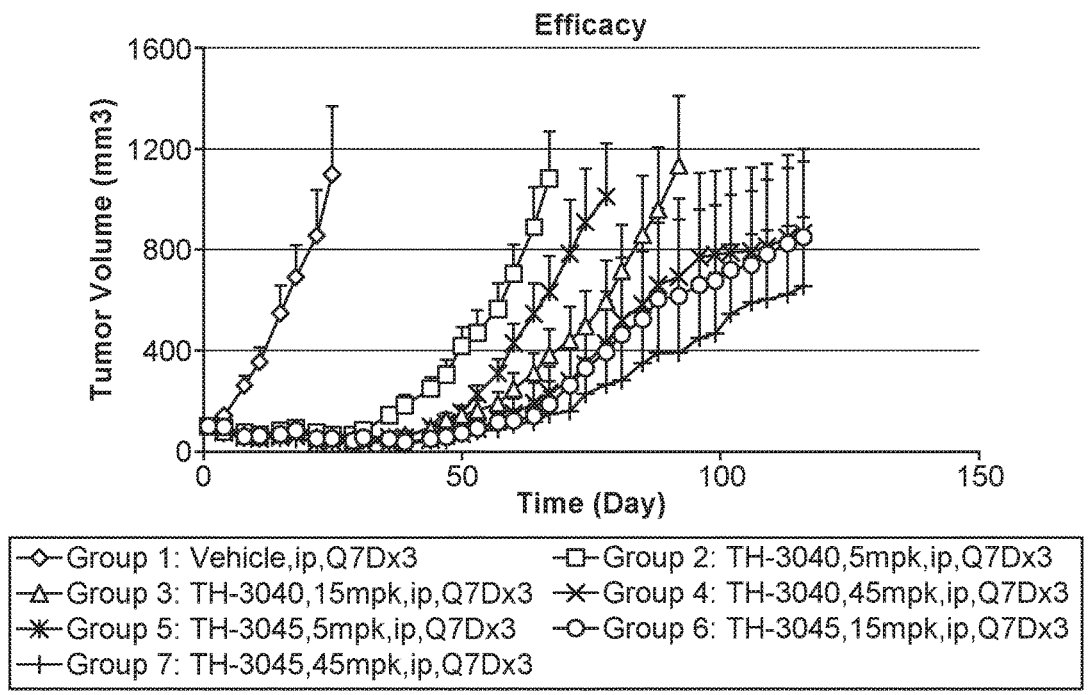
FIG. 15 illustrates antitumor efficacy of TH-3040 or TH-3045 in the ectopic H460 NSCLC xenograft model described in Example 4-G.
Figure 16:
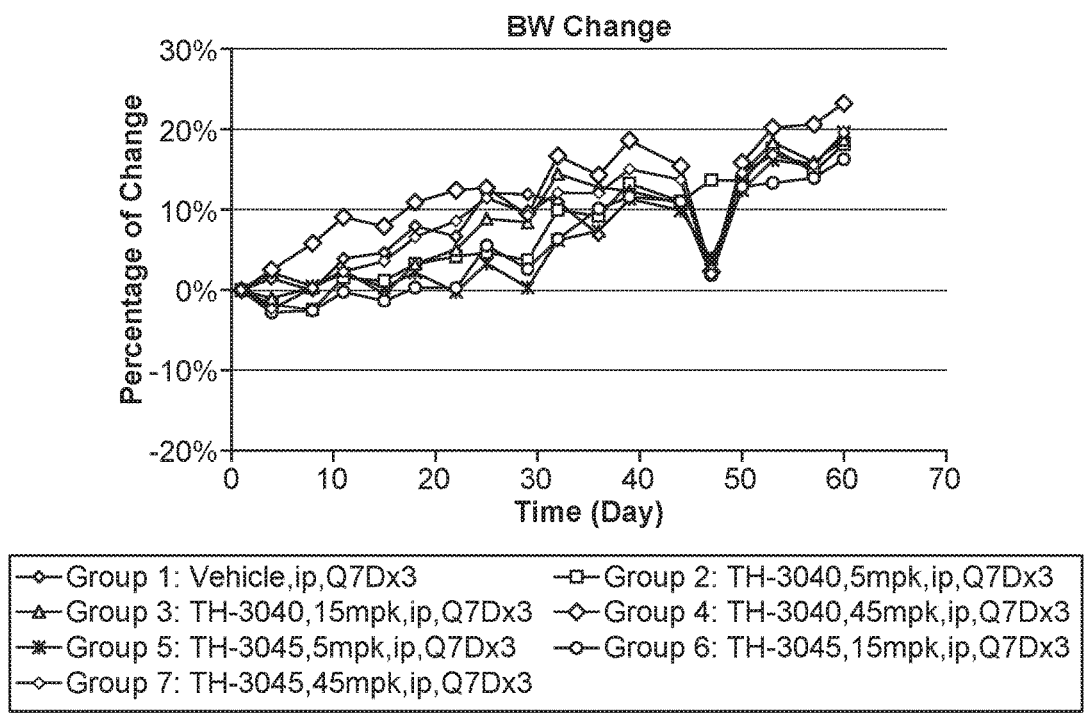
FIG. 16 illustrates body weight change induced by TH-3040 or TH-3045 in the ectopic H460 NSCLC xenograft model described in Example 4-G.
Figure 17:
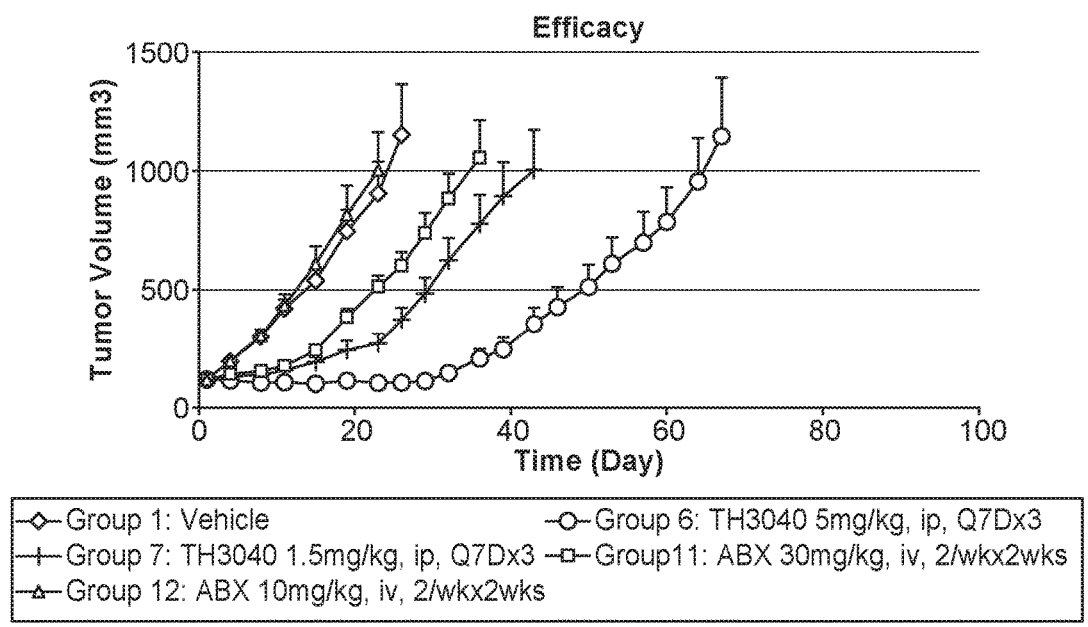
FIG. 17 illustrates antitumor efficacy of TH-3040 in comparison with nab-paclitaxel in the ectopic H460 NSCLC xenograft model described in Example 4-H.
Figure 18:
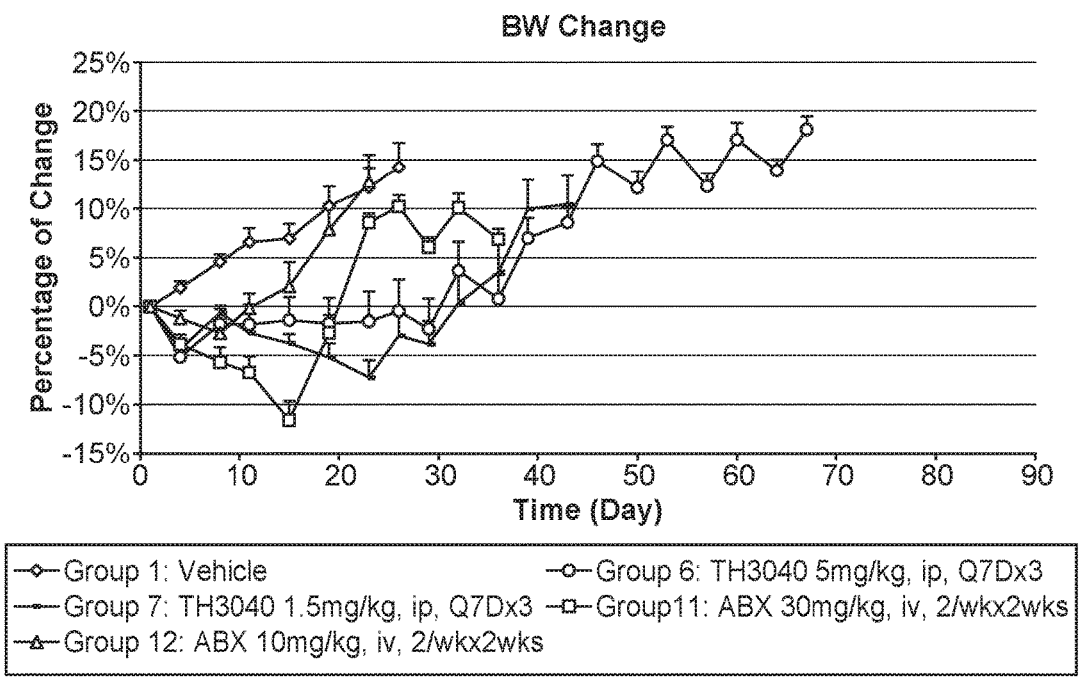
FIG. 18 illustrates body weight change induced by TH-3040 in comparison with nab-paclitaxel in the ectopic H460 NSCLC xenograft model described in Example 4-H.
Figure 19:
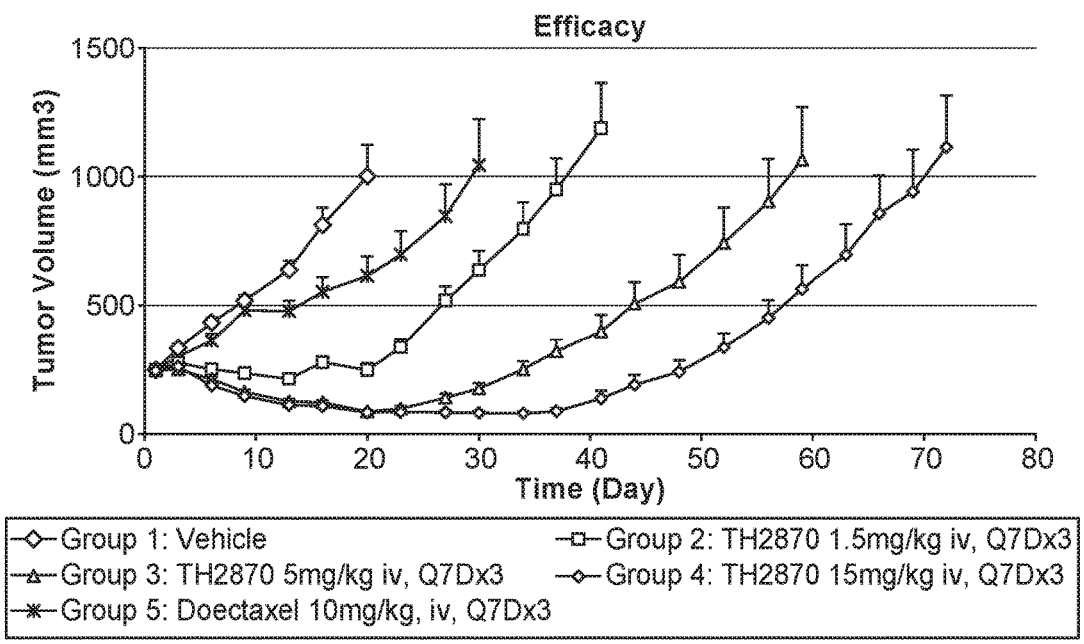
FIG. 19 illustrates antitumor efficacy of TH-2870 in comparison with docetaxel in the ectopic H460 NSCLC xenograft model described in Example 4-I.
Figure 20:
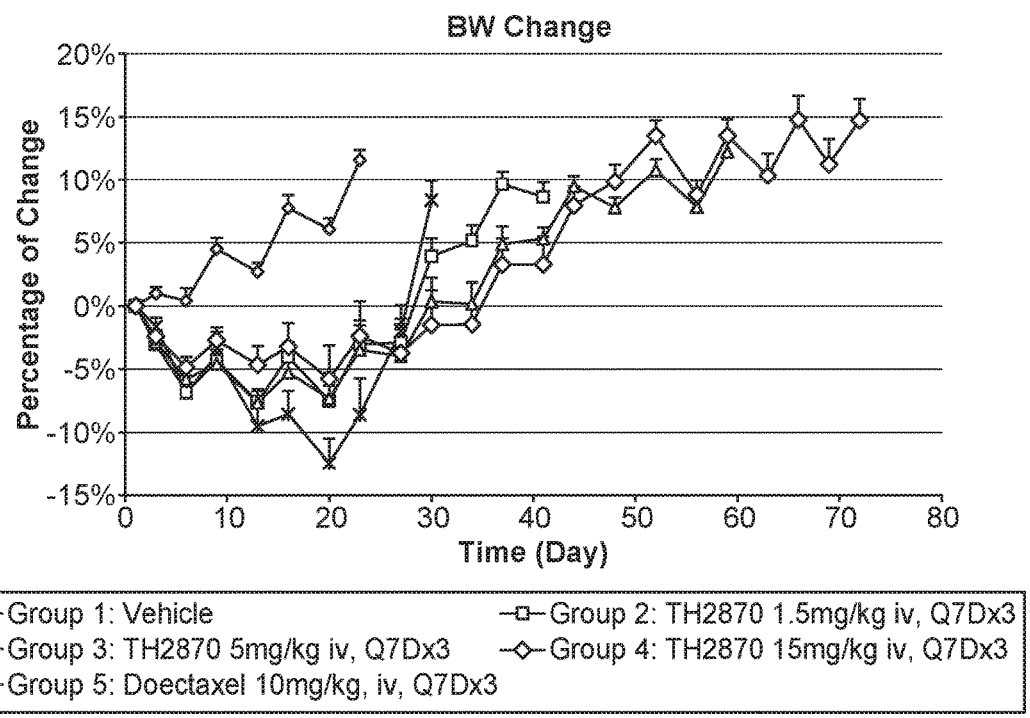
FIG. 20 illustrates body weight change induced by TH-2870 in comparison with docetaxel in the ectopic H460 NSCLC xenograft model described in Example 4-I.

The results are shown below in FIGS. 1 and 2 and listed in the following tables:

TABLE

TH2870 sensitivity correlates with AKR1C3 expression in liver cancer cells

| Cell line | Expression | RelIC50(μM) | Max Inhibition % |
|---|---|---|---|
| C3A | ++++ | 0.0071 | 98.1 |
| Hep G2 | ++++ | 0.0055 | 98.9 |
| SNU-387 | ++++ | 0.0422 | 102.8 |
| SNU-449 | ++++ | 0.0400 | 99.6 |
| SNU-475 | ++++ | 0.0080 | 100.4 |
| LIC-0903 | ++++ | 0.0819 | 96.3 |
| LIXC-003 | ++++ | 0.0054 | 44.6 |
| LIXC-012 | ++++ | 0.0274 | 87.1 |
| LIXC-086 | ++++ | 0.0410 | 92.8 |
| LIXC-011 | ++++ | 0.0408 | 97.4 |
| HCCC-9810 | ++++ | 0.0292 | 95.4 |
| JHH-7 | +++ | 0.1074 | 69.8 |
| PLC/PRF/5 | +++ | 0.4745 | 53.3 |
| LIXC-002 | +++ | 0.0560 | 99.1 |
| LIXC-004 | +++ | 0.0313 | 83.6 |
| LIXC-006 | +++ | 0.1156 | 71.7 |
| HLE | ++ | 0.0842 | 80.5 |
| LIXC-066 | ++ | 0.0941 | 75.4 |
| HuCCT1 | + | 0.1252 | 66.7 |
| SNU-423 | + | >1 | 43.3 |
| Hep 3B2.1-7 | / | >1 | 8.1 |

TABLE-continued

TH2870 sensitivity correlates with AKR1C3 expression in liver cancer cells

| Cell line | Expression | RelIC50(μM) | Max Inhibition % |
|---|---|---|---|
| HLF | / | >1 | 22.5 |
| SNU-182 | / | >1 | 19.4 |
| SNU-398 | / | >1 | 15.3 |
| SK-HEP-1 | / | >1 | 44.3 |

TABLE

TH2870 sensitivity in prostate cancer cell lines

| 22RV1 | Vcap | DU145 | PC-3 | LNCap | MDA-Pca-2b | NCI-H660 |
|---|---|---|---|---|---|---|
| 0.0019 | 0.0152 | 0.0429 | 0.1612 | 0.1616 | >0.3 | >0.3 |

Example 3. In Vivo Human Tumor Xenograft Models and Antitumor Activity

Four human xenograft anti-tumor models utilizing non-small cell lung cancer H460, non-small cell lung cancer A549, melanoma A375 models, and renal cell carcinoma 786-O were used to demonstrate the efficacy of the compounds provided herein in 9 studies.

Specific pathogen-free homozygous female nude mice (nu/nu, Charles River Laboratories) were used. Mice were given food and water ad libitum and housed in microisolator cages. Four to six week old animals were identified by microchips (Locus Technology, Manchester, Md., USA) at the time of the experiments. All animal studies were approved by the Institutional Animal Care and Use Committee at Threshold Pharmaceuticals, Inc.

All cell lines were from the American Type Culture Collection (ATCC, Rockville, Md., USA). Cells were cultured in the suggested medium with 10% fetal bovine serum and maintained in a 5% $CO_2$ humidified environment at 37° C.

Cells were mixed with Matrigel (50% with exception for 30% in the H460) and 0.2 ml per mouse were subcutaneously implanted to the flank area of the animals. When tumor size reached 100-150 250 mm3, mice were randomized into experimental or vehicle groups with 10 mice/group and treatment was started (Day 1). The tested compounds were formulated in 5% DMSO in D5W. The regimens employed in the examples include IP, QD×5/wk (5 days on, 2 days off) as one cycle, for a total of 2 cycles; IP, once; IP, weekly for total 3 weeks; and IV, weekly for 3 weeks. Tumor growth and body weight were measured twice a week. Tumor volume was calculated as (length×width2)/2. Drug efficacy was assessed as Tumor Growth Inhibition (TGI) and Tumor Growth Delay (TGD). TGI was defined as $(1-\Delta T/\Delta C)\times 100$. where $\Delta T/\Delta C$ presented the ratio of the change in mean (or median, if variation within the group was relatively large) tumor volume of the treated group and of the control group. TGD was calculated as the extra days for the treated tumor to reach 500 mm3 or 1000 mm3 as compared to the control group. Animals were culled when individual tumor size reached over 2000 mm3 or mean tumor volume exceeded 1000 mm3 in the group. Data are expressed as the mean±SEM. One-way analysis of variance with Dunnett post comparison test (GraphPad Prism 4) or two-tailed student's t-test were used for analysis. A P level <0.05 was considered statistically significant.

Example 4. In Vivo Efficacy Results

Example 4-A

Compounds provided herein were tested in vivo human tumor xenograft models and compared to standard chemotherapeutic agents such as gemcitabine, nab-paclitaxel. The experiments below demonstrate the antitumor effects of a compound provided herein on H460 non-small cell lung cancer xenograft tumor. The compound was dosed as follows: daily IP dosing: 5 doses then 2 days off then 5 more doses starting at 100 mm$^3$ tumors on day 1 (10 animals per group median tumor volume). It is contemplated that in some embodiments, the compounds provided herein are activated by human and not by mouse enzymes. The antitumor effects and the safety of administration are graphically illustrated in FIGS. 3-20 below.

| Group | TGI | TGD 500 | TGD 1000 | Max. BW loss % |
|---|---|---|---|---|
| Group 1: Vehicle | | | | 0.0% |
| Group 2: GEM 60 mg/kg ip Q3Dx5 | 42.7% | 7 | 7 | 4.9% |
| Group 7: TH2768 40 mg/kg ip QDx5/wkx2wks | 104.1% | 56 | 62 | 4.0% |
| Group 13: TH2768 (40 mg/kg ip QDx5/wkx2wks) + CPT-11 (10 mg/kg ip QDx5/wkx2wks) | 104.8% | 55 | 59 | 5.4% |

Before this study, TH 2768 was tested in CD1 mice for toxicity under the same dosing protocol as the efficacy study (daily IP 5 days on 2 days off and 5 days on). A maximum tolerated dose was determined where the average weight loss of the mice was less than 5% and no mouse lost more than 20%. This dose was then used for the subsequent efficacy study. In the H460 study an antitumor effect of TH-2768 as a monotherapy is superior to the effect of gemcitabine.

Example 4-B

Antitumor effects of compounds provided herein were determined on A549 non-small cell lung xenograft model in comparison with a chemotherapy agent, thiotepa. The dosing was as follows. Daily IP dosing: 5 doses then 2 days off then 5 more doses starting at 110 mm$^3$ tumors on day 1 (10 animals per group average tumor volume). The antitumor effects and the safety of administration are graphically illustrated below.

| Group | TGI | TGD 500 | Max. BW loss % |
|---|---|---|---|
| Group 1: Vehicle | | | 0.0% |
| Group 2: Thio-TEPA 2.5 mg/kg ip QDx5/wkx2wks | 68.3% | 26 | 0.4% |
| Group 3: Thio-TEPA 1.25 mg/kg ip QDx5/wkx2wks | 56.1% | 17 | 0.0% |
| Group 4: TH2660 10 mg/kg ip QDx5/wkx2wks | 60.7% | 20 | 3.3% |
| Group 6: TH2768 80 mg/kg ip QDx5/wkx2wks | 104.4% | >72 | 4.8% |
| Group 7: TH2768 40 mg/kg ip QDx5/wkx2wks | 100.6% | >72 | 0.0% |
| Group 8: TH2850 20 mg/kg ip QDx5/wkx2wks | 88.1% | >72 | 7.4% |
| Group 9: TH2850 10 mg/kg ip QDx5/wkx2wks | 94.3% | 70 | 0.9% |
| Group 10: TH2852 10 mg/kg ip QDx5/wkx2wks | 95.1% | >72 | 0.0% |
| Group 11: TH2870 20 mg/kg ip QDx5/wkx2wks | 102.3% | >72 | 1.6% |
| Group 12: TH2889 10 mg/kg ip QDx5/wkx2wks | 90.1% | 62 | 1.1% |

Doses were selected by first doing a toxicity test in CD1 mice as described above. The compounds were tested against Thio-tepa.

Example 4-C his study employed an A375 melanoma human tumor xenograft model and various compounds provided herein were compared to thiotepa and the approved anti melanoma drug, nab-Paclitaxel. The antitumor effects and the safety of administration are graphically illustrated below.

| Group | TGI | TGD 500 | TGD 1000 | Max. BW loss % |
|---|---|---|---|---|
| Group 1: Vehicle, qdx5x2, ip | | | | 0 |
| Group 2: Thio-TEPA, 2.5 mpk, qdx5x2, ip | 16.6% | 3 | 2 | 0 |
| Group 4: Abraxane, 30 mpk, 2x/wkx2, iv | 47.4% | 9 | 10 | 0 |
| Group 5: TH2768, 40 mpk, qdx5x2, ip | 36.7% | 7 | 7 | 0 |
| Group 6: TH2850, 10 mpk, qdx5x2, ip | 2.7% | -2 | 0 | 2.8 |
| Group 7: TH2852, 10 mpk, qdx5x2, ip | 12.4% | 3 | 1 | 2.6 |
| Group 8: TH2870, 20 mpk, qdx5x2, ip | 98.0% | 24 | >18 | 0 |
| Group 9: TH2873, 40 mpk, qdx5x2, ip | 65.0% | 12 | 11 | 0 |
| Group 10: TH2888, 10 mpk, qdx5x2, ip | 37.3% | 6 | 6 | 4.8 |
| Group 11: TH2889, 10 mpk, qdx5x2, ip | 75.6% | 13 | 15 | 0 |
| Group 12: TH2890 mpk, qdx5x2, ip | 58.4% | 10 | 10 | 6.3 |

Example 4-D

The compounds were tested in another A549 model. The compounds were dosed as follows. Daily IP dosing: 5 doses then 2 days off then 5 more doses starting at 100 mm$^3$ tumors on day 1 (10 animals per group average tumor volume). The antitumor effects and the safety of administration are graphically illustrated below.

| Group | TGI | TGD 500 | Max. BW loss % | Lethal Tox |
|---|---|---|---|---|
| Group 1: Vehicle | | | 0.9% | 0 |
| Group 2: TH2870 20 mg/kg IP QDx5/wkx2wks | 95.0% | >85 | 0.3% | 0 |
| Group 3: TH2883 10 mg/kg IP QDx5/wkx2wks | 93.5% | >85 | 15.8% | 5 |
| Group 4: TH2911 10 mg/kg IP QDx5/wks2wks | 88.7% | 63 | 11.1% | 0 |

-continued

| Group | TGI | TGD 500 | Max. BW loss % | Lethal Tox |
|---|---|---|---|---|
| Group 5: TH2931 5 mg/kg IP QDx5 | NA | NA | 25.0% | 10 |
| Group 6: TH2952 20 mg/kg IP QDx5/wkx2wks | 91.8% | 70 | 1.2% | 1 |
| Group 7: TH2953 40 mg/kg IP QDx5/wkx2wks | 93.8% | 64 | 1.6% | 0 |
| Group 8: TH2955 40 mg/kg IP QDx5/wkx2wks | 78.9% | 47 | 0.6% | 1 |
| Group 9: TH2958 5 mg/kg IP QDx5/wkx2wks | 77.9% | 44 | 2.1% | 0 |
| Group 10: TH2870 40 mg/kg IV 2/wks2wks | 98.6% | >85 | 2.0% | 1 |

Example 4-E

The compound TH-2768 was tested in a renal cell carcinoma 786-O model. The compound was dosed as follows. Daily IP dosing: 5 doses then 2 days off then 5 more doses starting at 220 mm$^3$ tumors on day 1 (10 animals per group average tumor volume). The antitumor effects and the safety of administration are graphically illustrated below.

| Group | TGI | Max. BW loss % |
|---|---|---|
| Group 1: Vehicle | | 0.5% |
| Group 2: TH2768, 40 mpk, ip, qdx5/wkx2 | 73.0% | 0.0% |
| Group 5: Sunitinib, 40 mpk, po, qdx5/wkx2 | 67.8% | 0.3% |
| Group 8: Sunitinib + TH2768 | 84.4% | 2.3% |

Example 4-F

The compounds TH-2953 and TH-3040 were tested in a H460 model. The compounds were dosed as follows. A dose-dependent TH-2953 was given IP once, from 6.25 to 100 mg/kg, comparing with daily IP: 5 doses then 2 days off then 5 more doses starting at 100 mm$^3$ tumors on day 1 (10 animals per group average tumor volume). TH-3040 was administered IP once. The antitumor effects and the safety of administration are graphically illustrated below.

| Group | TGI | TGD 500 | TGD 1000 | Max. BW loss % |
|---|---|---|---|---|
| Group 1: Vehicle | | | | 0.0% |
| Group 2: TH-2953, 100 mpk, ip, once | 97.7% | 24 | 27 | 0.0% |
| Group 3: TH-2953, 50 mpk, ip, once | 90.4% | 19 | 19 | 0.0% |
| Group 4: TH-2953, 25 mpk, ip, once | 86.1% | 18 | 20 | 0.2% |
| Group 5: TH-2953, 12.5 mpk, ip, once | 78.2% | 18 | 21 | 0.0% |
| Group 6: TH-2953, 6.25 mpk, ip, once | 72.2% | 16 | 17 | 0.0% |
| Group 7: TH-2953, 40 mpk, ip, QDx5/wkx2ks | 105.8% | 54 | 65 | 0.0% |
| Group 8: TH-3040, 100 mpk, ip, once | 93.7% | 20 | 23 | 0.0% |
| Group 9: TH-3040, 25 mpk, ip, once | 80.5% | 17 | 17 | 1.3% |

Example 4-G

The compounds TH-3040 and TH-3045 were tested in a H460 model. The compounds were dosed as follows. A dose-dependent TH-3040 or TH-3045 was given IP weekly for 3 weeks, from 5 to 45 mg/kg starting at 100 mm$^3$ tumors on day 1 (10 animals per group average tumor volume). The antitumor effects and the safety of administration are graphically illustrated below.

| Group | TGI | TGD500 | Max BW loss |
|---|---|---|---|
| Group 1: Vehicle, ip, Q7Dx3 | | | |
| Group 2: TH-3040 5 mpk. ip, Q7Dx3 | 103.5% | 40 | 2.5% |
| Group 3: TH-3040 15 mpk. ip, Q7Dx3 | 104.3% | 60 | 1.0% |
| Group 4: TH-3040, 45 mpk, ip, Q7Dx3 | 106.4% | 66 | 0.0% |
| Group 5: TH-3045, 5 mpk, ip, Q7Dx3 | 104.0% | 48 | 0.0% |
| Group 6: TH-3045, 15 mpk, ip, Q7Dx3 | 104.8% | 70 | 2.8% |
| Group 7: TH-3045, 45 mpk, ip, Q7Dx3 | 106.3% | 86 | 2.4% |

Example 4-H

The compound TH-3040 was tested in a H460 model. The compound was dosed as follows: 5 or 1.5 mg/kg, IP, weekly for 3 weeks at 100 mm$^3$ tumors on day 1 (10 animals per group average tumor volume), comparing with nab-Paclitaxel. The antitumor effects and the safety of administration are graphically illustrated below.

| Group | TGI | TGD500, Days (vs. vehicle) | TGD1000, Days (vs. vehicle) | Max. BW loss % |
|---|---|---|---|---|
| Group 1: Vehicle | | | | 0.0% |
| Group 6: TH3040 5 mg/kg, ip, Q7Dx3 | 101.9% | 36 | 41 | 5.2% |
| Group 7: TH3040 1.5 mg/kg, ip, Q7Dx3 | 80.6% | 15 | 19 | 7.2% |
| Group 11: ABX 30 mg/kg, iv, 2/wkx2wks | 49.7% | 9 | 10 | 11.6% |
| Group 12: ABX 10 mg/kg, iv, 2/wkx2wks | −12.5% | −2 | −1 | 1.2% |

Example 4-I

The compound TH-2870 was tested in a H460 model. The compound was dosed follows. 1.5, 5 or 15 mg/kg, IV, weekly for 3 weeks at 250 mm$^3$ tumors on day 1 (10 animals per group average tumor volume), comparing with docetaxel. The antitumor effects and the safety of administration are graphically illustrated below.

| Group | TGI | TGD500, Days (vs. vehicle) | TGD1000, Days (vs. vehicle) | Max. BW loss % |
|---|---|---|---|---|
| Group 1: Vehicle | | | | 0.0% |
| Group 2: TH2870 1.5 mg/kg iv, Q7Dx3 | 100.0% | 18 | 18 | 7.6% |
| Group 3: TH2870 5 mg/kg iv, Q7Dx3 | 121.3% | 36 | 38 | 7.6% |

-continued

| Group | TGI | TGD500, Days (vs. vehicle) | TGD1000, Days (vs. vehicle) | Max. BW loss % |
|---|---|---|---|---|
| Group 4: TH2870 15 mg/kg iv, Q7Dx3 | 121.6% | 49 | 50 | 5.8% |
| Group 5: Doectaxel 10 mg/kg, iv, Q7Dx3 | 51.3% | 6 | 9 | 12.4% |

Taken together these studies demonstrate significant anti tumor efficacy in 4 different tumor cell lines relative to standard chemotherapeutics.

Example 5. Pharmacokinetics and Activation of TH 2870 by the Aldoketo Reductase, AKR1C3

Recombinant human AKR1C3 was diluted to 25 µg/mL in phosphate buffered saline (PBS), pH 7.4 (37° C.), containing 2 mM NADPH. TH2870 or progesterone (positive control) in 30% methanol/70% water was added to the reaction mixture at a final concentration of 5 µM and incubated at 37° C. for 120 minutes. At various times up to 120 min, 50 µL of the reaction mixture was taken and 200 µL acetonitrile containing propranolol as internal standard was added, vortex-mixed and centrifuged for 10 min. The resulting supernatant (5 µL) was injected into a LC/MS/MS for quantitation of remaining TH2870 and progesterone. The compounds were tested in duplicate.

| | % Remaining | |
|---|---|---|
| Time min | TH2870 | Progesterone |
| 0 | 100% | 100% |
| 15 | 0.232% | 70.8% |
| 30 | 0.0101% | 49.2% |
| 60 | 0.00% | 20.1% |
| 90 | 0.00% | 10.6% |
| 120 | 0.00% | 6.40% |

The data above demonstrates the rapid disappearance of TH2870 in the presence of AKR1C3 while the known substrate, progesterone, is reduced slowly.

The pharmacokinetics of TH2870 in CD-1 mice following a single intravenous bolus dose (5 mg/kg) and a single intraperitoneal dose (10 mg/kg) were determined.

| Route | IV | IP |
|---|---|---|
| Dose (mg/kg) | 5 | 10 |
| Tmax (min) | 2.00 | 5.00 |
| Cmax (µg/mL) | 6.79 | 4.02 |
| Half-Life (min) | 6.56 | 9.00 |
| AUC (µg-min/mL) | 57.8 | 43.5 |
| Cl (L/min/kg) | 0.0865 | — |
| Vss (L/kg) | 0.668 | — |

The pharmacokinetics of TH2870 were determined in Mouse/Nu-Foxn1$^{nu}$ NU/NU mice with A549 (non small cell lung), A375 (melanoma) and 786-O (renal cell) human tumor xenograft models following a single intraperitoneal dose of 20 mg/kg. TH2870 concentrations in the brain, liver and tumor were only a fraction of the concentrations in plasma, ranging between 0.79% (brain)-32.6% (liver). In the A375 and 786-O xenograft models, the concentrations of TH2660 was ~24-29-fold and ~15-19-fold higher in tumor and liver than TH2870, suggesting preferential activation of TH2870 in the tumor as compared to the liver. In the A549 xenograft, there was an even greater activation of TH2870 in tumor as compared to the liver of ~148-fold and ~13-fold, respectively.

| | TH2870 | | | TH2660 | | |
|---|---|---|---|---|---|---|
| | A549 | A375 | 786-O | A549 | A375 | 786-O |
| Tmax (min) | 5.00 | 5.00 | 5.00 | 5.00 | 15.0 | 15.0 |
| Cmax (µg/mL) | 5.01 | 3.41 | 6.06 | 0.142 | 0.159 | 0.191 |
| Half-Life (min) | 11.3 | 14.7 | 12.3 | 28.4 | 30.2 | 10.6 |
| AUC (µg-min/mL) | 94.1 | 57.7 | 64.8 | 9.55 | 9.03 | 32.9 |

The pharmacokinetics of TH2873, TH2883, TH2888, TH2890, TH2901 and TH2926 were determined in CD-1 mice following a single intraperitoneal dose.

| | TH2873 | TH2883 | TH2888 | TH2889 | TH2890 | TH2901 | TH2926 |
|---|---|---|---|---|---|---|---|
| Tmax (min) | 5.00 | 15.0 | 5.00 | 5.00 | 5.00 | 5.00 | 15.0 |
| Cmax (µg/mL) | 8.43 | 7.57 | 5.81 | 2.48 | 2.73 | 5.12 | 8.34 |
| Half-Life (min) | 8.81 | 23.4 | 10.9 | 10.3 | 5.49 | 12.1 | 34.2 |
| AUC (µg-min/mL) | 126 | 545 | 96.3 | 35.9 | 36.8 | 155 | 579 |

The pharmacokinetics of TH2660, the active metabolite, following a single intraperitoneal dose of TH2873, TH2883, TH2888, TH2890, TH2901 and TH2926 are shown below.

| | TH2873 | TH2883 | TH2888 | TH2889 | TH2890 | TH2901 | TH2926 |
|---|---|---|---|---|---|---|---|
| Tmax (min) | 5.0 | 30.0 | 30.0 | 30.0 | 15.0 | 30.0 | 30.0 |
| Cmax (µg/mL) | 9.85 | 0.147 | 0.3367 | 0.277 | 0.455 | 0.265 | 0.038 |
| Half-Life (min) | 9.80 | 41.6 | 17.8 | 15.4 | 15.2 | 20.4 | 88.6 |
| AUC (µg-min/mL) | 125 | 11.7 | 20.6 | 15.8 | 17.0 | 15.3 | 5.06 |

The pharmacokinetics of TH2953 were determined in Mouse/Nu-Foxn 1$^{nu}$ NU/NU mice with two non small cell lung human tumor xenograft models,

|  | A549 |  | H460 |
| --- | --- | --- | --- |
| Dose (mg/kg) | 10 | 40 | 10 |
| Tmax (min) | 30.0 | 30.0 | 15.0 |
| Cmax (µg/mL) | 0.149 | 14.8 | 2.33 |
| Half-Life (min) | 100.00 | 91.3 | 142 |
| AUC (µg-min/mL) | 266 | 2341 | 444 |

The pharmacokinetics of TH2660, the active metabolite, following a single intraperitoneal dose of TH2953 are shown below.

|  | A549 |  | H460 |
| --- | --- | --- | --- |
| Dose (mg/kg) | 10 | 40 | 10 |
| Tmax (min) | 15.0 | 60.0 | NC |
| Cmax (µg/mL) | 0.0202 | 0.0960 | 0.00 |
| Half-Life (min) | NC | 9.69 | NC |
| AUC (µg-min/mL) | 2.94* | 39.8 | 0.00 |

*AUClast

A549 and H460, following a single intraperitoneal dose of 10 and 40 mg/kg for A549 and 10 mg/kg for H460. TH2953 concentrations in the brain, liver and tumor were 55.0-73.8%, 297-541% and 2.08-8.34% of the concentrations in plasma in the A549 tumor xenograft. In the H460 xenograft model, the concentrations of TH2660 were ~9.6-fold and ~2-fold higher in tumor and liver than TH2953, suggesting preferential activation of TH2953 in the tumor as compared to the liver. In the A549 xenograft, the preferential activation of TH2953 was more pronounced as the concentrations of TH2660 in the tumor were 5-7-fold greater than for TH2953, while they were only ~13-15% in the liver.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:

1. A compound of formula I:

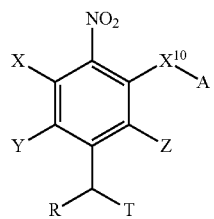

I or a pharmaceutically acceptable salt, or a solvate of each thereof, wherein $X^{10}$ is O, S, SO, or $SO_2$;

A is $C_6$-$C_{10}$ aryl, 5-15 membered heteroaryl, or —N=$CR^1R^2$;

each $R^1$ and $R^2$ independently is hydrogen, -13 CN, $C_1$-$C_6$ alkyl, $C_3$-$C_8$ cycloalkyl, $C_6$-$C_{10}$ aryl, 4-15 membered heterocycle, 5-15 membered heteroaryl, ether, —$CONR^{13}R^{14}$, or —$NR^{13}COR^{14}$;

each X and Z independently is hydrogen or $C_1$-$C_6$ alkyl;

Y is hydrogen, halo, or $C_1$-$C_6$ alkyl;

R is hydrogen or $C_1$-$C_6$ alkyl;

each $R^{13}$ and $R^{14}$ independently is hydrogen, $C_1$-$C_6$ alkyl, $C_3$-$C_8$ cycloalkyl, $C_6$-$C_{10}$ aryl, 4-15 membered heterocycle, 5-15 membered heteroaryl, or ether;

T is OP($Z^1$)(NHCH$_2$CH$_2$Cl)$_2$, OP($Z^1$)(NHCH$_2$CH$_2$Br)$_2$, OP($Z^1$)(NH$_2$)(N(CH$_2$CH$_2$X$^1$)$_2$), OP($Z^1$)(N(CH$_2$)$_2$)$_2$, or OP($Z^1$)(N(CH$_2$CH$_2$C$_1$)$_2$)$_2$, wherein $Z^1$ is O or S, and $X^1$ is $C_1$, Br, or OMs; and wherein the alkyl, cycloalkyl, aryl, heterocycle, heteroaryl, ether groups are optionally substituted.

2. The compound of claim 1, wherein T is OP(O)(N(CH$_2$CH$_2$))$_2$, OP(O)(NHCH$_2$CH$_2$Cl)$_2$, OP(O)(NHCH$_2$CH$_2$Br)$_2$, or OP(O)(NH$_2$)(N(CH$_2$CH$_2$Cl)$_2$).

3. The compound of claim 1, wherein A is optionally substituted $C_6$-$C_{10}$ aryl.

4. The compound of claim 3, wherein A is optionally substituted phenyl.

5. The compound of claim 1, wherein A is optionally substituted 5-15 membered heteroaryl.

6. The compound of claim 5, wherein A is optionally substituted pyridyl.

7. The compound of claim 1, wherein A is —N=$CR^1R^2$ where $R^1$ and $R^2$ are defined as in claim 1.

8. The compound of claim 1, wherein R is methyl.

9. The compound of claim 1, wherein the compound is

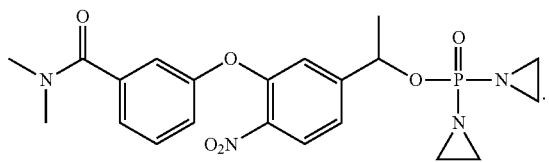 [SMILES: CC(OP(=O)(N1CC1)N1CC1)c1ccc([N+](=O)[O-])c(Oc2cccc(C(=O)N(C)C)c2)c1]

10. A pharmaceutically acceptable composition comprising a compound of claim 1 and at least a pharmaceutically acceptable excipient or carrier.

11. A process of making the compound of formula I of claim 1 comprising contacting a compound of formula II:

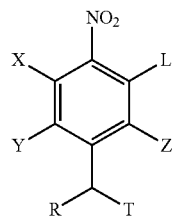

II wherein L is a leaving group, and the remaining variables are defined as in claim 1, with a compound of formula III:

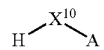
wherein $X^{10}$ is defined as in claim 1, and optionally a base, to provide a compound of formula I.
* * * * *